United States Patent
Masuo

(10) Patent No.: US 7,979,114 B2
(45) Date of Patent: Jul. 12, 2011

(54) APPARATUS FOR ASSUMING INFORMATION ON THE AMOUNT ACCUMULATED VISCERAL FAT OF A HUMAN BODY

(75) Inventor: Yoshihisa Masuo, Otsu (JP)

(73) Assignee: Tanita Corporation, Tokyo (JP)

( * ) Notice: Subject to any disclaimer, the term of this patent is extended or adjusted under 35 U.S.C. 154(b) by 1387 days.

(21) Appl. No.: 11/491,036

(22) Filed: Jul. 24, 2006

(65) Prior Publication Data

US 2007/0043302 A1 Feb. 22, 2007

(30) Foreign Application Priority Data

Aug. 18, 2005 (JP) .................................. 2005-237795

(51) Int. Cl.
*A61B 5/05* (2006.01)
(52) U.S. Cl. .................... 600/547; 600/301; 600/529
(58) Field of Classification Search .................. 600/547, 600/300, 309, 529–543
See application file for complete search history.

(56) References Cited

U.S. PATENT DOCUMENTS

| 3,797,479 A | 3/1974 | Graham |
| 5,058,601 A | 10/1991 | Riker |
| 2003/0120164 A1 | 6/2003 | Nielsen et al. |
| 2004/0059242 A1 * | 3/2004 | Masuo et al. ................ 600/547 |
| 2004/0077969 A1 * | 4/2004 | Onda et al. .................... 600/547 |
| 2005/0059902 A1 | 3/2005 | Itagaki |
| 2005/0070778 A1 | 3/2005 | Lackey et al. |
| 2005/0107717 A1 * | 5/2005 | Yamamoto et al. ........... 600/547 |
| 2005/0192488 A1 * | 9/2005 | Bryenton et al. ............. 600/301 |
| 2005/0222516 A1 * | 10/2005 | Kasahara et al. ............. 600/547 |
| 2006/0183980 A1 * | 8/2006 | Yang ............................. 600/301 |
| 2009/0093732 A1 * | 4/2009 | Kasahara et al. ............. 600/547 |

FOREIGN PATENT DOCUMENTS

| JP | 11-123182 | 5/1999 |
| JP | 2002-125954 | 5/2002 |
| WO | WO 01/78600 A1 | 10/2001 |

OTHER PUBLICATIONS

European Office Action issued in European Patent Application No. EP 06 013 751.0-1526, dated Feb. 3, 2009.
European Search Report issued in European Patent Application No. EP 06 01 3751, mailed Oct. 10, 2007.

* cited by examiner

*Primary Examiner* — Charles A Marmor, II
*Assistant Examiner* — Karen E Toth
(74) *Attorney, Agent, or Firm* — McDermott Will & Emery LLP

(57) ABSTRACT

Disclosed is an apparatus for assuming the information on the amount accumulated visceral fat in a human body with a high degree of accuracy. It comprises: at least a unit for collecting pieces of information on the identification of the human body and a unit for collecting pieces of information on breathing function, thereby making the visceral fat accumulation calculating unit provide the information on the amount accumulated visceral fat based on the so collected pieces of information.

14 Claims, 30 Drawing Sheets

APPARATUS FOR ASSUMING INFORMATION ON THE AMOUNT ACCUMULATED VISCERAL FAT OF A HUMAN BODY

FIELD OF THE INVENTION

The present invention relates to an apparatus for assuming information on the amount accumulated visceral fat of a human body on the basis of pieces of information on the identification of the human body and the breathing function.

BACKGROUND OF THE INVENTION

A conventional visceral fat assuming apparatus was designed to calculate the amount accumulated visceral fat of a human body on the basis of at least one of: pieces of information on the identification of the human body (including some indicators or indexes representing the features or attributes of the whole body or the shape and size of the whole body or selected parts of the body); pieces of information representing the body composition (including some indicators or indexes representing the intracorporal composition); and bioelectrical impedance appearing between two selected points on the human body, which bioimpedance can be determined in terms of the potential difference appearing between the two selected points when a given fixed electric current is made to flow from one to the other selected point on the body.

For example, the visceral fat meter of Patent Document 1 below is designed to calculate the visceral fat rate (corresponding to the "information on the amount accumulated visceral fat", herein referred to as such) from the impedance determined with a string of electrodes arranged around the trunk (corresponding to the "bioelectrical impedance", herein referred to as such) and the length of the abdominal circumference (corresponding to "information on the identification of the human body", herein referred to as such).

For another example, the visceral fat meter of Patent Document 2 below is designed to calculate the area of the cross section of the abdominal visceral fat (corresponding to the information on the amount accumulated visceral fat) from: the WHR or waist-hip ratio entered (corresponding to the information on the identification of the human body); the WHR and the body fat rate entered (corresponding to the information representing the body composition); or the WHR entered and the bioimpedance determined (corresponding to the bioelectrical impedance).

The visceral fat meter of Patent Document 3 below is designed to calculate the visceral fat area (corresponding to the information on the amount accumulated visceral fat) from the abdominal circumference determined and the age entered (both corresponding to the information on the identification of the human body).

Patent Document 1: Patent Application Laid-Open No. H 11-123182;
Patent Document 2: WO01/078600 and
Patent Document 3: Patent Application Laid-Open No. 2002-125954

SUMMARY OF THE INVENTION

The accuracy with which the conventional visceral fat assuming apparatus can calculate the amount accumulated visceral fat depends on how closely the visceral fat amount is connected with the identified features of the human body, the identified body composition and/or determined bioelectrical impedance. As a matter of fact, no matter which factor or factors may be selected, the degree of accuracy cannot be improved beyond certain limits.

In view of this, the object of the present invention is to provide an apparatus capable of assuming information on the amount accumulated visceral fat of a human body with a high degree of accuracy.

To attain this object an apparatus for assuming information on the amount accumulated visceral fat of a human body according to the present invention comprises:
 a body identifying unit;
 a breathing function determining unit; and
 a computing unit,
 wherein said body identifying unit obtains information on the identification of the human body;
 said breathing function unit obtains information on the breathing function; and
 said computing unit calculates information on the amount accumulated visceral fat on the basis of the so obtained pieces of information on the identification of the human body and the breathing function.

The breathing function determining unit may comprise a breathing amount determining unit which determines the breathing amount both at the time of maximum inspiration and at the time of expiration, and a vital capacity computing unit which calculates pieces of information on the breathing function on the basis of the amounts of the maximum inspiration and maximum expiration thus determined.

The breathing function determining unit may comprise a trunk bioimpedance variation determining unit which determines the variation between the trunk bioimpedance at the time of maximum inspiration and that at the time of maximum expiration, and a vital capacity computing unit which calculates information on the breathing function on the basis of the so determined trunk bioimpedance variation between the maximum inspiration and maximum expiration.

The apparatus for assuming information on the amount accumulated visceral fat of a human body may further comprise a body composition determining unit which obtains information on the body composition of the human body, thus permitting said computing unit to calculate information on the amount accumulated visceral fat on the basis of, among others, the so obtained pieces of information on the body composition of the human body.

The body composition determining unit may comprise a hand-to-hand bioimpedance determining unit which determines the bioimpedance appearing between both hands, and a body composition calculating unit which calculates information on the body composition of the human body on the basis of the so determined hand-to-hand bioimpedance.

The body composition determining unit may comprise a limb bioimpedance determining unit which determines the bioimpedance appearing between two selected limbs, a trunk bioimpedance determining unit which determines the bioimpedance appearing between two selected points of the trunk, and a body composition calculating unit which calculates the body composition on the basis of the so determined limb bioimpedance and trunk bioimpedance.

The information on the identification of the human body may include sex, age, height and weight, and the information on the breathing function includes vital capacity.

The information on the identification of the human body may include sex, age, height and weight, and at least one of the upper limb length, lower limb length, trunk length and abdominal circumference, and the information on the breathing function includes vital capacity.

The information on the identification of the human body may include sex, age, height and weight; the information on the breathing function include vital capacity; and the information on the body composition may include the trunk skeletal muscle rate.

The information on the identification of the human body may include sex, age, height and weight, and at least one of the upper limb length, lower limb length, trunk length and abdominal circumference; the information on the breathing function include vital capacity; and the information on the body composition may include the trunk skeletal muscle rate.

The information on the amount accumulated visceral fat may include at least one of the visceral fat rate, visceral fat amount (mass) and the ratio of visceral fat/subcutaneous fat.

ADVANTAGEOUS EFFECTS

The apparatus for assuming information on the amount accumulated visceral fat of a human body according to the present invention provides the following advantages:
the computing unit carries out a required arithmetic operation to calculate the information on the amount accumulated visceral fat on the basis of the pieces of information concerning the identification of the human body and breathing function, thereby providing the information on the amount accumulated visceral fat with a high degree of accuracy because of being not influenced by the visceral mass, the subcutaneous fat amount (mass) and the rectus abdominis muscle mass Also, the breathing function determining unit comprises a breathing amount determining unit which determines the breathing amount both at the time of maximum inspiration and at the time of expiration, and a vital capacity computing unit which calculates pieces of information on the breathing function on the basis of the amounts of the maximum inspiration and maximum expiration thus determined. And, the breathing function determining unit comprises a trunk bioimpedance variation determining unit which determines the variation between the trunk bioimpedance at the time of maximum inspiration and that at the time of maximum expiration, and a vital capacity computing unit for calculating information on the breathing function on the basis of the so determined trunk bioimpedance variation between the maximum inspiration and maximum expiration. These sure permit estimation of the amount accumulated visceral fat with a high degree of accuracy.

The breathing function determining unit a trunk bioimpedance variation determining which determines the variation between the trunk bioimpedance at the time of maximum inspiration and that at the time of maximum expiration, and a vital capacity computing unit which calculates information on the breathing function on the basis of the so determined trunk bioimpedance variation between the maximum inspiration and maximum expiration. this sure permits estimation of the amount accumulated visceral fat with a high degree of accuracy.

The body composition determining unit for obtaining information on the body composition of the human body permits the computing unit to calculate information on the amount accumulated visceral fat on the basis of, among others, the so obtained pieces of information on the body composition of the human body. This arrangement sure permits estimation of the amount accumulated visceral fat with a still higher degree of accuracy, because of being not influenced by the visceral mass, the subcutaneous amount (mass) and the rectus abdominis.

The body composition determining unit comprises a hand-to-hand bioimpedance determining unit which determines the bioimpedance appearing between both hands, and a body composition calculating unit which calculates information on the body composition of the human body on the basis of the so determined hand-to-hand bioimpedance. Alternatively, the body composition determining unit comprises a limb bioimpedance determining unit which determines the bioimpedance appearing between two selected limbs, a trunk bioimpedance determining unit which determines the bioimpedance appearing between two selected points of the trunk, and a body composition calculating unit which calculates the body composition on the basis of the so determined limb bioimpedance and trunk bioimpedance. These sure permit estimation of the amount accumulated visceral fat with a still higher degree of accuracy.

The information on the identification of the human body include sex, age, height and weight, and the information on the breathing function includes vital capacity. Additionally, the information on the identification of the human body include at least one of the upper limb length, lower limb length, trunk length and abdominal circumference. The information on the body composition includes the trunk skeletal muscle rate. Selection of such factors help enable estimation of the amount accumulated visceral fat with a highest possible degree of accuracy.

The information on the amount accumulated visceral fat includes at least one of the visceral fat rate, visceral fat amount (mass) and the ratio of visceral fat/subcutaneous fat. Conveniently the apparatus can be designed to estimate the amount accumulated visceral fat in respect of any one of such variables.

BEST MODES OF REDUCING THE INVENTION INTO PRACTICE

As shown in FIG. 1, an apparatus for assuming information on the amount accumulated visceral fat of a human body according to the present invention comprises: a body identifying unit for obtaining information on the identification of the human body 1; a breathing function determining unit for obtaining information on the breathing function 2; a body composition determining unit for obtaining information on the body composition 3 and a computing unit for calculating information on the amount accumulated visceral fat 4.

The body identifying unit 1 functions to obtain information on the identification of a human body, which include some indexes or indicators representing the features or attributes of the whole body or the shape and size of the whole body or selected parts of the body, such as sex (Sex), age (Age), height (H), weight (W), upper limb length (Lu), lower limb length (Ll), trunk length (Ltm), abdominal circumference (Lw) and the like. Particularly the weight (W) is closely related with the degree of development of the skeletal muscle of the whole body, which affects the oxygen uptake amount, and therefore, the weight (W) can be a noticeable indicator representing the influence on the vital capacity. Therefore, using the weight (W) as a piece of information identifying one aspect of the body is vital in estimating the quantities of the amount accumulated visceral fat.

As for the breathing function determining unit for obtaining information on the breathing function 2: the required information is given as indexes or indicators representing the load capacity on the lungs in breathing such as vital capacity (VC), forced vital capacity (FVC), standard vital capacity (VC0), one-second-forced expiratory volume (FEV1.0), one-second-forced expiratory volume % rate (FEV1.0%) or vital capacity/standard vital capacity percent (VC %). Specifically the breathing function determining unit 2 comprises a breathing amount determining unit 5 for determining the breathing amount in respect of the maximum inspiration and maximum expiration, and a vital capacity computing unit 6 for calculating pieces of information concerning the breathing function on the basis of the amounts of maximum inspiration and maximum expiration thus determined. Alternatively the breathing function determining unit 2 comprises a trunk bioimpedance variation determining unit for determining the trunk bioimpedance variation between the maximum inspiration and the maximum expiration 7, and a vital capacity computing unit 8 for calculating information on the breathing function on the basis of the so determined inter-maximum expiration and maximum inspiration trunk bioimpedance variation. It should be noted that the vital capacity (VC) or the forced vital capacity (FVC) noticeably indicates the variation of the diaphragm or midriff. Such variables, therefore, are very useful in estimating the amount accumulated visceral fat.

The terms concerning the breathing function are defined as follows:

"vital capacity (VC)" is the amount of the air which one can inspire as much as possible and then expire as much as possible;

"forced vital capacity (FVC)" is one aspect of "vital capacity (VC)" in meaning, and is the amount of the air which one can inspire as much as possible and then expire as much as possible quickly at one burst;

"standard vital capacity (VC0)" is equivalent to the vital capacity (forced vital capacity) a person who is normalized in respect of sex, age or height is supposed to have, and is called "expected vital capacity", also;

"one-second-forced expiratory volume (FEV1.0)" is the amount (volume) of the air which is measured when one sends the air out of one's lungs for the first one second in the forced expiratory process;

"one-second-forced expiratory volume % rate (FRV1.0%)" is equal to the number which is the result when the one-second-forced expiratory volume (FEV1.0) is divided by the forced vital capacity (FVC), the quotient indicating the degree of easiness for breathing; and "vital capacity/standard vital capacity percent (VC %)" is the ratio of the vital capacity (forced vital capacity) to the standard vital capacity, expressed in percentage terms.

As for the body composition determining unit for obtaining information on the body composition 3 the required pieces of information are given as representing different kinds of body composition (excluding the information on the amount accumulated visceral fat) as for example follows:

body fat values (body fat rate (% Fat), body fat amount (mass));

fat-free mass values (fat-free mass rate, lean body mass (LBM));

limb skeletal muscle values (lower limb skeletal muscle mass (MMl), upper limb skeletal muscle mass (MMu), lower limb skeletal muscle mass bioimpedance (Zl), upper limb skeletal muscle bioimpedance (Zu));

trunk skeletal muscle values (trunk skeletal muscle rate (% MM), middle trunk skeletal muscle rate, trunk skeletal muscle mass, middle trunk skeletal muscle mass (MMtm), trunk skeletal muscle bioimpedance, middle trunk skeletal muscle bioimpedance (ZMM));

abdominal subcutaneous fat values (abdominal subcutaneous rate, abdominal subcutaneous fat amount (mass) (FS, FSa), abdominal subcutaneous fat bioimpedance (ZFS));

some values concerning the visceral organs (visceral rate, visceral mass (VM), visceral bioimpedance (ZVM));

trunk mass (TM), and some values concerning visceral fat (visceral fat bioimpedance (ZFV).

Specifically, the body composition determining unit 3 comprises a hand-to-hand bioimpedance determining unit 9 for measuring the hand-to-hand bioimpedance appearing between both hands, and a body composition calculating unit 10 for calculating the information on the body composition on the basis of the so determined hand-to-hand bioimpedance. Alternatively the body composition determining unit 3 comprises a limb bioimpedance determining unit 11 for determining the bioimpedance appearing two selected points on arm or a leg, a trunk bioimpedance determining unit 12 for determining the bioimpedance appearing between two selected points of the trunk, and a body composition calculating unit 13 for calculating the information concerning the body composition on the basis of the so determined limb bioimpedance and trunk bioimpedance. It should be noted that the trunk skeletal muscle rate (% MM) noticeably indicates the degree of development of the whole body in skeletal muscle, which has a significant influence on oxygen uptake. Such variable, therefore, is very useful in estimating the visceral fat amount (mass).

The computing unit 4 for calculating information on the amount accumulated visceral fat functions to carry out a required arithmetic operation on the basis of pieces of information concerning the identification of the body provided by the unit 1, the breathing function provided by the unit 2 and the body composition provided by the unit 3. The information on the amount accumulated visceral fat is given for example, in the form of visceral fat rate (% VFat), visceral fat amount (mass) (FV) or ratio of visceral fat/subcutaneous fat (V/S). It should be noted that advantageously directly from these particular indexes or indicators one can instinctively feel how much fat is accumulated in one's viscera.

Referring to FIGS. 2 and 3, how and why the degree of accuracy can be improved in estimating the amount accumulated visceral fat according to the present invention is described below: FIG. 2a illustrates dynamic models of a lean body (non-visceral obesity) at the time of maximum expiration (left) and at the time of maximum inspiration (right) respectively, each shown as comprising a lung LM, intercostal muscles MMi, a diaphragm DM, visceral fat FV, visceral mass VM, rectus abdominis muscle MMr and subcutaneous fat FS whereas FIG. 2b illustrates similar dynamic models of a fat body (visceral obesity). FIG. 3 is a graph showing how the vital capacity/height varies with the visceral fat rate.

As seen from FIGS. 2a and 2b, the abdominal internal pressure resistance is almost free of being influenced by the mass of the subcutaneous fat (FS) or rectus abdominis muscle (MMr). It, however, increases with the increase of the visceral mass (VM) (liver, stomach, bowel, kidney, pancreas, bladder and other visceral organs), and with the increase of the visceral fat mass (FV), decreasing with the decrease of these factors (VM and FV). When one takes the air into one's lungs, the intercostal muscles (MMi) extends itself, and the lung expands itself, and then the diaphragm (DM) pushes down the visceral organs and visceral fat. As indicated by a thick both-headed arrow in FIG. 2a, the degree of "pushing-down" is large when the visceral organs and fat accumulation are small in quantities. In contrast, as indicated by a thick both-headed arrow in FIG. 2b, the degree of "pushing-down" is small when the visceral organs and fat accumulation are large in quantities. The visceral mass is almost constant in value, and can be given as such in the information on the body identification. In contrast, the vital capacity significantly varies with the accumulation in the visceral fat, particularly the visceral fat rate, as seen from FIG. 3. Specifically, the vital capacity increases with the decrease of the visceral fat, and the vital capacity decreases with the increase of the visceral fat (this tendency is still more noticeable in the abdominal breathing region than the breast breathing region). It should be noted that the accumulation in the visceral fat varies with the body composition, also.

The above is effectively used in the apparatus for assuming information on the amount accumulated visceral fat according to the present invention, the computing unit 4 of which functions to calculate the information on the amount accumulated visceral fat on the basis of the information on the body identification provided by the unit 1, the information on the breathing function provided by the unit 2 and the information on the body composition provided by the unit 3 (optional), thus making the calculated information on the amount accumulated visceral fat free of any influence from the visceral organs, the pannicule and the rectus abdominis. The information on the amount accumulated visceral fat, therefore, can be estimated with a high degree of accuracy.

The breathing function determining unit 2 for obtaining information on the breathing function allows the vital capacity computing unit 6 to determine the breathing function in terms of the breathing amount provided by the vital capacity computing unit 6 at the time of maximum inspiration and at the time of maximum expiration respectively. Or otherwise, the breathing function determining unit 2 allows the vital capacity computing unit 8 to determine the breathing function in terms of the trunk bioimpedance variation provided by the trunk bioimpedance variation determining unit 7, which determines the trunk bioimpedance variation between the maximum inspiration and the maximum expiration. The alternatives sure provide the result with a high degree of accuracy.

With a view to providing a still higher degree of accuracy the computing unit 4 for calculating information on the amount accumulated visceral fat performs a required arithmetic operation on the basis of pieces of information concerning the body identification, breathing function and body composition. A good accuracy, however, can be provided only with recourse to the information on the body identification and the breathing function.

The visceral organs, visceral fat, skeletal muscle, diaphragm and subcutaneous fat all referred to herein form tissue, and particularly the skeletal muscle, the diaphragm and the subcutaneous fat appear in laminated tissue. The visceral organs and the visceral fat are complicate in structure.

Now, some embodiments of the present invention are described below with reference to drawings:

FIG. 2(*a*) illustrates the visceral working mode in case of small amount of visceral fat accumulation whereas FIG. 2(*b*) illustrates the visceral working mode in case of large amount of visceral fat accumulation;

Figure 26:
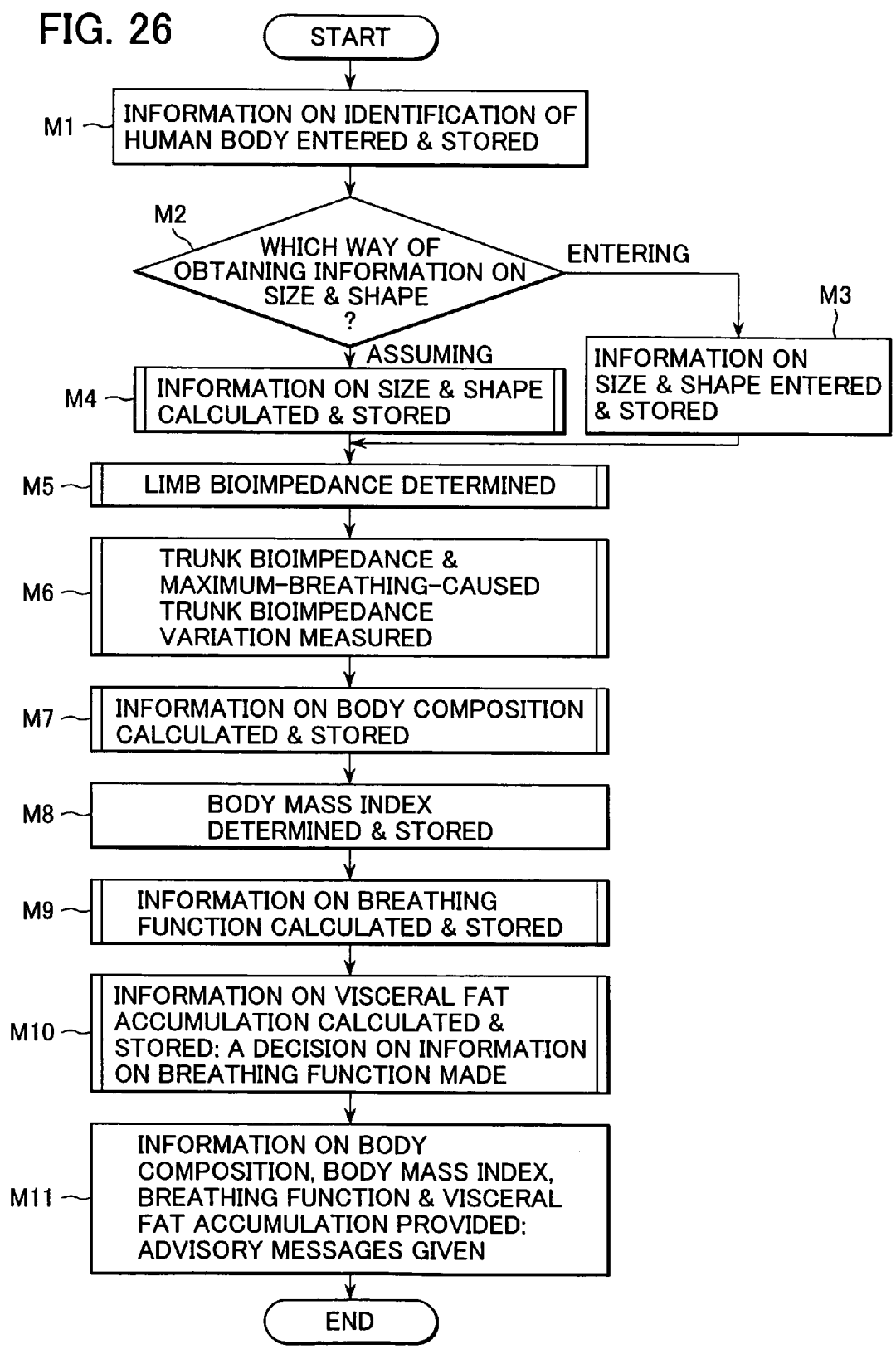
FIG. 26 is a main flow chart depicting how the apparatus for assuming information on the amount accumulated visceral fat of EMBODIMENT 4 works.
Figure 31:
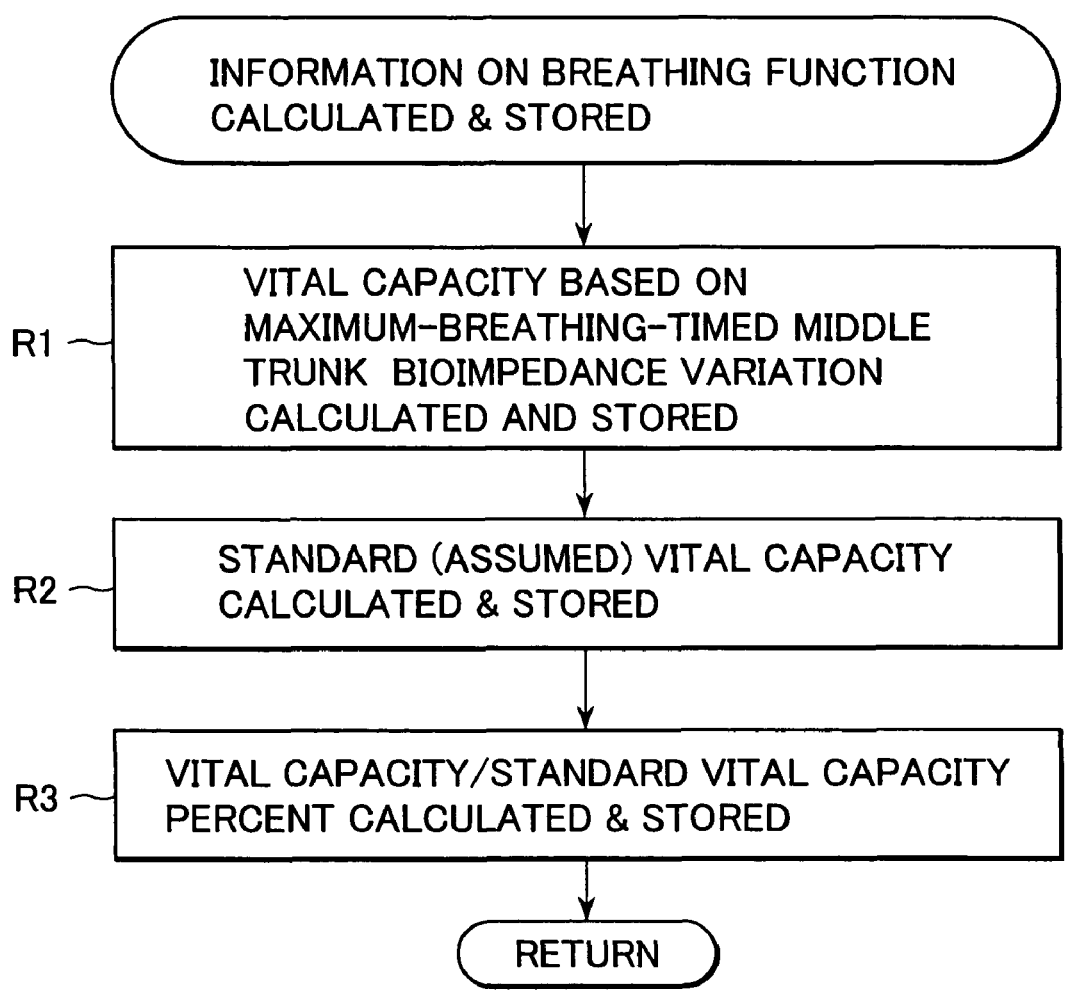
Figure 32:
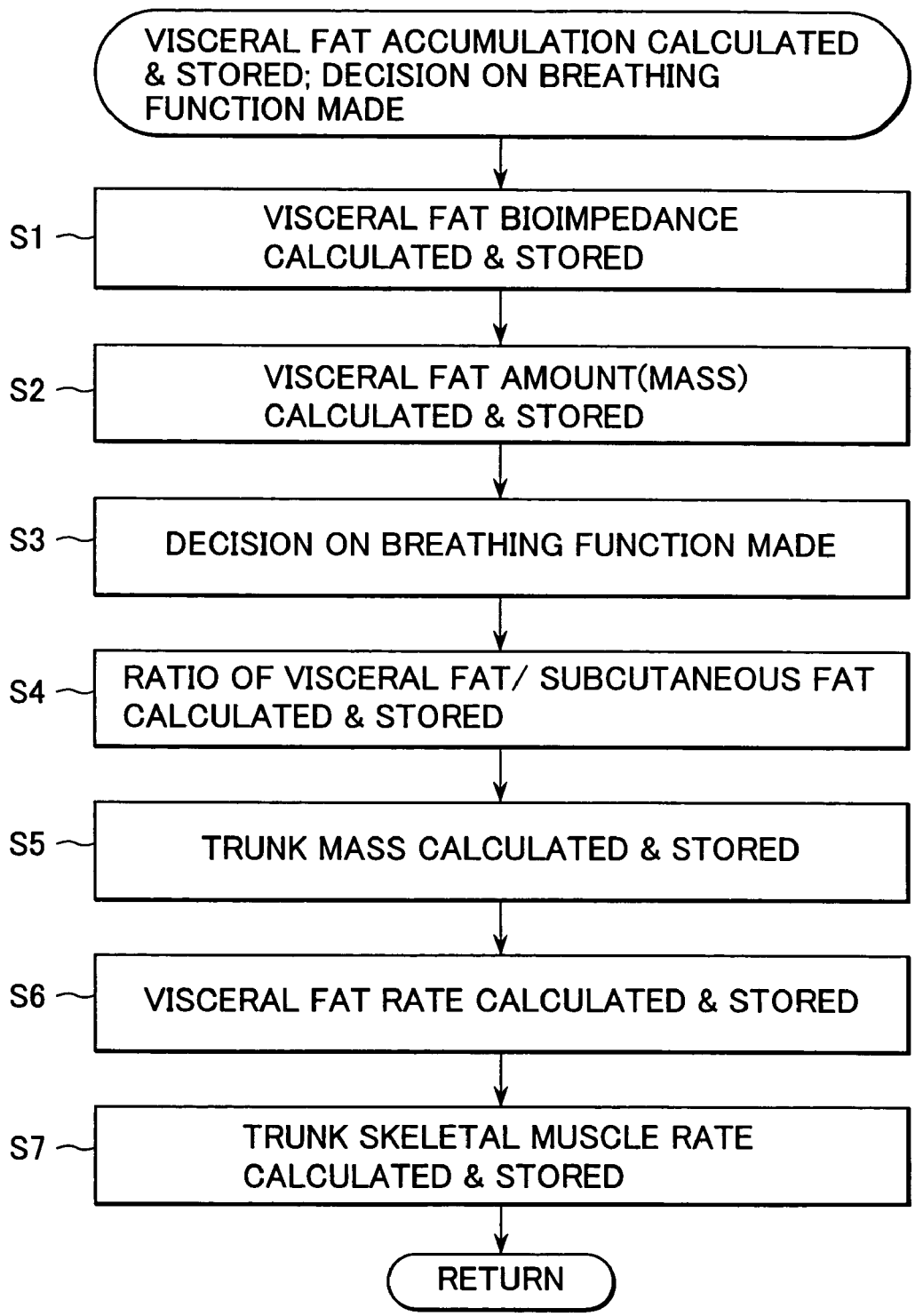

FIG. 31 is a subroutine flow chart depicting how EMBODIMENT 4 works in calculating and storing the information on the breathing function at a selected step in the main flow chart of FIG. 26; and FIG. 32 is a subroutine flow chart depicting how EMBODIMENT 4 works in calculating and storing the information on the visceral fat accumulation and making a decision on the breathing function at a selected step in the main flow chart of FIG. 26.

EMBODIMENT 1

Figure 1:
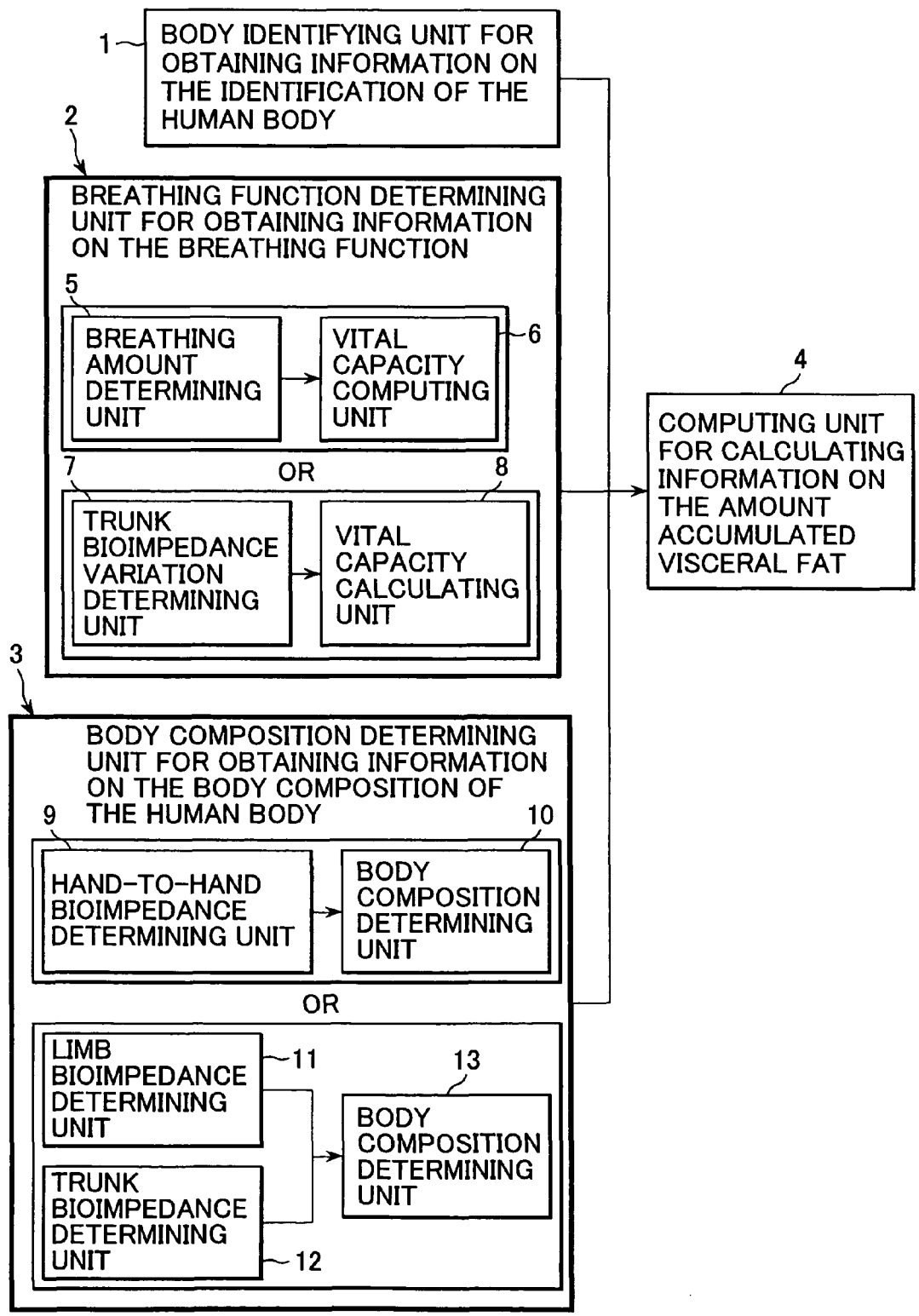
FIG. 1 is a function block diagram of an apparatus for assuming information on the amount accumulated visceral fat according to the present invention.
Figure 2A:
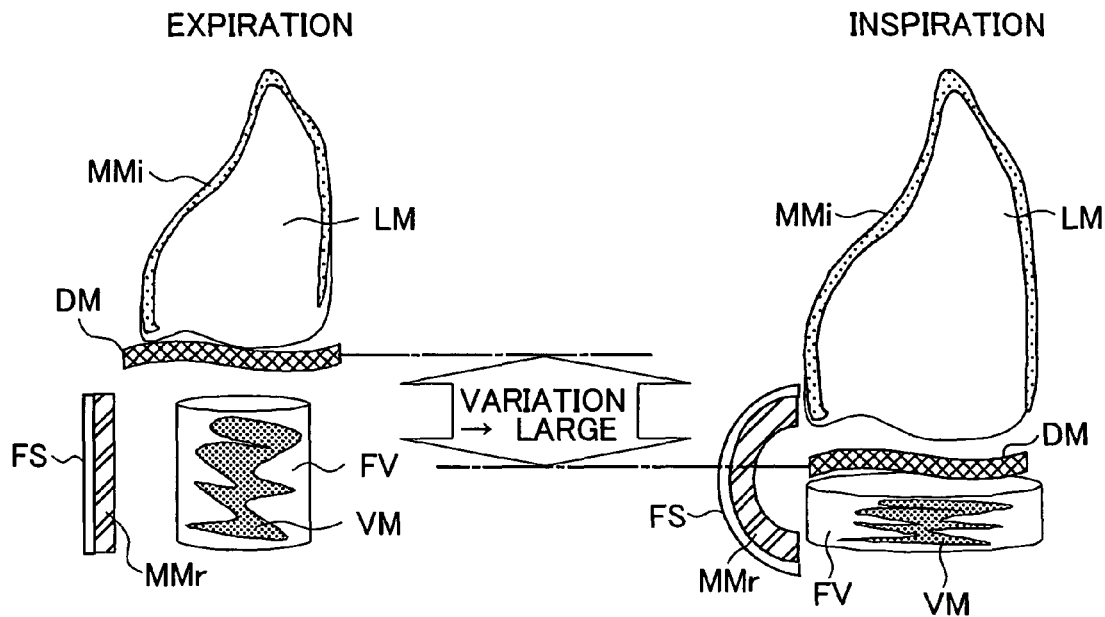
FIG. 2 illustrates how the trunk organs vary in response to breathing.
Figure 2B:
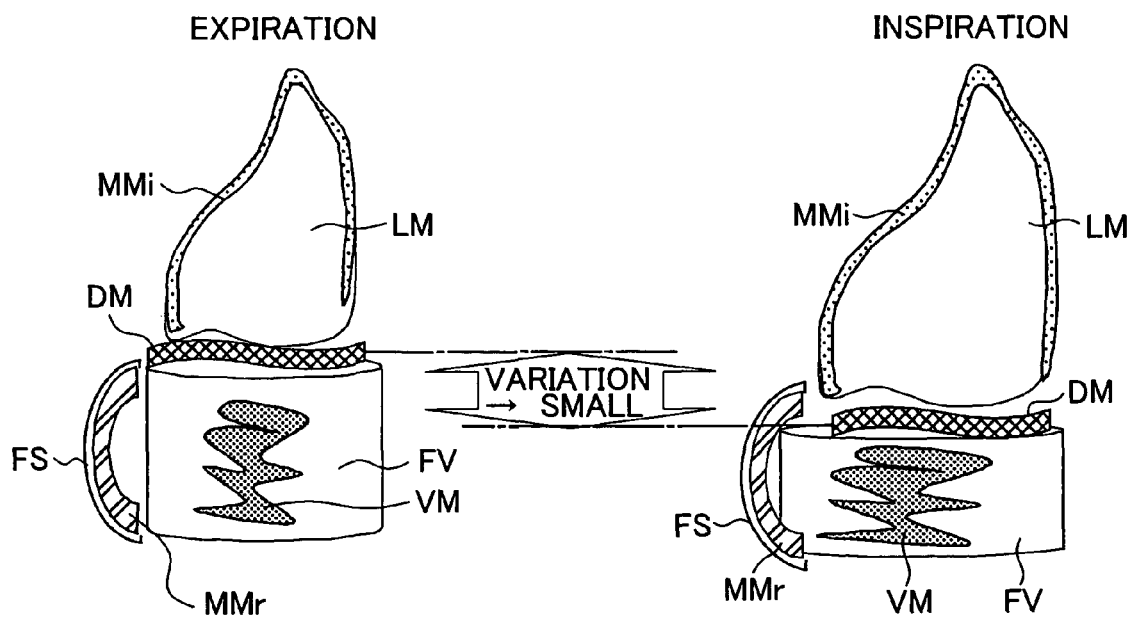
Figure 3:
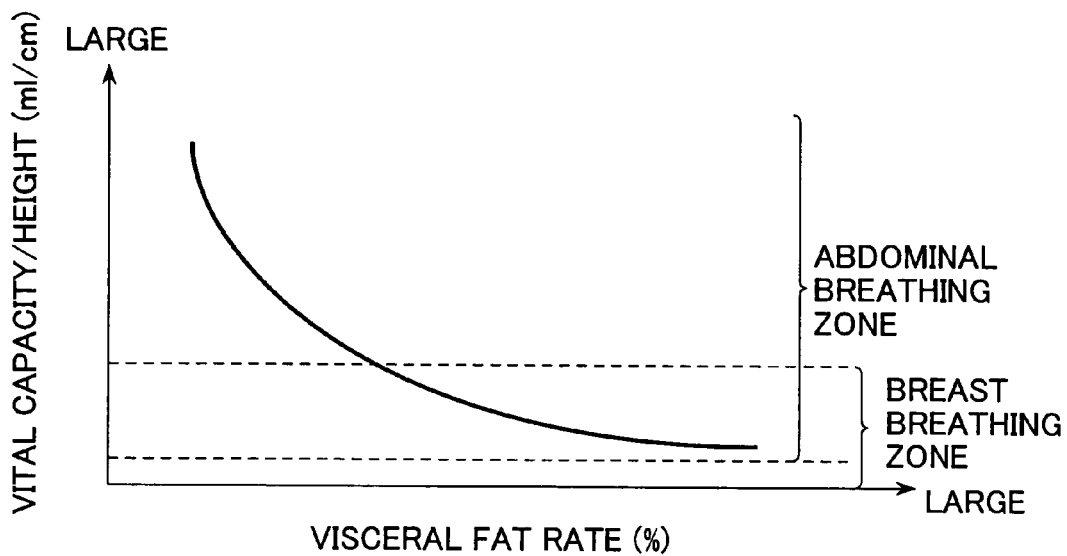
FIG. 3 is a graph of vital capacity/height against visceral fat rate.
Figure 4:
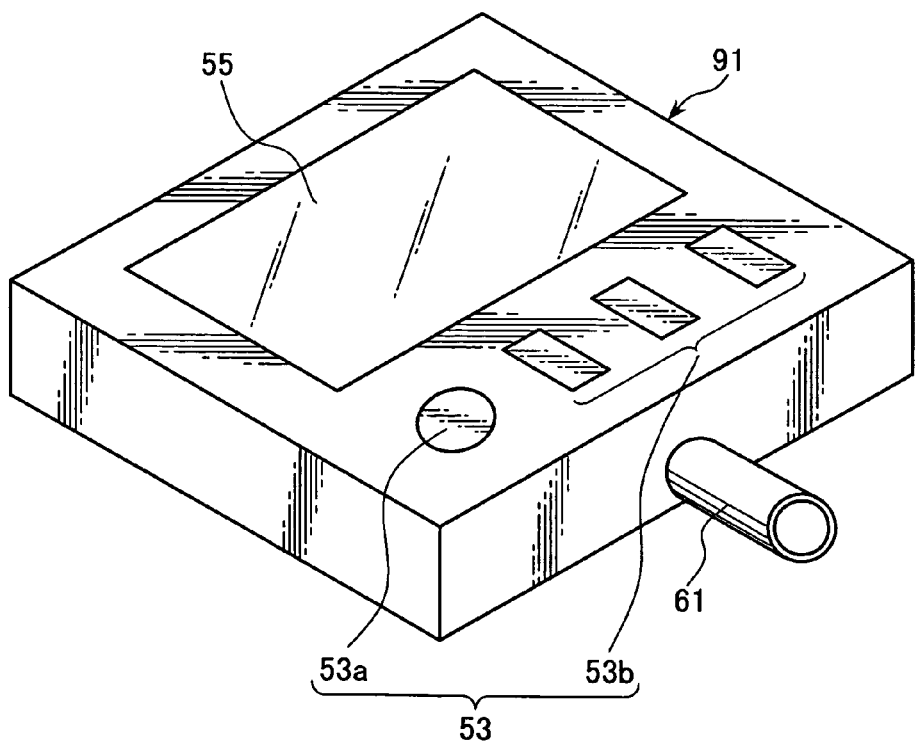
FIG. 4 is a perspective view of an apparatus for assuming information on the amount accumulated visceral fat according to EMBODIMENT 1 of the present invention.
Figure 5:
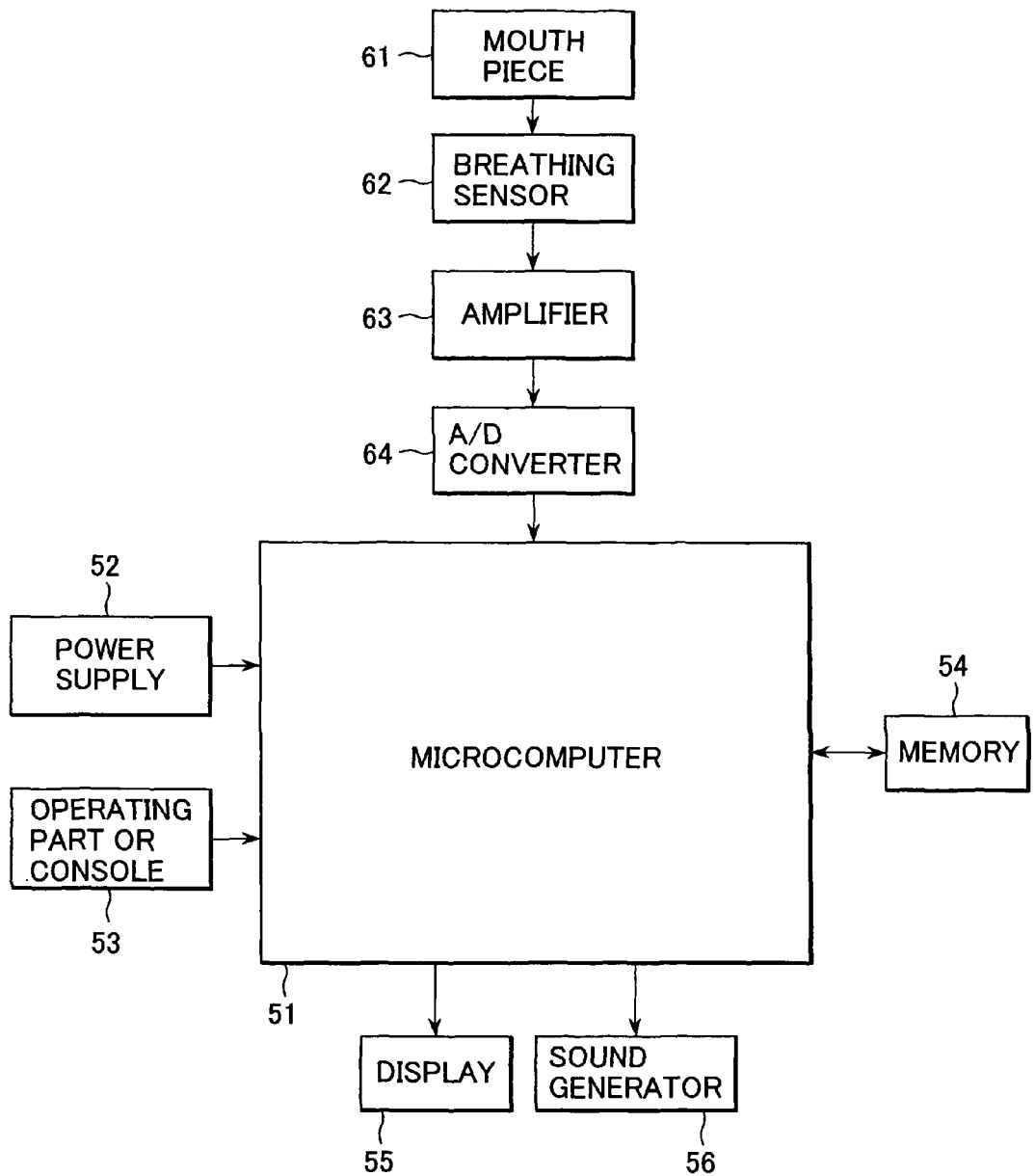
FIG. 5 is a structural block diagram of the apparatus for assuming information on the amount accumulated visceral fat of EMBODIMENT 1.

FIG. 4 is a perspective view of an apparatus for assuming information on the amount accumulated visceral fat according to EMBODIMENT 1 of the present invention, and FIG. 5 is a structural block diagram of the apparatus of FIG. 4, which comprises:
a body identifying unit for obtaining information on the identification of a human body; a breathing function determining unit for obtaining information on the breathing function, which comprises a breathing amount determining unit and a vital capacity calculating unit; and
a computing unit for calculating information on the amount accumulated visceral fat on the basis of the so obtained pieces of information on the identification of the human body and the breathing function.

Specifically the apparatus for assuming information on the amount accumulated visceral fat comprises a power supply 52, an operating part or console 53, a mouthpiece 61, a breathing sensor 62, an amplifier 63, an A/D converter 64, a memory 54, a display 55, a sound generator 63 and a microcomputer 51.

The power supply 52 provides the parts of the electric system with electricity.

The operating part or console 53 comprises a power key 53a for turning on or off the apparatus, and setting keys 53b for entering some pieces of information concerning selected features and attributes of a human body (such as sex, age, height and weight).

The mouthpiece 61 is a tube-like object through which one can take the air into one's lung and send out again via one's mouth.

The breathing sensor 62 detects the amount of the air that one takes into one's lung and send out again via the mouthpiece. More specifically the breathing sensor 62 may be of the type which can be used in detecting the pressure difference appearing across a resistive meshed screen, or may be of the flow-integration type, providing an analogue signal representing the amount of the air taken into one's lung and sent out again.

The amplifier 63 functions to amplify the analogue signal from the breathing sensor 62.

The A/D converter 64 functions to convert the analogue signal from the amplifier 63 to the corresponding digital signal.

The memory 54 stores at least the following pieces of information:
i) pieces of information concerning some identified features and attributes of the body (sex, age, height and weight), entered by using the operating part or console 53;
ii) the spirogram provided by sampling the breathing data, which are provided when the mouthpiece 61, breathing sensor 62, amplifier 63, A/D converter 64 and microcomputer 51 work all together;
iii) pieces of information on the breathing function (forced vital capacity, standard vital capacity, one-second-forced expiratory volume, one-second-forced expiratory volume % rate, vital capacity/standard vital capacity percent); information on the amount accumulated visceral fat (visceral fat rate) and body mass index (BMI), all provided by the microcomputer 51 as later described in detail.

The display 55 shows at least following pieces of information concerning:
i) the breathing guidance the microcomputer 51 provides under control, as later described;
ii) remeasurement in response to any abnormal condition perceived in measuring the breathing amount by the microcomputer 51, as later described;
iii) the breathing function (forced vital capacity, standard vital capacity, one-second-forced expiratory volume, one-second-forced expiratory volume % rate, vital capacity/standard vital capacity percent), the visceral fat accumulation (visceral fat rate) and the body mass index, as later described;
iv) normal or abnormal condition perceived in measurement of the breathing function when determined by the microcomputer 51, as later described.

The sound generator 56 comprises a buzzer responsive to at least following pieces of information for producing different sounds:
i) information on the breathing guidance controlled by the microcomputer 51, as later described;
ii) information on remeasurement in response to any abnormal condition perceived in measuring the breathing amount by the microcomputer 51, as later described;
iii) information of normal or abnormal condition detected by the microcomputer 51 in measuring the breathing function (one-second-forced expiratory volume % rate, vital capacity/standard vital capacity percent), as later described.

The microcomputer 51 comprises a CPU, a ROM for storing control and operation programs, a RAM for temporarily storing the results of the arithmetic operation and the determinations and decisions, a timer, I/O ports and others. The so constructed microcomputer 51 functions to:
perform required arithmetic operations for obtaining pieces of information concerning the breathing function (forced vital capacity, standard vital capacity, one-second-forced expiratory volume, one-second-forced expiratory volume % rate, vital capacity/standard vital capacity percent), visceral fat accumulation (visceral fat rate) and body mass index;

make a decision as to whether the condition is normal or abnormal in measurement, and as to whether the information on the breathing function indicates normal or abnormal condition;

provide data representing the breathing amount (data being sampled for spirogram); and produce vocal messages informing the user of all required pieces of information.

The software programs for determining the breathing function (forced vital capacity, standard vital capacity, one-second-forced expiratory volume, one-second-forced expiratory volume % rate, vital capacity/standard vital capacity percent), visceral fat accumulation (visceral fat rate) and body mass index are stored in the memory 54:

$$VC(\text{or FVC}) = VLM\text{max} - VLM\text{min} \quad (1)$$

$$VC0 = H \times (am \times \text{Age} + bm) \quad (2a)$$

$$VC0 = H \times (af \times \text{Age} + bf) \quad (2b)$$

$$VC\% = VC/VC0 \times 100 \quad (3)$$

$$FEV1.0 = VLM\text{max} - VLM1s \quad (4)$$

$$FEV1.0\% = FEV1.0/FVC \times 100 \quad (5)$$

$$\%VFat = aam \times VC/H + bbm \times \text{Age} + ccm \times W + ddm \quad (6a)$$

$$\%VFat = aaf \times VC/H + bbf \times \text{Age} + ccf \times W + ddf \quad (6b)$$

$$BMI = W/H^2 \quad (7)$$

VC: vital capacity
FVC: forced vital capacity
VC0: standard vital capacity
VC %: vital capacity/standard vital capacity percent
FEV1.0: one-second-forced expiratory volume
FEV1.0%: one-second-forced expiratory volume % rate
% VFat: visceral fat rate
BMI: body mass index
VLMmax: maximum inspiration value
VLMmin: maximum expiration value
VLM1s: one-second-post-expiratory value
H: height
Age: age
W: weight
am: −0.112 in this particular example
bm: 27.63 in this particular example
aam, bbm, ccm and ddm: constants for male
af: −0.101 in this particular example
bf: 21.78 in this particular example
aaf, bbf, ccf, ddf: constants for female As regards a decision to be made as to whether the normal or abnormal condition is reached in obtaining pieces of information on the breathing function: if FEV1.0%≧70%, and concurrently FVC %≧80%, the condition is normal, and otherwise, the condition is abnormal.

The operating part or console 53, the memory 54, the microcomputer 51 and the power supply 52 make up the body identifying unit for obtaining information on the identification of the human body. The mouthpiece 61, the breathing sensor 62, the amplifier 63, the A/D converter 64, the memory 54, the microcomputer 51 and the power supply 52 make up the breathing function determining unit for obtaining information on the breathing function. The memory 54, the microcomputer 51 and the power supply 52 make up the vital capacity computing unit and the computing unit for calculating information on the amount accumulated visceral fat.

Figure 6:
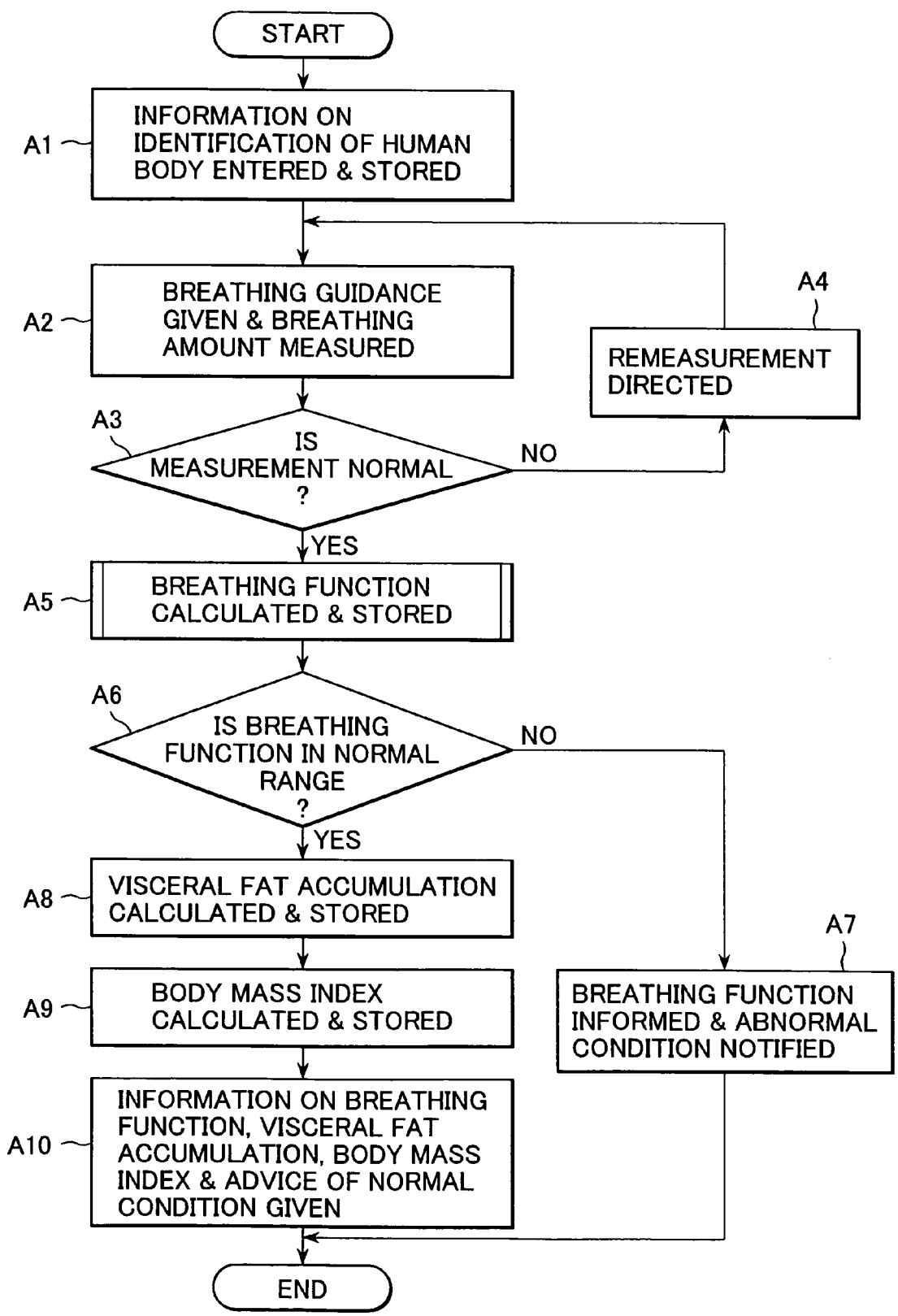
FIG. 6 is a main flow chart depicting how the apparatus for assuming information on the amount accumulated visceral fat of EMBODIMENT 1 works.
Figure 7:
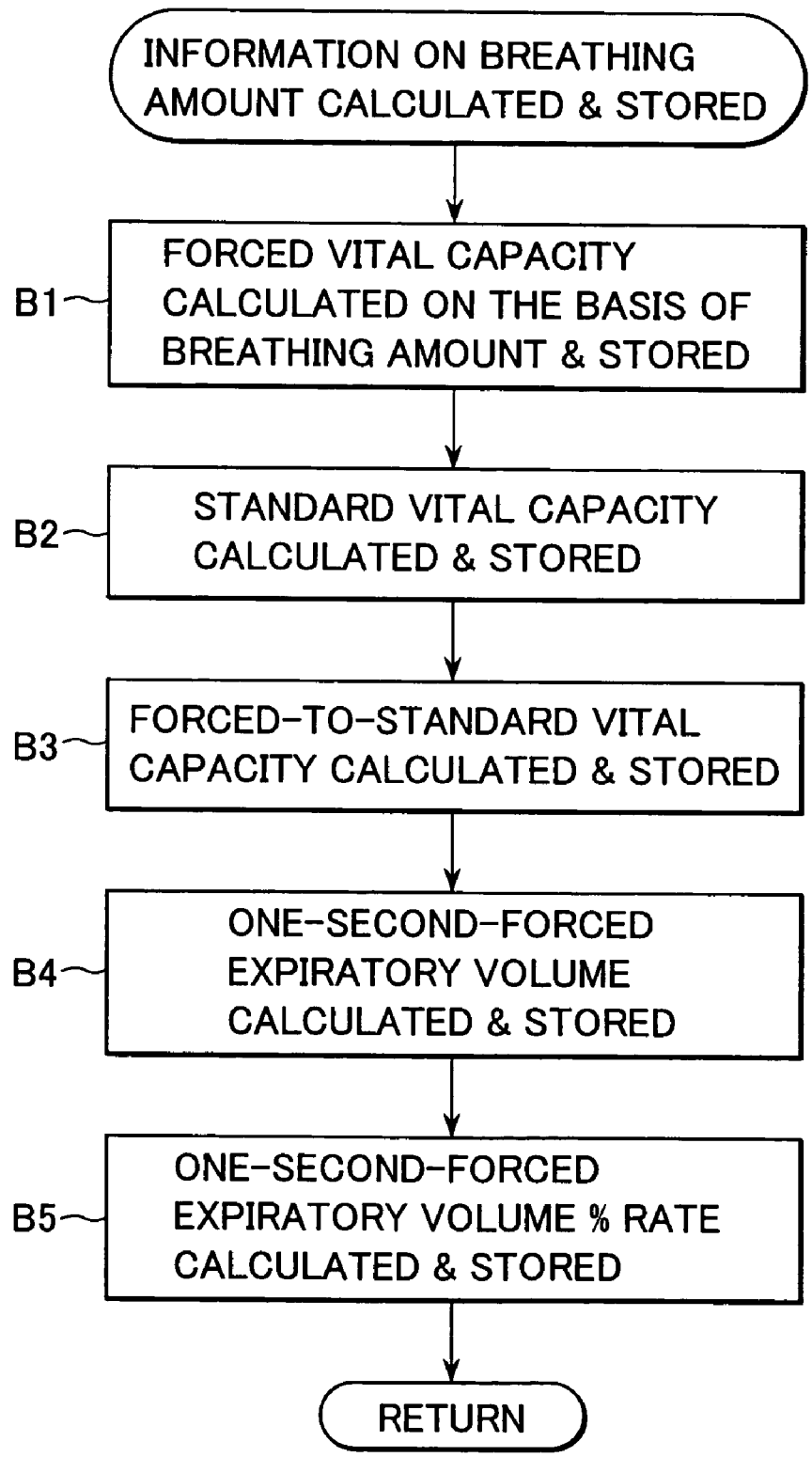
FIG. 7 is a subroutine flow chart depicting how the visceral fat accumulation assuming apparatus of EMBODIMENT 1 works in calculating and storing the information on breathing function at a selected step in the main flow chart of FIG. 6.

FIG. 6 shows a main flowchart and FIG. 7 shows a subroutine flowchart. Referring to these figures, the manner in which the apparatus for assuming information on the amount accumulated visceral fat according to EMBODIMENT 1 works is described below.

First, referring to FIG. 6, at the outset the power supply key 53a turns on, allowing the power supply 52 to supply the parts of the electrical system with electricity, thus permitting the entering of the information on the identification of the human body (sex, age, height and weight). The setting key 53b is depressed to enter these pieces of information into the memory 54 (step A1).

When the breathing amount determining unit is put in stand-by position, the display 55 and the sound generator 56 provide the following breathing guidance, which is retrieved from the ROM, as in the well known spirotest:

"Procedure 1: Pinch your nose with a clamp, and hold the mouthpiece 61 in your mouth";

"Procedure 2: Breath several times naturally";

"Procedure 3: Take into your lungs as much air as you can at the exact rate or timing directed from the sound generator"; and "Procedure 4: Take the air into your lungs and send it out completely as quickly as you can at the exact rate or timing directed from the sound generator".

Figure 8:
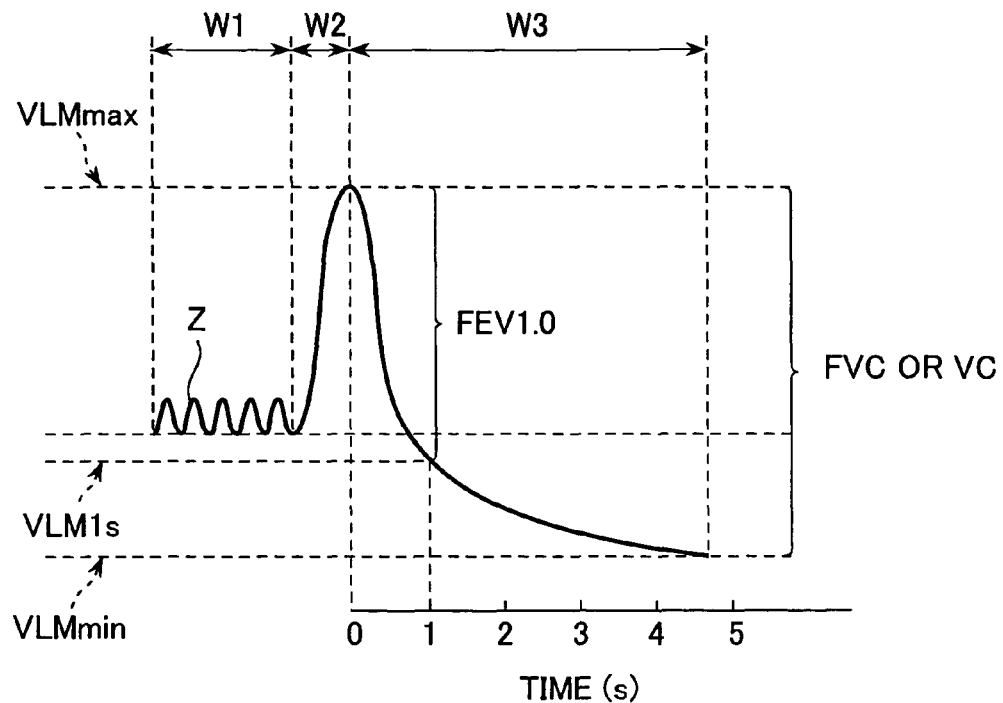
FIG. 8 is a spirogram plotted in EMBODIMENT 1.

At every step of procedure a buzzing sound is produced. Then, the breathing amount measurement starts, plotting a spirogram (breathing curve) Z as shown in FIG. 8 (step A2). In the spirogram W1 stands for the sampling period for which the above Procedure 2 continues; W2 stands for the sampling period for which the above Procedure 3 continues; and W3 stands for the sampling period for which the above Procedure 4 continues.

Then, the microcomputer 51 makes a decision as to whether the measurement is being carried out in good or bad condition, more specifically whether or not the measurement exactly follows the breathing guidance (step A3).

When it is decided that the measurement is not carried out in good condition ("NO" at step A3), the display 55 shows the notification of remeasurement which reads "The measurement was wrongly carried out. Please perform another measurement." and the sound generator produces the buzzing sound (step A4), and the proceeding returns to step A2.

On the contrary, when it is decided that the measurement is being conducted in good condition ("YES" at step A3), the microcomputer 51 performs a required arithmetic operation on the information concerning breathing function (forced vital capacity, standard vital capacity, one-second-forced expiratory volume, one-second-forced expiratory volume % rate, vital capacity/standard vital capacity percent) and stores the results of the arithmetic operation (step A5).

Then, the microcomputer 51 makes a decision as to whether or not the results of the breathing function measurement are satisfactory, specifically whether or not one-second-forced expiratory volume % rate (FEV1.0%), and vital capacity/standard vital capacity percent (FVC %) remain in the normal range (FEV1.0%≧70%, and FVC %≧80%) (step A6).

In case that one-second-forced expiratory volume % rate and vital capacity/standard vital capacity percent are out of the normal range ("NO" at step A6), the display 55 shows, along with the pieces of information on breathing function (forced vital capacity, standard vital capacity, one-second-forced expiratory volume, one-second-forced expiratory volume % rate, vital capacity/standard vital capacity percent) stored in the memory 54, the abnormal condition notifying message retrieved from the ROM, which reads "There is the fear of obstructive impairment. Be careful."; "There is the fear of bridle impairment. Be careful."; or "There is the fear of combined impairment. Be careful." At the same time, the sound generator 56 produces an extra buzzing sound (two dot-and-one dash sound combination) prestored in the ROM to inform the user of the arising of the abnormal condition (step A7), thus finishing a series of procedure steps.

In case that one-second-forced expiratory volume % rate and vital capacity/standard vital capacity percent remain within the normal range ("YES" at step A6), the microcomputer 51 calculates the visceral fat rate according to the equation (6a) or (6b) by using the pieces of information on identification of the human body (age, height and weight) and those on the breathing function (forced vital capacity), which are retrieved from the memory 54 for substitution. The results of the so calculated visceral fat rate are stored in the memory 54 (step A8). The equation (6a) is applied to males whereas the equation (6b) is applied to females. The vital capacity (VC) comprehends the forced vital capacity (FVC) in significance, and therefore the latter variable (FVC) can be used as a substitute for the former (VC) in either equation.

Then, the microcomputer 51 calculates the body mass index according to the equation (7) in terms of the pieces of information on the identification of the human body (age and weight), which are retrieved from the memory 54 for substitution. The results of the so calculated body mass index are stored in the memory 54 (step A9).

The display 55 shows the pieces of information on breathing function (forced vital capacity, standard vital capacity, vital capacity/standard vital capacity percent, one-second-forced expiratory volume, one-second-forced expiratory volume % rate) retrieved from the memory 54 and the notification of the normal condition retrieved from the ROM, which reads "Your breathing (lung) function is normal." At the same time the sound generator 56 produces a buzzing sound (two-dot sound) prestored in the ROM (step A10). Thus, the apparatus for assuming information on the amount accumulated visceral fat is finished with a series of procedure steps.

Now, the sub-routine at step A5 (arithmetic operation and storage of the information on the breathing function in the main flow) is described below.

As shown in FIG. 7, first, the microcomputer 51 calculates the forced vital capacity (FVC) by substituting for the corresponding variables in the equation (1) the maximum inspiration and expiration values both appearing in the spirogram, which is already determined by the breathing amount determining unit. The so calculated forced vital capacity is stored in the memory 54 (step B1).

Then, the microcomputer 51 calculates the standard vital capacity (VC0) by substituting the pieces of information on the identification of the human body (age and weight) retrieved from the memory 54 for the corresponding variables in the equation (2a) or (2b), and the so calculated standard vital capacity is stored in the memory 54 (step B2). If the information on the identification of the human body is for males, the equation (2a) is used, and otherwise, the equation (2b) is used for females.

The microcomputer 51 calculates the vital capacity/standard vital capacity percent (VC %) by substituting the forced vital capacity (FVC) and the standard vital capacity (VC0) both retrieved from the memory 54 for the corresponding variables in the equation (3), and the so calculated vital capacity/standard vital capacity percent (VC %) is stored in the memory 54 (step B3). The vital capacity comprehends the forced vital capacity in significance, and therefore the latter variable can be used as a substitute for the former variable in the equation (3).

The microcomputer 51 calculates the one-second-forced expiratory volume (FEV1.0) by substituting the maximum inspiration value and the one-second post-expiratory value both appearing in the spirogram, which is determined by the breathing amount measuring unit, for the corresponding variables in the equation (4), and the so calculated one-second-forced expiratory volume is stored in the memory 54 (step B4).

The microcomputer 51 calculates the one-second-forced expiratory volume % rate (FRV1.0%) by substituting the one-second-forced expiratory volume (FEV1.0) and the forced vital capacity (FVC) both retrieved from the memory for the corresponding variables in the equation (5), and the so calculated one-second-forced expiratory volume % rate is stored in the memory 54 (step B5), thus completing the sub-routine.

The apparatus for assuming information on the amount accumulated visceral fat according to EMBODIMENT 1 works as described above.

The apparatus for assuming information on the amount accumulated visceral fat is so constructed that it may collect pieces of information on the identification of the human body such as sex, age, height and weight, and on the breathing function such as the forced vital capacity, and may sure determine the visceral fat rate easily with a high degree of accuracy.

In EMBODIMENT 1 the information on the identification of the human body includes sex, age, height and weight to determine the visceral fat rate according to the equation (6a) or (6b). To improve the accuracy even more pieces of information of the physical shape and size (at least any one of the upper limb length, lower limb length, trunk length and abdominal circumference) may be collected and used for better identification of the human body. These constants are multiplied by some coefficients, and the quantities are substituted for the independent variables in the equation (6a) or (6b). Then, a visceral fat rate can be provided at a still higher degree of accuracy.

EMBODIMENT 2

Figure 9:
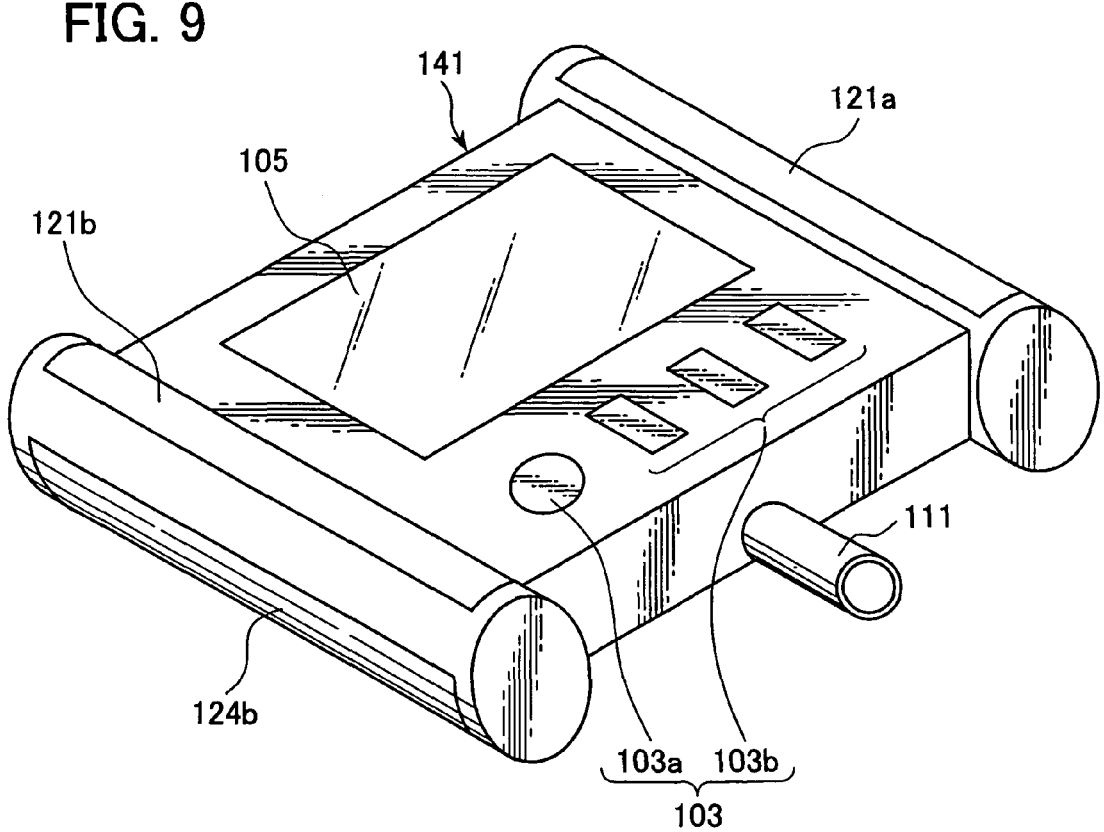
FIG. 9 is a perspective view of an apparatus for assuming information on the amount accumulated visceral fat according to EMBODIMENT 2 of the present invention.
Figure 10:
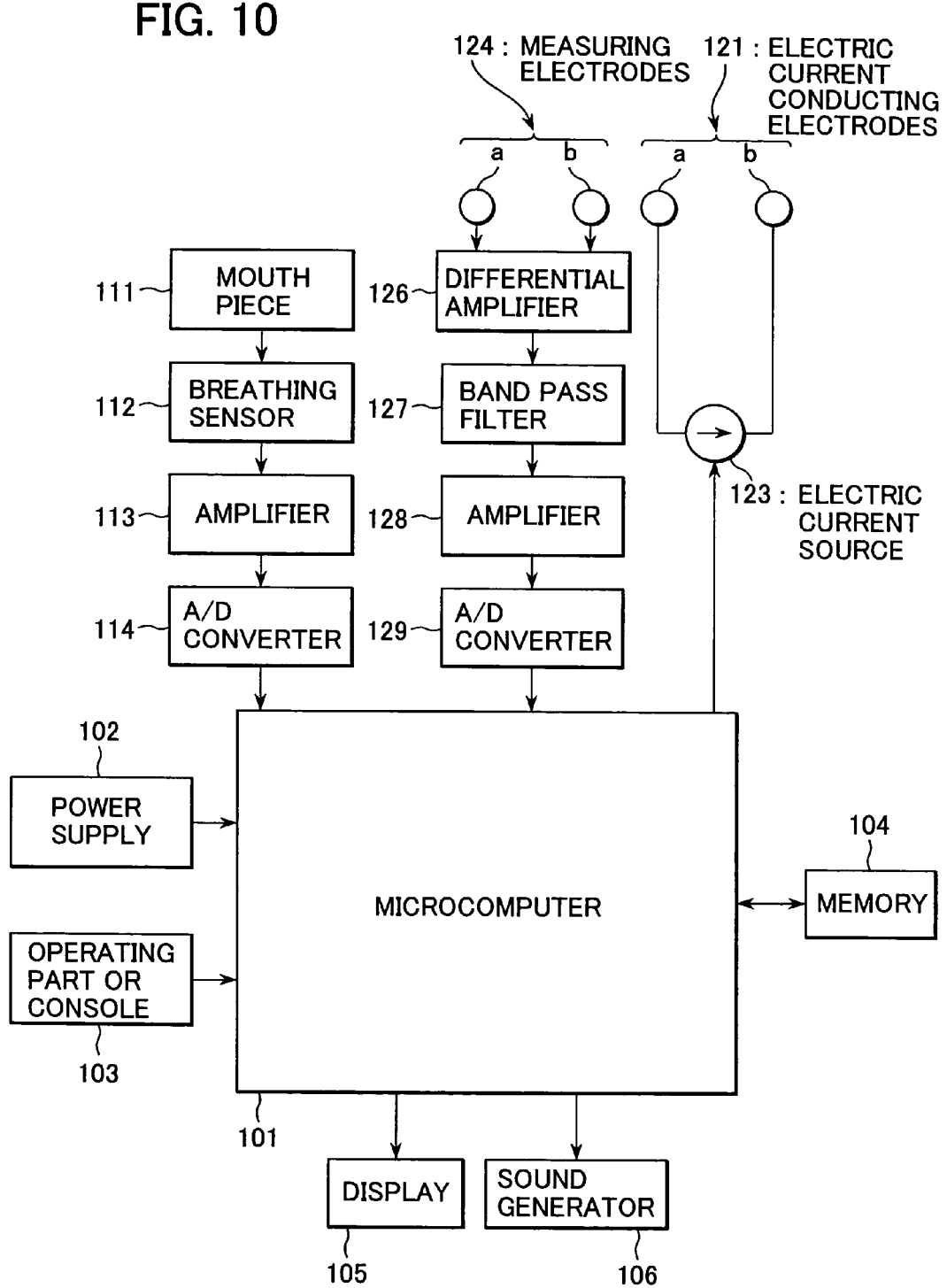
FIG. 10 is a structural block diagram of the apparatus for assuming information on the amount accumulated visceral fat of EMBODIMENT 2.

FIG. 9 is a perspective view of an apparatus for assuming information on the amount accumulated visceral fat according to EMBODIMENT 2 of the present invention, and FIG. 10 is a structural block diagram of the apparatus of FIG. 9, which comprises:
a body identifying unit for obtaining information on the identification of a human body; a breathing function determining unit for obtaining information on the breathing function, which comprises a breathing amount determining unit and a vital capacity calculating unit;
a body composition determining unit for obtaining information on the body composition of the human body, which comprises a hand-to-hand bioimpedance determining unit and a body composition calculating unit; and
a computing unit for calculating information on the amount accumulated visceral fat on the basis of the so obtained pieces of information on the identification of the human body, the breathing function and the body composition.

Specifically the apparatus for assuming information on the amount accumulated visceral fat according to EMBODIMENT 2 comprises a power supply 102, an operating part or console 103 (103a and 103b), a mouthpiece 111, a breathing sensor 112, a pair of electric current conducting electrodes 121 (121a and 121b), a pair of measuring electrodes 124 (124a and 124b), a differential amplifier 126, a band pass filter or BPF 127, an electric current source 123, amplifiers 113 and 128, A/D converters 114 and 129, a memory 104, a display 105, a sound generator 106 and a microcomputer 101. All of these units and parts are packaged in the housing 141. More specifically, the display 105 and the operating part or console 103 are arranged on the top surface of the housing 141; one of the paired electric current conducting electrodes 121b and one of the paired measuring electrodes 124b are arranged on the left side of the housing 141 whereas the other electric current conducting electrode 121a and the other measuring electrode 124a are arranged on the right side of the housing 141; and the mouthpiece 111 is arranged on the front side of the housing 141. The remaining units and parts are arranged inside.

The power supply 102, operating part or console 103, mouthpiece 111, breathing sensor 112, amplifier 113 and A/D converter 114 are similar to the power supply 52, operating part or console 53, mouthpiece 61, breathing sensor 62, amplifier 63 and A/D converter 64 in EMBODIMENT 1.

The pair of electric current conducting electrodes 121 (121a and 121b) are used in making an electric current flow from hand to hand, and the pair of measuring electrodes 124 (124a and 124b) are used to detect the potential difference appearing between both hands The differential amplifier 126 detects the potential difference appearing between the paired measuring electrodes.

The band pass filter 127 allows a required component of the signal detected by the differential amplifier 126 to pass through The electric current source 123 supplies both hands with an electric current under the control of the microcomputer 101.

The amplifier 128 amplifies the analogue signal from the band pass filter 127.

The A/D converter 129 converts the analogue signal from the amplifier 128 into the corresponding digital signal.

The memory 104 stores at least the following pieces of information:
i) pieces of information concerning some identified features and attributes of the body (sex, age, height and weight), entered by using the operating part or console 103;
ii) hand-to-hand bioimpedance determined by using the measuring electrodes 124 (124a and 124b), differential amplifier 126, band pass filter 127, amplifier 128, A/D converter 129 and microcomputer 101;
iii) the spirogram provided by sampling the breathing data, which are provided when the mouthpiece 111, breathing sensor 112, amplifier 113, A/D converter 114 and microcomputer 101 work all together;
iv) pieces of information on the body composition (fat-free mass, body fat rate, trunk skeletal muscle rate), the body mass index, the breathing function (forced vital capacity, standard vital capacity, vital capacity/standard vital capacity percent, one-second-forced expiratory volume, and one-second-forced expiratory volume % rate); and the visceral fat accumulation (visceral fat rate), all provided by the microcomputer 101 as later described in detail.

The display 105 shows at least following pieces of information concerning:
i) the breathing guidance which the microcomputer 51 provides under control, as later described;
ii) remeasurement in response to any abnormal condition perceived in measuring the breathing amount by the microcomputer 101, as later described;
iii) the body composition (fat-free mass, body fat rate, trunk skeletal muscle rate), the body mass index, the breathing function (forced vital capacity, standard vital capacity, vital capacity/standard vital capacity percent, one-second-forced expiratory volume, and one-second-forced expiratory volume % rate) and the visceral fat accumulation (visceral fat rate)
iv) notification of the normal condition when the microcomputer 101 determines that the breathing function (in terms of one-second-forced expiratory volume % rate and vital capacity/standard vital capacity percent) is in the normal condition, and notification of the abnormal condition when the microcomputer determines as such, as later described; and
v) notification of finishing the measurement after the hand-to-hand bioimpedance is determined by the hand-to-hand bioimpedance determining unit and the so determined bioimpedance is stored in the memory 104.

The sound generator 106 comprises a buzzer responsive to at least following pieces of information for producing different sounds:
i) information on the breathing guidance controlled by the microcomputer 101, as later described;
ii) information on remeasurement in response to any abnormal condition perceived by the microcomputer 101 in measuring the breathing amount, as later described;
iii) notification of normal or abnormal condition detected by the microcomputer 101 in measuring the breathing function (in terms of one-second-forced expiratory volume % rate and vital capacity/standard vital capacity percent), as later described; and
iv) notification of finishing the measurement after the hand-to-hand bioimpedance is determined by the hand-to-hand bioimpedance determining unit and the so determined bioimpedance is stored in the memory 104.

The microcomputer 101 comprises a CPU, a ROM for storing control and operation programs, a RAM for temporarily storing the results of the arithmetic operation and the determinations and decisions, a timer, I/O ports and others. The so constructed microcomputer 101 functions to
perform required arithmetic operations for obtaining pieces of information concerning the body composition (fat-free mass, body fat rate, trunk skeletal muscle rate), the body mass index, the breathing function (forced vital capacity, standard vital capacity, vital capacity/standard vital capacity percent, one-second-forced expiratory volume, and one-second-forced expiratory volume % rate) and the visceral fat accumulation (visceral fat rate);
make a decision as to whether the condition is normal or abnormal in measurement, and as to whether the information on the breathing function indicates normal or abnormal condition;
determine hand-to-hand bioimpedance, and provide data representing the breathing amount (data being sampled for spirogram); and
producing vocal messages informing the user of all required pieces of information.

The software program for determining the body composition (fat-free mass, body fat rate, trunk skeletal muscle rate) contains the following arithmetic operation:

$$LBM = a1 \times H^2/Zm + b1 \times W + c1 \times Age + d1 \quad (8)$$

$$\% Fat = (W - LBM)/W \times 100 \quad (9)$$

$$\% MM = a2 \times LBM + b2 \quad (10)$$

LBM: fat-free mass (lean body mass);
% Fat: body fat rate;
% MM: trunk skeletal muscle rate;
H: height;

W: weight;
Age: age; and
Zm: hand-to-hand bioimpedance
a1, b1, c1, d1, a2, and b2: constants The body mass index and the pieces of information on breathing function (forced vital capacity, standard vital capacity, vital capacity/standard vital capacity percent, one-second-forced expiratory volume, and one-second-forced expiratory volume % rate) can be calculated according to equations (1), (2a), (2b), (3), (4), (5) and (7) as in EMBODIMENT 1.

The information on the visceral fat accumulation (visceral fat rate) can be calculated according to the following equations, which are stored as operation programs:

$$\%VFat = aam \times VC/H + bbm \times Age + ccm \times W + ddm \times \%MM + eem \quad (11a)$$

$$\%VFat = aaf \times VC/H + bbf \times Age + ccf \times W + ddf \times \%MM + eef \quad (11b)$$

% VFat: visceral fat rate
VC: vital capacity
H: height
Age: age
W: weight
% MM: trunk skeletal muscle rate;
aam, bbm, ccm, ddm, eem: constants for male
aaf, bbf, ccf, ddf, eef: constants for female As regards a decision to be made as to whether the normal or abnormal condition is reached in obtaining pieces of information on the breathing function: if FEV1.0%≧70%, and concurrently FVC %≧80%, the condition is normal, and otherwise, the condition is abnormal.

The operating part or console 103, the memory 104, the microcomputer 101 and the power supply 102 make up the body identifying unit for obtaining information on the identification of the human body. The mouthpiece 111, the breathing sensor 112, the amplifier 113, the A/D converter 114, the memory 104, the microcomputer 101 and the power supply 102 make up the breathing function determining unit for obtaining information on the breathing function. The electric current conducting electrodes 121 (121a and 121b), the measuring electrodes 124 (124a and 124b), the differential amplifier 126, the band pass filter 127, the current source 123, the amplifier 128, the A/D converter 129, the memory 104, the microcomputer 101 and the power supply 102 make up the hand-to-hand bioimpedance determining unit. Finally, the memory 104, the microcomputer 101 and the power supply 102 make up the body composition determining unit for obtaining information on the body composition of the human body, the vital capacity computing unit for calculating information on the breathing function and the computing unit for calculating information on the amount accumulated visceral fat.

Figure 11:
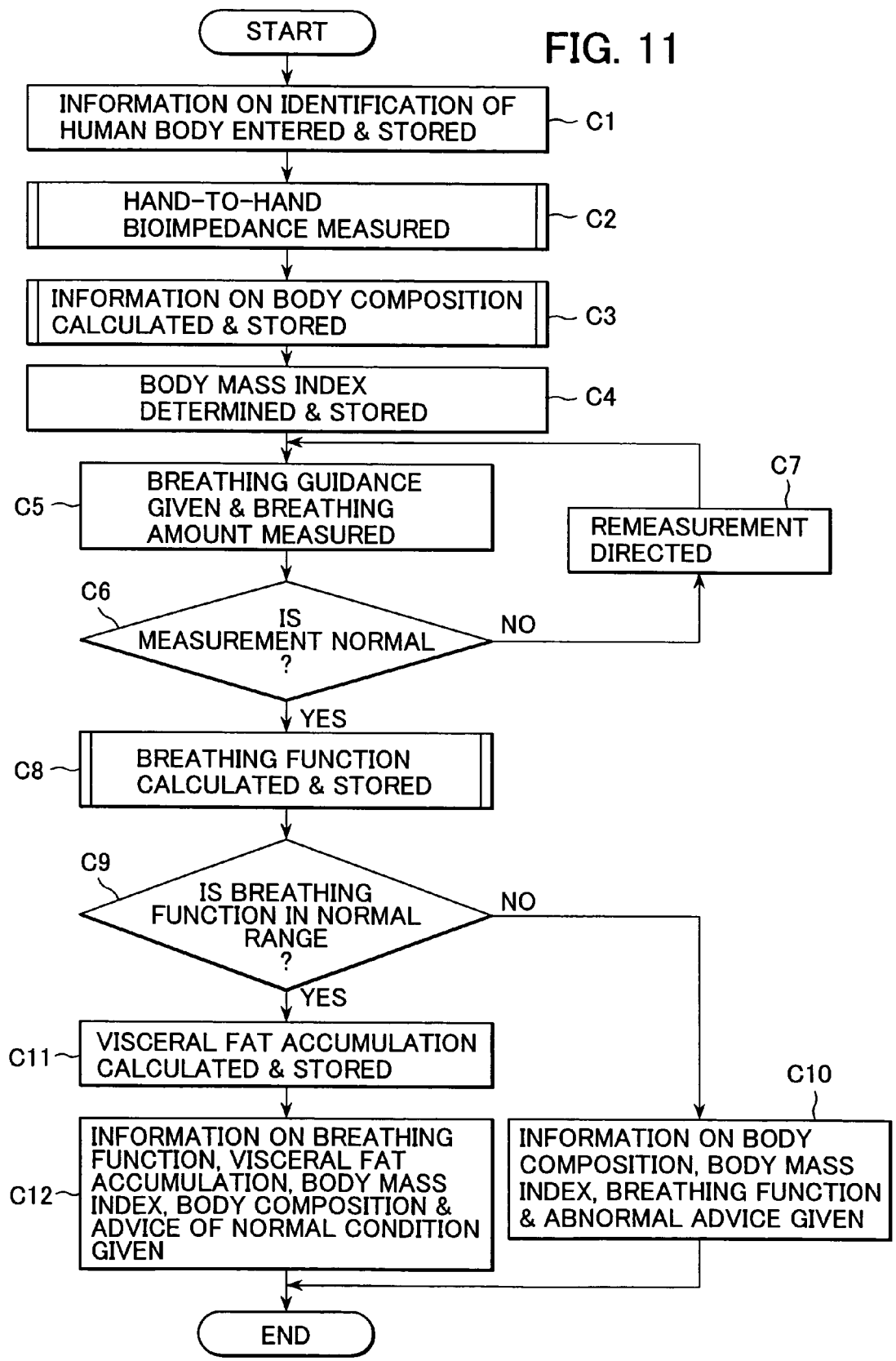
FIG. 11 is a main flow chart depicting how the apparatus for assuming information on the amount accumulated visceral fat of EMBODIMENT 2 works.
Figure 12:
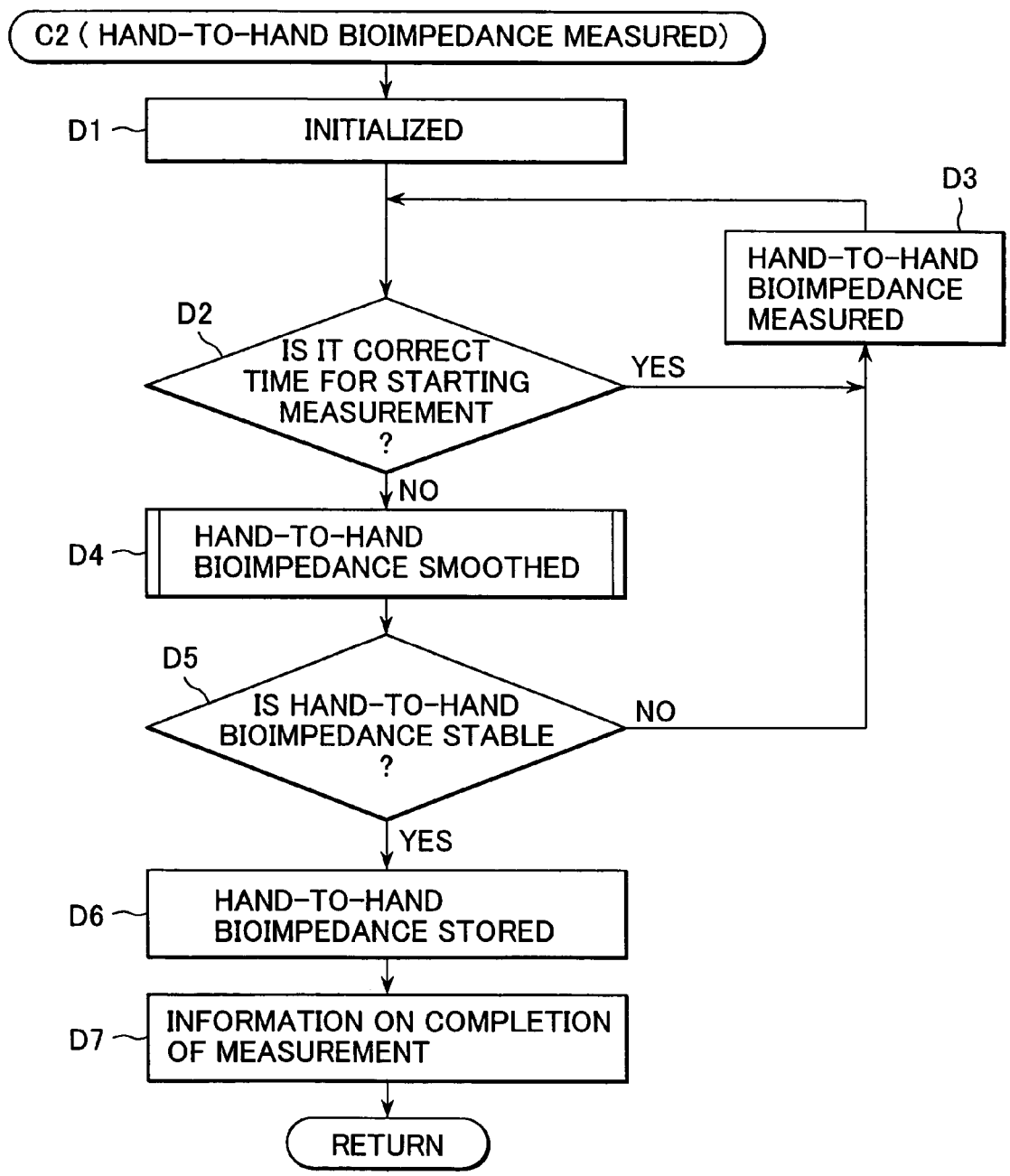
FIG. 12 is a subroutine flow chart depicting how the apparatus for assuming information on the amount accumulated visceral fat of EMBODIMENT 2 works in determining a hand-to-hand bioimpedance at a selected step in the main flow chart of FIG. 11.
Figure 13:
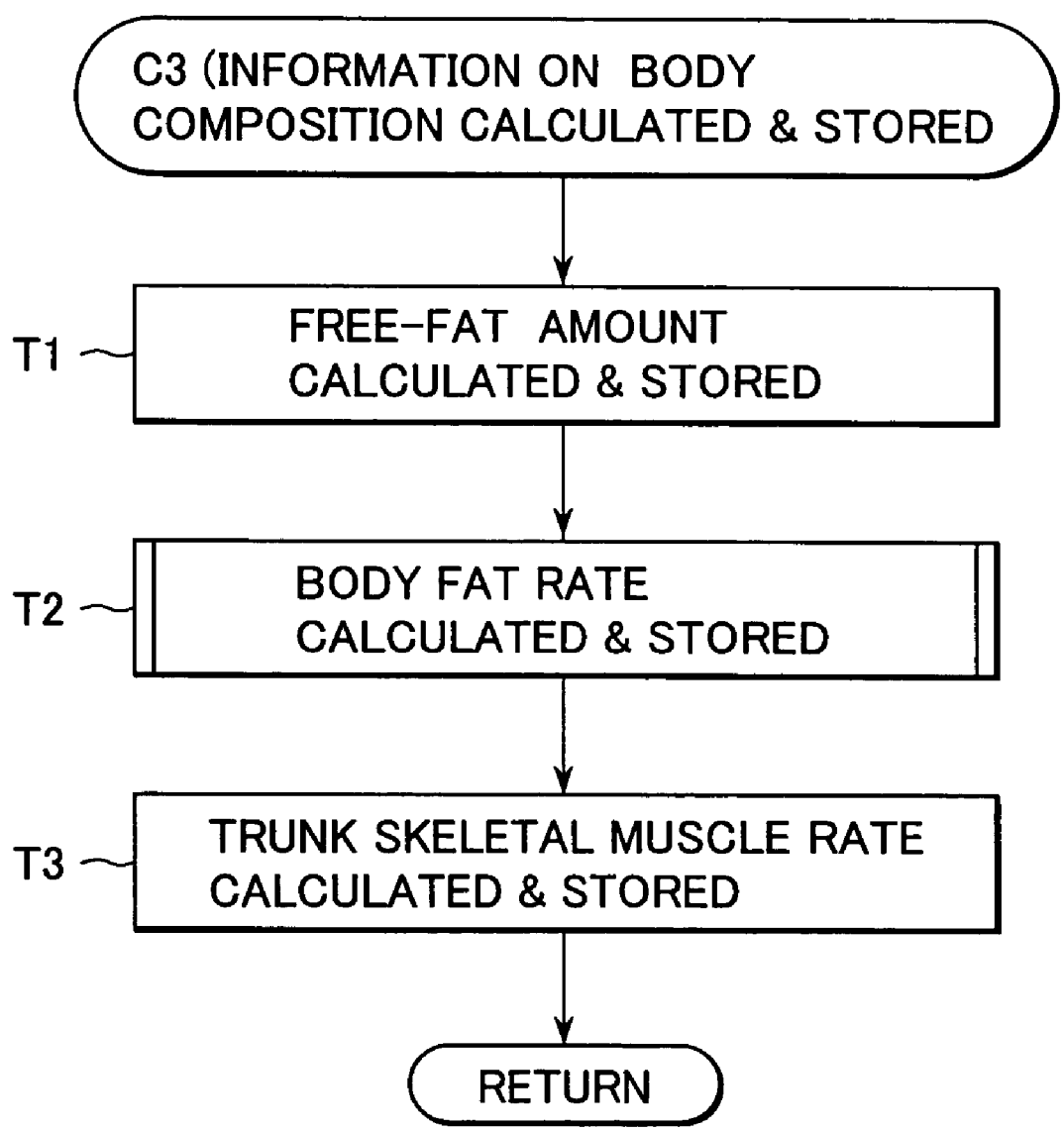
FIG. 13 is a subroutine flow chart depicting how EMBODIMENT 2 works in calculating and storing the information on the body composition at a selected step in the main flow chart of FIG. 11.

FIG. 11 shows a main flowchart and FIGS. 12 and 13 show sub-routine flowcharts. Referring to these figures, the manner in which the apparatus for assuming information on the amount accumulated visceral fat according to EMBODIMENT 2 works is described below.

First, referring to FIG. 11, at the outset the power supply key 103a turns on, allowing the power supply 102 to supply the parts of the electrical system with electricity, thereby permitting the entering of the information on the identification of the human body (sex, age, height and weight). The setting key 103b is depressed to enter these pieces of information into the memory 104 (step C1).

The hand-to-hand bioimpedance is determined by the hand-to-hand bioimpedance determining unit, as later described (step C2).

Then, the microcomputer 101 calculates the pieces of information on the body composition (fat-free mass, body fat rate, trunk skeletal muscle rate), and the so calculated pieces of information are stored in the memory 104 (step C3).

The microcomputer 101 determines the body mass index by substituting the information on the identification of the human body (sex, age, height and weight) retrieved from the memory 104, and the so determined body mass index is stored in the memory 104 (step C4).

When the breathing amount determining unit is put in stand-by position, the display 105 and the sound generator 106 provide the following breathing guidance, which is retrieved from the ROM, as in the well known spirotest:

"Procedure 1: Pinch your nose with a clamp, and hold the mouthpiece 111 in your mouth";

"Procedure 2: Breath several times naturally";

"Procedure 3: Take into your lungs as much air as you can at the exact rate or timing directed from the sound generator"; and "Procedure 4: Take the air into your lungs and send it out completely as quickly as you can at the exact rate or timing directed from the sound generator".

Each and every step of procedure accompanies a buzzing sound. Then, the breathing amount measurement starts, plotting a spirogram (breathing curve) Z as shown in FIG. 8 (step C5). In the spirogram W1 stands for the sampling period for which the above Procedure 2 continues; W2 stands for the sampling period for which the above Procedure 3 continues; and W3 stands for the sampling period for which the above Procedure 4 continues.

Then, the microcomputer 101 makes a decision as to whether the measurement is being carried out in good or bad condition, more specifically whether or not the measurement exactly follows the breathing guidance (step C6).

When it is decided that the measurement is not carried out in good condition ("NO" at step C6), the display 105 shows the notification of remeasurement which reads "The measurement was wrongly carried out. Please perform another measurement." and the sound generator produces the buzzing sound (step C7), and the proceeding returns to step C5.

On the contrary, when it is decided that the measurement is being conducted in good condition ("YES" at step C6), the microcomputer 101 performs a required arithmetic operation on the information concerning breathing function (forced vital capacity, standard vital capacity, vital capacity/standard vital capacity percent, one-second-forced expiratory volume, one-second-forced expiratory volume % rate) and stores the results of the arithmetic operation (step C8), as in the subroutine (the pieces of information on breathing function being calculated and stored) at step A5 in EMBODIMENT 1.

Then, the microcomputer 101 makes a decision as to whether or not the results of the breathing function measurement are satisfactory, specifically whether or not one-second-forced expiratory volume % rate (FEV1.0%), and vital capacity/standard vital capacity percent (FVC %) remain in the normal range (FEV1.0%≧70%, and FVC %≧80%) (step C9).

In case that one-second-forced expiratory volume % rate and vital capacity/standard vital capacity percent are out of the normal range ("NO" at step C9), the display 105 shows along with the pieces of information on the body composition (fat-free mass, body fat rate, trunk skeletal muscle rate), the body mass index, the pieces of information on breathing function (forced vital capacity, standard vital capacity, vital capacity/standard vital capacity percent, one-second-forced expiratory volume, one-second-forced expiratory volume % rate) all stored in the memory 54, the abnormal condition notifying message retrieved from the ROM, which reads: "There is the fear of obstructive impairment. Be careful"; "There is the fear of bridle impairment. Be careful"; or "There is the fear of combined impairment. Be careful." At the same time, the sound generator 106 produces an extra buzzing sound (two dot-and-one dash sound combination) prestored in the ROM to inform the user of the arising of the abnormal condition (step C10), thus finishing a series of procedure steps.

In case that one-second-forced expiratory volume % rate and vital capacity/standard vital capacity percent remain within the normal range ("YES" at step C9), the microcomputer 101 calculates the visceral fat rate according to the equation (11a) or (11b) by using the pieces of information on identification of the human body (age, height and weight), body composition (trunk skeletal muscle rate) and the breathing function (forced vital capacity), which are all retrieved from the memory 104 for substitution in the equation. The results of the so calculated visceral fat rate are stored in the memory 104 (step C1). The equation (11a) is applied to males whereas the equation (11b) is applied to females. The vital capacity (VC) comprehends the forced vital capacity (FVC) in significance, and therefore the latter variable (FVC) can be used as a substitute for the former (VC) in either equation.

The display 105 shows the pieces of information on breathing function (forced vital capacity, standard vital capacity, vital capacity/standard vital capacity percent, one-second-forced expiratory volume, one-second-forced expiratory volume % rate) retrieved from the memory 104 and the notification of the normal condition retrieved from the ROM, which reads "Your breathing (lung) function is normal." At the same time the sound generator 106 produces a buzzing sound (two-dot sound) prestored in the ROM (step C12). Thus, the apparatus for assuming information on the amount accumulated visceral fat is finished with a series of procedure steps.

Now, the sub-routines at selected steps in the main flow (calculation and storage of hand-to-hand bioimpedance and the information on the body composition) are described below.

One of such sub-routines is measurement of hand-to-hand bioimpedance at step C2, which is described below.

As shown in FIG. 12, first, the microcomputer 101 is initialized by resetting the timer and other parts (step D1).

Then, the user holds the housing 141 with its left and right sides in his left and right hands respectively, thus putting the electric current conducting electrode 121b and measuring electrode 124b into contact with the left hand and the electric current conducting electrodes 121a and measuring electrode 124a into contact with the right hand. The microcomputer 101 detects the exact instant at which the measurement of bioimpedance starts, particularly the starting point in the sampling period (for example, the 0.5 second-long period) (step D2).

In the affirmative case in which the computer 101 detects the exact instant ("YES" at step D2), the required measurement is carried out by the hand-to-hand bioimpedance determining unit (step D3), returning to step D2.

In the negative case in which the computer 101 does not detect the exact instant ("NO" at step D2), the micro computer 101 performs the smoothing treatment on the hand-to-hand bioimpedance. More specifically, the microcomputer 101 performs a required moving average operation on the last but one bioimpedance and the last bioimpedance, which are averaged (step D4).

Then, the microcomputer 101 makes a decision as to whether the so smoothed hand-to-hand bioimpedance is stable or not, more particularly whether the smoothed bioimpedance remains within a predetermined variation (step D5).

In the negative case in which the so smoothed hand-to-hand bioimpedance is not stable ("NO" at step D5), the hand-to-hand bioimpedance determining unit determines a hand-to-hand bioimpedance (step D3), returning to step D2.

In the affirmative case in which the so smoothed hand-to-hand bioimpedance is stable ("YES" at step D5), the smoothed hand-to-hand bioimpedance is stored in the memory 104 (step D6).

Finally, the display 105 shows the message reading "The measurement is finished", retrieved from ROM, and at the same time, the sound generator 106 produces a three-dash buzzing sound (step D7), thus passing through this mode.

Another sub-routines is to operate the information on body composition and store the so calculated body composition at step C3, as is described below.

Referring to FIG. 13, first, the microcomputer 101 calculates the fat-free mass by retrieving from the memory 104 and substituting the pieces of information of identification of human body (age, height, weight) and the hand-to-hand bioimpedance in the equation (8) (step T1).

Then, the microcomputer 101 calculates the body fat rate by retrieving from the memory 104 and substituting the piece of information of identification of human body (weight) and the so calculated fat-free mass in the equation (9) (step T2).

Finally, the microcomputer determined the trunk skeletal muscle rate by substituting the fat-free mass in the equation (10) (step T3).

The apparatus for assuming information on the amount accumulated visceral fat according to EMBODIMENT 2 works as described above.

As may be understood from the above, the apparatus for assuming information on the amount accumulated visceral fat of EMBODIMENT 2 is so constructed that it may collect pieces of information concerning: the identification of the human body such as sex, age, height and weight; the breathing function such as the forced vital capacity; the body composition such as trunk skeletal muscle rate; and may sure assume the information on the visceral fat accumulation (visceral fat rate according to the equation (11a) or (11b)) easily with a high degree of accuracy.

In EMBODIMENT 2 the information on the identification of the human body includes sex, age, height and weight to determine the visceral fat rate according to the equation (11a) or (11b). To improve the accuracy even more, however, pieces of information of the physical size and shape (at least any one of the upper limb length, lower limb length, middle trunk length and abdominal circumference) may be collected and used for better identification of the human body. Specifically these terms are multiplied by some coefficients, and added as independent variables to the equation 11a or 11b. Then, a visceral fat rate can be provided at a still higher degree of accuracy.

EMBODIMENT 3

Figure 14:
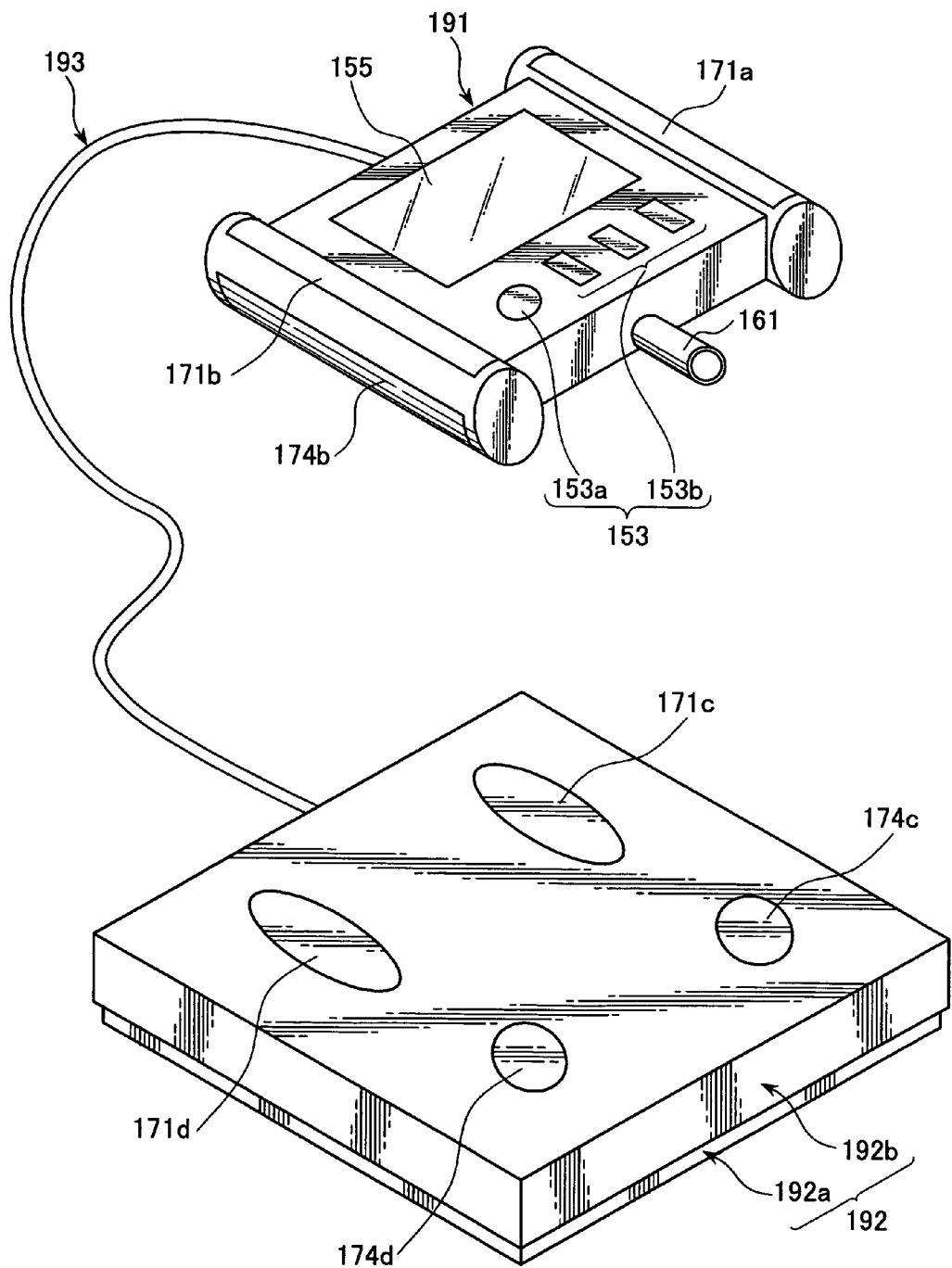
FIG. 14 is a perspective view of an apparatus for assuming information on the amount accumulated visceral fat according to EMBODIMENT 3 of the present invention.
Figure 15:
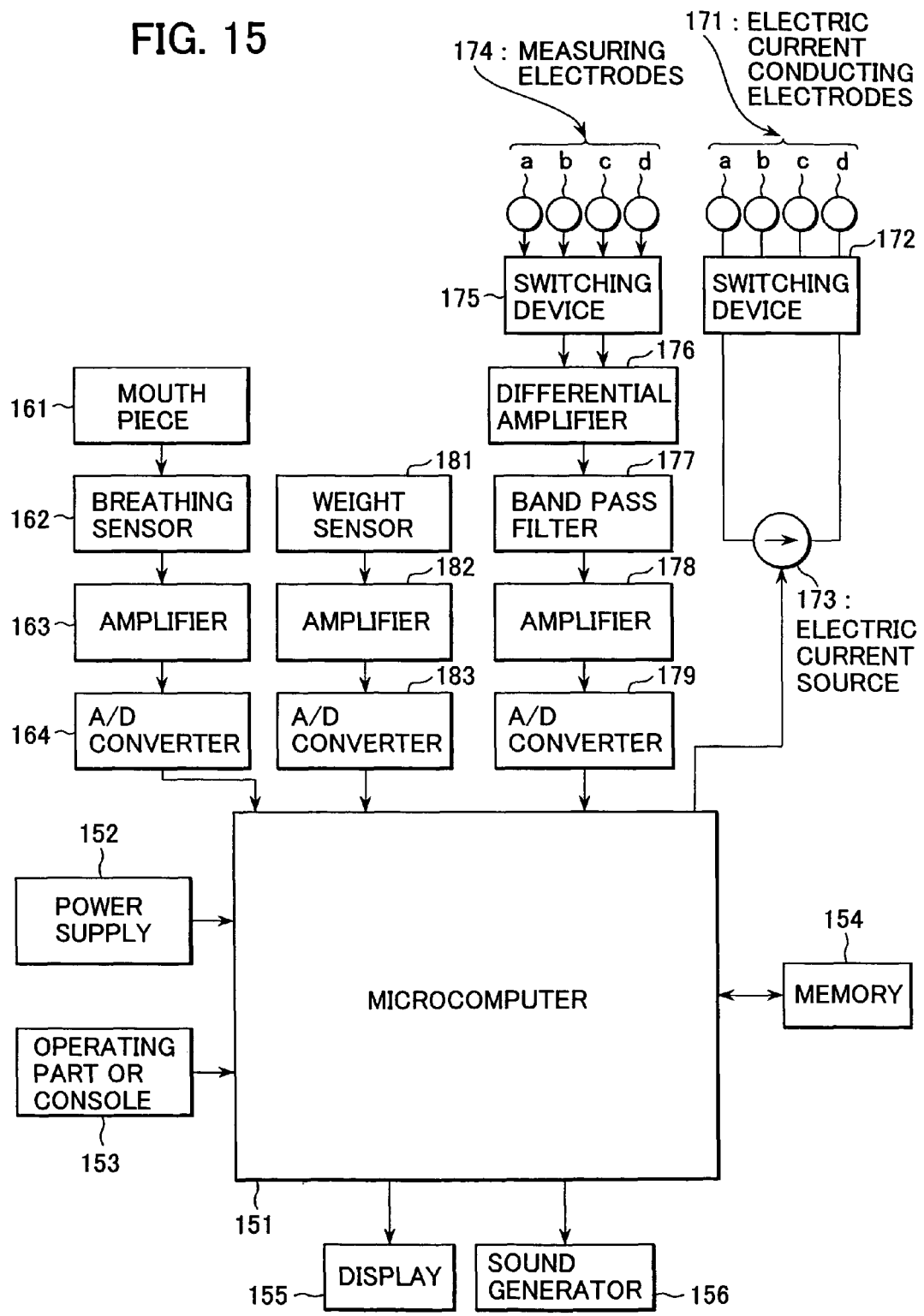
FIG. 15 is a structural block diagram of the apparatus for assuming information on the amount accumulated visceral fat of EMBODIMENT 3.

FIG. 14 is a perspective view of an apparatus for assuming information on the amount accumulated visceral fat according to EMBODIMENT 3 of the present invention, and FIG. 15 is a structural block diagram of the apparatus of FIG. 14, which comprises:

a body identifying unit for obtaining information on the identification of a human body; a breathing function determining unit for obtaining information on the breathing function, which comprises a breathing amount determining unit and a vital capacity calculating unit;

a body composition determining unit for obtaining information on the body composition of the human body, which comprises a limb bioimpedance determining unit, a trunk bioimpedance determining unit and a body composition calculating unit; and a computing unit for calculating information on the amount accumulated visceral fat on the basis of the so obtained pieces of information concerning the identification of the human body, the breathing function and the body composition.

Specifically the apparatus for assuming information on the amount accumulated visceral fat according to EMBODIMENT 3 comprises a power supply 152, an operating part or console 153 (153a and 153b), a mouthpiece 161, a breathing sensor 162, electric current conducting electrodes 171 (171a and 171b), measuring electrodes 174 (174a and 174b), switching devices 172, 175, a differential amplifier 176, a band pass filter or BPF 177, an electric current source 173, amplifiers 163, 178 and 182, A/D converters 164, 179 and 183, a memory 154, a display 155, a sound generator 156 and a microcomputer 151. All of these units and parts are packaged in the housing 191. More specifically, the electric current conducting electrodes 171 (171c and 171d), the measuring electrodes 174 (174c and 174d) and the weight sensor 181 are fixed to the base 192 (base plate 192a and flat plate 192b), which is connected to the housing 191 via a length of electric cord 193. The display 155 and the operating part or console 153 are arranged on the top surface of the housing 191; one of the paired electric current conducting electrodes 171b and one of the paired measuring electrodes 174b are arranged on the left side of the housing 191 whereas the other electric current conducting electrode 171a and the other measuring electrode 174a are arranged on the right side of the housing 191; and the mouthpiece 161 is arranged on the front side of the housing 191. The electrically conducting electrodes 171c and 171d and the measuring electrodes 174c and 174d are arranged on the top surface of the flat plate 192b, and the weight sensor 181 is arranged in the base plate 192a. The remaining units and parts are arranged within the housing 191.

The power supply 152, operating part or console 153, mouthpiece 161, breathing sensor 162, amplifier 163 and A/D converter 164 are similar to the power supply 52, operating part or console 53, mouthpiece 61, breathing sensor 62, amplifier 63 and A/D converter 64 in EMBODIMENT 1. The differential amplifier 176, band pass filter 177, electric current source 173, amplifier 178 and A/D converter 179 are similar to the differential amplifier 126, band pass filter 127, electric current source 123, amplifier 128 and A/D converter 129 in EMBODIMENT 2.

The electric current conducting electrodes 171 (171a, 171b, 171c, 171d) are used in making an electric current flow from hand to hand, from sole to sole or from hand to sole. The measuring electrodes or terminals 174 (174a, 174b, 174c and 174d) are used to detect the potential difference appearing between two selected ones.

The switching device 172 is responsive to control signals from the microcomputer 151 for switching the electric current to flow between both hands, both soles or from one sole to one hand. On the other hand, the switching device 175 is responsive to control signals from the microcomputer 151 for detecting the potential difference appearing across the trunk or between two selected limbs.

The weight sensor 181 detects the weight of the person when standing on the base.

The amplifier 182 amplifies the analogue signal from the weight sensor 181.

The A/D converter 183 converts the analogue signal from the amplifier 182 into the corresponding digital signal.

The memory 154 stores at least the following pieces of information:

i) pieces of information concerning some identified features and attributes of the body (sex, age, height and weight);

ii) a limb bioimpedance (upper-limb bioimpedance, lower-limb bioimpedance) and a trunk bioimpedance (middle trunk bioimpedance) determined by using the measuring electrodes 174, switching device 175, differential amplifier 176, band pass filter 177, amplifier 178, A/D converter 179 and microcomputer 151;

iii) a spirogram provided by sampling the breathing data, which are provided when the mouthpiece 161, breathing sensor 162, amplifier 163, A/D converter 164 and microcomputer 151 work all together;

iv) pieces of information calculated by the microcomputer 151 (later described) or entered by using the operating part or console 153, which pieces of information concerns: the physical size and shape (upper limb length, lower limb length, middle trunk length, abdominal circumference); the body composition (body fat rate, limb skeletal muscle mass, middle trunk skeletal muscle mass, middle trunk skeletal muscle bioimpedance, abdominal subcutaneous fat amount (mass), abdominal subcutaneous fat bioimpedance, visceral mass, visceral bioimpedance, visceral fat bioimpedance, trunk mass, trunk skeletal muscle rate); the body mass index; the breathing function (forced vital capacity, standard vital capacity, vital capacity/standard vital capacity percent, one-second-long-forced expiratory volume, and one-second-forced expiratory volume % rate); the visceral fat accumulation estimated on the basis of the visceral fat bioimpedance (visceral fat rate, visceral fat amount (mass), ratio of visceral fat/subcutaneous fat); and the visceral fat accumulation estimated on the basis of the vital capacity (visceral fat rate, visceral fat amount (mass), ratio of visceral fat/subcutaneous fat).

The display 155 shows at least following pieces of information concerning:

i) the breathing guidance which the microcomputer 51 provides under control, as later described;

ii) remeasurement advice in response to any abnormal condition perceived in measuring the breathing amount by the microcomputer 101, as later described;

iii) results of calculation by the microcomputer 151 (later described), including the body composition (body fat rate, limb skeletal muscle mass, middle trunk skeletal muscle mass, middle trunk skeletal mass bioimpedance, abdominal subcutaneous fat amount (mass) based on the abdominal circumference, abdominal subcutaneous fat bioimpedance, visceral mass, visceral bioimpedance, visceral fat bioimpedance, trunk mass, trunk skeletal muscle rate), the body mass index, the breathing function (forced vital capacity, standard vital capacity, vital capacity/standard vital capacity percent, one-second-forced expiratory volume, and one-second-forced expiratory volume % rate), and the visceral fat accumulation estimated on the basis of the visceral fat bioimpedance or vital capacity (visceral fat rate, visceral fat amount (mass), ratio of visceral fat/subcutaneous fat);

iv) notification of the normal or abnormal condition when determined as such by the microcomputer 151 in terms of the breathing function (particularly one-secondforced expiratory volume % rate and vital capacity/standard vital capacity percent), as later described; and v) notification of the normal or abnormal condition when determined as such by the microcomputer 151 in terms of the middle trunk impedance, as later described The sound generator 156 comprises a buzzer responsive to at least following pieces of information for producing different sounds:

i) information on the breathing guidance controlled by the microcomputer 151, as later described;

ii) information on remeasurement advice in response to abnormal conditions perceived by the microcomputer 151 if any, in measuring the breathing amount, as later described;

iii) notification of normal or abnormal condition detected by the microcomputer 151 in measuring the breathing function (one-second-forced expiratory volume % rate and vital capacity/standard vital capacity percent), as later described; and iv) notification of normal or abnormal condition detected by the microcomputer 151 in terms of the middle trunk bioimpedance, as later described.

The microcomputer 151 comprises a CPU, a ROM for storing control and operation programs, a RAM for temporarily storing the results of arithmetic operations and the determinations and decisions, a timer, I/O ports and other units and parts. The so constructed microcomputer 151 functions to perform required arithmetic operations for obtaining pieces of information concerning; the physical size and shape (upper limb length, lower limb length, middle trunk length, abdominal circumference); the body composition (body fat rate, limb skeletal muscle mass, middle trunk skeletal muscle mass, middle trunk skeletal muscle bioimpedance, abdominal subcutaneous fat amount (mass) based on the abdominal circumference, abdominal subcutaneous fat bioimpedance, visceral mass, visceral bioimpedance, visceral fat bioimpedance, trunk mass, trunk skeletal muscle rate); the body mass index; the breathing function (forced vital capacity, standard vital capacity, vital capacity/standard vital capacity percent, one-second-forced expiratory volume, and one-second-forced expiratory volume % rate); the visceral fat accumulation estimated on the basis of the visceral fat bioimpedance (visceral fat rate, visceral fat amount (mass), ratio of visceral fat/subcutaneous fat);

the visceral fat accumulation estimated on the basis of the vital capacity (visceral fat rate, visceral fat amount (mass), ratio of visceral fat/subcutaneous fat); and the abdominal subcutaneous fat amount (mass) based on the vital capacity;

make a decision as to whether the condition is normal or abnormal in measurement, and as to whether the information on the breathing function indicates normal or abnormal condition;

determine limb bioimpedance and trunk bioimpedance, and provide data representing the breathing amount (data being sampled to plot a spirogram); and give visual and/or vocal messages informing the user of all required pieces of information.

The software program for determining the body composition (body fat rate, limb skeletal muscle mass, middle trunk skeletal muscle mass, middle trunk skeletal muscle bioimpedance, abdominal subcutaneous fat amount (mass) based on the abdominal circumference, abdominal subcutaneous fat bioimpedance, visceral mass, visceral bioimpedance, visceral fat bioimpedance, trunk mass, trunk skeletal muscle rate) and the visceral fat accumulation on the basis of the visceral fat bioimpedance (visceral fat rate, visceral fat amount (mass), ratio of visceral fat/subcutaneous fat) contains the following arithmetic operation:

$$\%FAT = a3 \times Lu^2/Zu + b3 \times Ll^2/Zl + c3 \times Ltm^2/Ztm + d3 \tag{12}$$

$$MMl = a4 \times Ll^2/Zl + b4 \tag{13}$$

$$MMu = a5 \times Lu^2/Zu + b5 \tag{14}$$

$$MMtm = a6 \times MMl + b6 \times MMu + c6 \tag{15}$$

$$ZMM = a7 \times H^2/MMtm + b7 \tag{16}$$

$$FSa = a8m \times Lw^2 + b8m \times H + c8m \times W + d8m \times Age + e8m \tag{17a}$$

$$FSa = a8f \times Lw^2 + b8f \times H + c8f \times W + d8f \times Age + e8f \tag{17b}$$

$$ZFS = a9 \times H^2/FSa + b9 \tag{18}$$

$$VM = a10m \times H + b10m \times W + c10m \times Age + d10m \tag{19a}$$

$$VM = a10f \times H + b10f \times W + c10f \times Age + d10f \tag{19b}$$

$$ZVM = a11m \times H^2/VM + b11m \times H + c11m \times W + d11m \times Age + e11m \tag{20a}$$

$$ZVM = a11f \times H^2/VM + b11f \times H + c11f \times W + d11f \times Age + e11f \tag{20b}$$

$$ZFV = (1/Ztm - 1/ZMM - 1/ZFS) - ZVM \tag{21}$$

$$FVz = a12m \times H^2/ZFV + b12m \times H + c12m \times W + d12m \times Age + e12m \tag{22a}$$

$$FVz = a12f \times H^2/ZFV + b12f \times H + c12f \times W + d12f \times Age + e12f \tag{22b}$$

$$V/Sz = FVz/FSa \tag{23}$$

$$TM = MMtm + VM + FSa + FVz \tag{24}$$

$$\%VFatz = FVz/TM \times 100 \tag{25}$$

$$\%MM = MMtm/TM \times 100 \tag{26}$$

% Fat: body fat rate;
MMl: lower limb skeletal muscle mass
MMu: upper limb skeletal muscle mass
MMtm: middle trunk skeletal muscle mass
ZMM: middle trunk skeletal muscle bioimpedance
FSa: abdominal subcutaneous fat amount (mass) based on abdominal circumference
ZFS: abdominal subcutaneous fat bioimpedance
VM: visceral mass
ZVM: visceral bioimpedance
ZFV: visceral fat bioimpedance
FVz: visceral fat amount (mass) based on visceral fat bioimpedance
V/Sz: ratio of visceral fat/subcutaneous fat based on visceral fat bioimpedance
TM: trunk mass
%VFatz: visceral fat rate based on visceral fat bioimpedance
% MM: trunk skeletal muscle rate
Lu: upper limb length
Ll: lower limb length
Ltm: middle trunk length
Zu: upper limb bioimpedance
Zl: lower limb bioimpedance
Ztm: middle trunk bioimpedance
H: height
W: weight
Age: age
Lw: abdominal circumference a3, b3, c3, d3, a4, b4, a5, b5, a6, b6, c6, a7, b7, a9, b9: constants a8m, b8m, c8m, d8m, e8m, a10m, b10m, c10m, d10m, a11m, b11m, c11m, d11m, e11m, a12m, b12m, c12m, d12m, e12m: constants for males a8f, b8f, c8f, d8f, e8f, a10f, b10f, c10f, d10f, a11f, b11f, c11f, d11f, e11f, a12f, b12f, c12f, d12f, e12f: constants for females The operation concerning information on the physical size and shape (upper limb length, lower limb length, middle trunk length, abdominal circumference) can be carried out in terms of:

calibration curve data representing the relation between the upper limb length and the information on the identification of the human body (at least any one of sex, age, height and weight);

calibration curve data representing the relation between the lower limb length and the information on the identification of the human body (at least any one of sex, age, height and weight);

calibration curve data representing the relation between the middle trunk length and the information on the identification of the human body (at least any one of sex, age, height and weight); and calibration curve data representing the relation between the abdominal circumference and the information on the identification of the human body (at least any one of sex, age, height and weight). The calibration curve data is given in the correlation type or correlation table, and is stored as an operation program.

The body mass index and the pieces of information on breathing function (forced vital capacity, standard vital capacity, vital capacity/standard vital capacity percent, one-second-forced expiratory volume, and one-second-forced expiratory volume % rate) can be calculated according to the equations (1), (2a), (2b), (3), (4), (5) and (7) as in EMBODIMENT 1. The information on the visceral fat accumulation (visceral fat rate) can be calculated according to the equation (11a) or (11b) as in EMBODIMENT 2.

The information on the visceral fat accumulation based on the vital capacity (visceral fat amount (mass), the ratio of visceral fat/subcutaneous fat) and the abdominal subcutaneous fat amount (mass) based on the vital capacity can be calculated according to following equations, which are stored as operation programs:

$$FV = TM \times \%VFat/100 \quad (27)$$

$$FS = (FSa + FVz) - FV \quad (28)$$

$$V/S = FV/FS \quad (29)$$

(FV: visceral fat amount (mass); FS: abdominal subcutaneous fat amount (mass) based on the vital capacity; V/S: ratio of visceral fat/subcutaneous fat; TM: trunk mass; % VFat: visceral fat rate; FSz: abdominal subcutaneous fat amount (mass) based on the abdominal circumference; FVz: visceral fat amount (mass) based on visceral fat bioimpedance)

As regards a decision made as to whether normal or abnormal information on the breathing function is obtained: if FEV1.0% ≧ 70%, and concurrently FVC % ≧ 80%, the result is normal, and otherwise, the result is abnormal.

The operating part or console 153, the weight sensor 181, the amplifier 182, the A/D converter 183, the memory 154, the microcomputer 151 and the power supply 152 all together make up the body identifying unit for obtaining information on the identification of the human body. The mouthpiece 161, the breathing sensor 162, the amplifier 163, the A/D converter 164, the memory 154, the microcomputer 151 and the power supply 152 all together make up the breathing function determining unit for obtaining information on the breathing function. The electric current conducting electrodes 171, the measuring electrodes 174, the switching device 175, the differential amplifier 176, the band pass filter 177, the current source 173, the amplifier 178, the A/D converter 179, the memory 154, the microcomputer 151 and the power supply 152 all together make up the limb bioimpedance determining unit and the trunk bioimpedance determining unit. Finally, the memory 154, the microcomputer 151 and the power supply 152 make up the body composition determining unit for obtaining information on the body composition of the human body, the vital capacity computing unit for calculating information on the breathing function and the computing unit for calculating information on the amount accumulated visceral fat.

Figure 16:
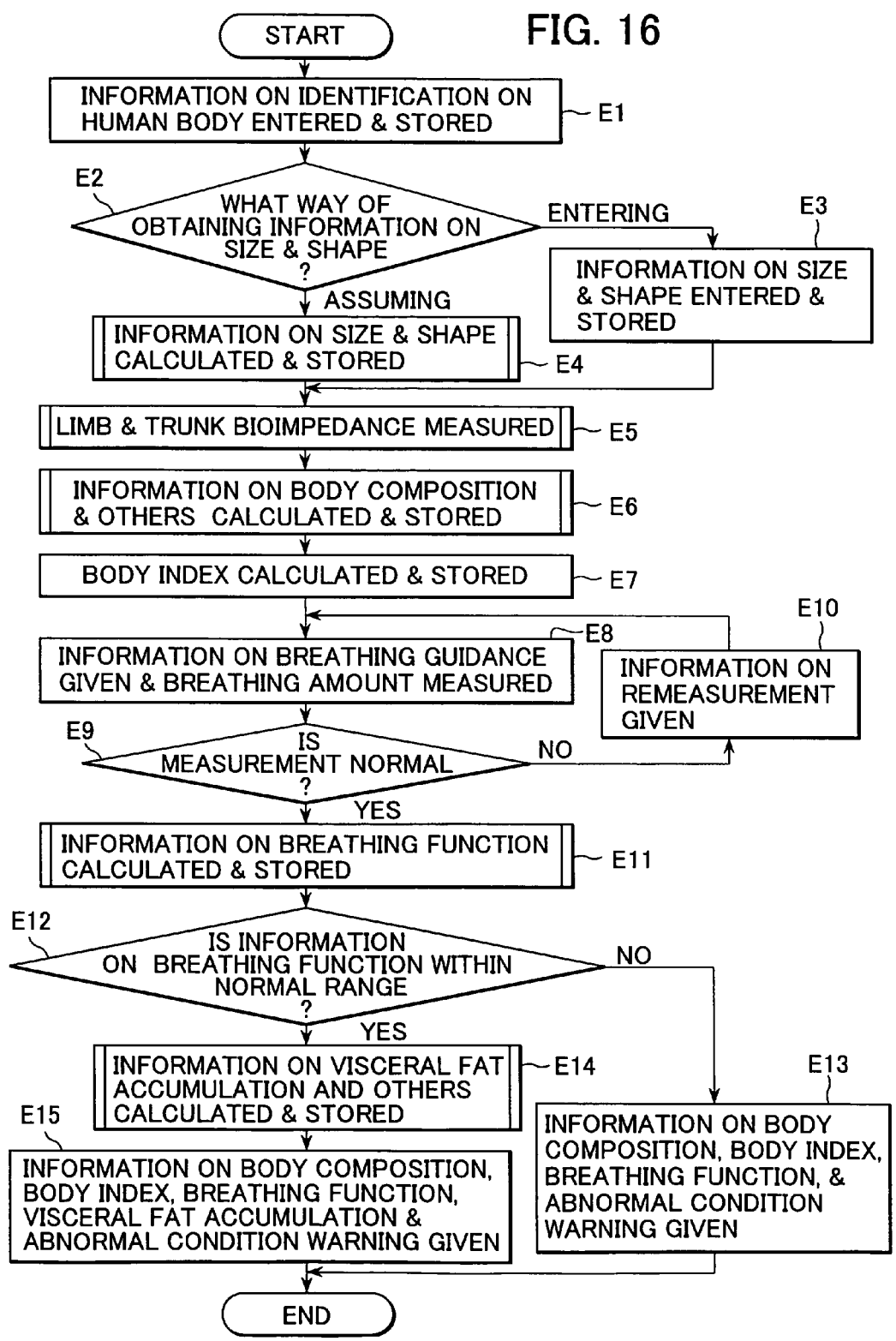
FIG. 16 is a main flow chart depicting how the apparatus for assuming information on the amount accumulated visceral fat of EMBODIMENT 3 works.

FIG. 16 shows a main flowchart and FIGS. 17, 18, 19, 20 and 21 show sub-routine flowcharts. Referring to these figures, the manner in which the apparatus for assuming information on the amount accumulated visceral fat according to EMBODIMENT 3 works is described below.

First, referring to FIG. 16, at the outset the power supply key 153a turns on, allowing the power supply 152 to supply the parts of the electrical system with electricity, thereby permitting the entering of the information on the identification of the human body (sex, age, height and weight). The setting keys 153b are selectively depressed to enter these pieces of information into the memory 154 (step E1).

Sequentially, selection of the way of obtaining the information on the physical size and shape of the human body is permitted ("entering" or "assuming").

Assuming that one of the setting keys 153b allotted to "entering" is selected (step E2), the pieces of information concerning the physical size and shape (upper limb length, lower limb length, middle trunk length and abdominal circumference) can be entered. Specifically, the setting key is depressed to enter and store the desired piece or pieces of information in the memory 154 (step E3).

Assuming that another setting key 153b allotted to "assuming" is selected (step E2), the pieces of information concerning the physical size and shape (upper limb length, lower limb length, middle trunk length and abdominal circumference) can be calculated in the microcomputer 151 (later described), and the so calculated pieces of information are stored (step E4)

Sequentially, the limb bioimpedance (upper limb bioimpedance, lower limb bioimpedance) is measured by the limb bioimpedance determining unit, and the trunk bioimpedance (middle trunk bioimpedance) is measured by the trunk bioimpedance determining unit, as later described (step E5).

Then, the microcomputer 151 calculates the pieces of information on the body composition (body fat rate, limb skeletal muscle mass, middle trunk skeletal muscle mass, middle trunk skeletal muscle bioimpedance, abdominal subcutaneous fat amount (mass) based on the abdominal circumference, abdominal subcutaneous fat bioimpedance, visceral mass, visceral bioimpedance, visceral fat bioimpedance, trunk mass, trunk skeletal muscle rate), and the visceral fat accumulation on the basis of the visceral fat bioimpedance (visceral fat rate, visceral fat amount (mass), ratio of visceral fat/subcutaneous fat) and stores in the memory 154 the information on the body composition and the information on the visceral fat accumulation on the basis of the visceral fat bioimpedance calculated (step E6).

The microcomputer 151 calculates the body mass index according to the equation (7) by substituting the information on the identification of the human body (height and weight) retrieved from the memory 154, and the so determined body mass index is stored in the memory 104 (step E7).

When the breathing amount determining unit is put in stand-by position, the display 155 and the sound generator 106 provide the following breathing guidance message, which is retrieved from the ROM, as is the case with the well known spirotest:

"Procedure 1: Pinch your nose with a clamp, and hold the mouthpiece 161 in your mouth";

"Procedure 2: Breath several times naturally";

"Procedure 3: Take into your lungs as much air as you can at the exact rate or timing directed from the sound generator"; and "Procedure 4: Take the air into your lungs and send it out completely as quickly as you can at the exact rate or timing directed from the sound generator".

Each and every step of procedure accompanies a buzzing sound. Then, the breathing amount measurement starts, plotting a spirogram (breathing curve) Z as shown in FIG. 8 (step E8). In the spirogram of FIG. 8 "W1" stands for the sampling period for which the above Procedure 2 continues; "W2" stands for the sampling period for which the above Procedure 3 continues; and "W3" stands for the sampling period for which the above Procedure 4 continues.

Then, the microcomputer 151 makes a decision as to whether the measurement is being carried out in good or bad condition, more specifically whether or not the measurement exactly follows the breathing guidance (step E9).

When it is decided that the measurement is not carried out in good condition ("NO" at step E9), the display 155 shows the notification of remeasurement which reads "The measurement was wrongly carried out. Please perform another measurement." and at the same time, the sound generator produces the buzzing sound (step E10), and the proceeding returns to step E8.

On the contrary, when it is decided that the measurement is being conducted in good condition ("YES" at step E9), the microcomputer 151 performs a required arithmetic operation on the information concerning breathing function (forced vital capacity, standard vital capacity, vital capacity/standard vital capacity percent, one-second-forced expiratory volume, one-second-forced expiratory volume % rate) and stores the results of the arithmetic operation (step E11), as the microcomputer 51 does in the subroutine (pieces of information on breathing function being calculated and stored) at step A5 in EMBODIMENT 1.

Then, the microcomputer 151 makes a decision as to whether or not the results of the breathing function measurement are satisfactory, specifically whether or not one-second-forced expiratory volume % rate (FEV1.0%), and vital capacity/standard vital capacity percent (FVC %) remain in the normal range (FEV1.0%≧70%, and FVC %≧80%) (step E12).

In case that one-second-forced expiratory volume % rate and vital capacity/standard vital capacity percent are out of the normal range ("NO" at step E12), the display 155 shows: the pieces of information on the body composition (body fat rate, limb skeletal muscle mass, middle trunk skeletal muscle mass, middle trunk skeletal muscle bioimpedance, abdominal subcutaneous fat amount (mass) based on the abdominal circumference, abdominal subcutaneous fat bioimpedance, visceral mass, visceral bioimpedance, visceral fat bioimpedance, trunk mass, trunk skeletal muscle rate);

the pieces of information on the visceral fat accumulation determined on the basis of the visceral fat bioimpedance (visceral fat rate, visceral fat amount (mass), ratio of visceral fat/subcutaneous fat);

the body mass index; and the pieces of information on breathing function (forced vital capacity, standard vital capacity, vital capacity/standard vital capacity percent, one-second-forced expiratory volume, one-second-forced expiratory volume % rate), all of these being previously stored in the memory 154. Along with these pieces of information the display 155 shows the abnormal condition notifying message retrieved from the ROM, which reads: "There is the fear of obstructive impairment. Be careful"; "There is the fear of bridle impairment. Be careful"; or "There is the fear of combined impairment. Be careful". At the same time, the sound generator 156 produces an extra buzzing sound (two dot-and-one dash sound combination) prestored in the ROM to inform the user of the arising of the abnormal condition (step E13), and then a series of procedure steps are finished.

In case that one-second-long-forced expiratory ratio and vital capacity/standard vital capacity percent remain within the normal range ("YES" at step E12), the microcomputer 151 calculates the information on the visceral fat accumulation (visceral fat rate) on the basis of the vital capacity according to the equation (11a) or (11b) by substituting in the equation, the pieces of information concerning the identification of the human body (age, height and weight), the body composition (trunk skeletal muscle rate) and the breathing function (forced vital capacity), which are all retrieved from the memory 104. The equation (11a) is applied to males whereas the equation (11b) is applied to females. The vital capacity (VC) comprehends the forced vital capacity (FVC) in significance, and therefore, the latter variable (FVC) can be used as a substitute for the former (VC) in either equation. Next, the information on the visceral fat accumulation based on the vital capacity (visceral fat amount (mass)) is calculated according to the equation (27) by substituting the information on the visceral fat accumulation based on the vital capacity (visceral fat rate) above calculated and the information on the body composition (trunk mass) retrieved from the memory 154. Sequentially, the abdominal subcutaneous fat amount (mass) based on the vital capacity is calculated according to the equation (28) by substituting the information on the visceral fat accumulation based on the vital capacity (visceral fat amount (mass)) above calculated and the information on the body composition (abdominal subcutaneous fat amount (mass) based on the abdominal circumference, visceral fat amount (mass) based on the visceral fat impedance) retrieved from the memory 154. Sequentially, the information on the visceral fat accumulation based on the vital capacity (ratio of visceral fat/subcutaneous fat) is calculated according to the equation (29) by substituting the information on visceral fat accumulation based on the vital capacity (visceral fat amount (mass)) above calculated and the abdominal subcutaneous fat amount (mass) based on the vital capacity (step E14).

The display 155 shows:

the pieces of information concerning the body composition (body fat rate, limb skeletal muscle mass, middle trunk skeletal muscle mass, middle trunk skeletal muscle bioimpedance, abdominal subcutaneous fat amount (mass) based on the abdominal circumference, abdominal subcutaneous fat bioimpedance, visceral mass, visceral bioimpedance, visceral fat bioimpedance, trunk mass, trunk skeletal muscle rate);

the pieces of information concerning the visceral fat accumulation based on the vital capacity (visceral fat rate, visceral fat amount (mass), ratio of visceral fat/subcutaneous fat);

the body mass index;

the pieces of information on breathing function (forced vital capacity, standard vital capacity, vital capacity/standard vital capacity percent, one-second-long-forced expiratory volume, one-second-forced expiratory volume % rate); and the notification of the normal condition retrieved from the ROM, which reads "Your breathing (lung) function is normal." This message accompanies a buzzing sound (two-dot sound) prestored in the ROM and produced by the sound generator 156 (step E15). Thus, the apparatus for assuming information on the amount accumulated visceral fat is finished with a series of procedure steps.

Now, the sub-routines at some selected steps in the main flow ("operation and storage of the information on the physical size and shape"; "determination of limb and trunk bioimpedance"; "operation and storage of the information on the body composition"; and "operation and storage of the information on the visceral fat accumulation") are described below.

One of such sub-routines is the operation and storage of the physical size and shape at step E4, which is described below.

Figure 17:
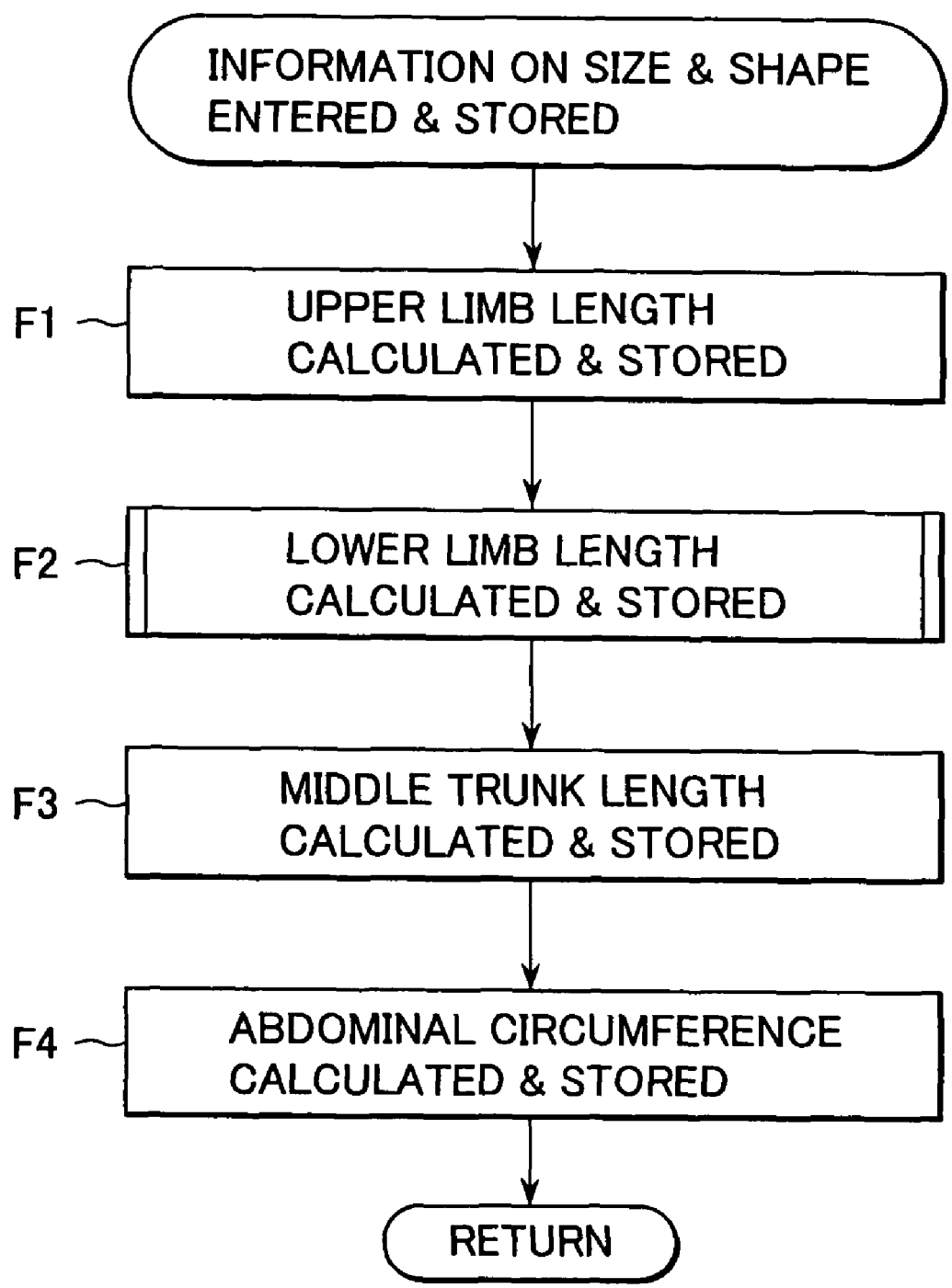
FIG. 17 is a subroutine flow chart depicting how the apparatus for assuming information on the amount accumulated visceral fat of EMBODIMENT 3 works in calculating and storing the information on the size and shape of the human body at a selected step in the main flow chart of FIG. 16.

As shown in FIG. 17, first, in the microcomputer 151 the upper limb length is determined or identified (step F1) from the information on the identification of the human body (at least any one of sex, age, height and weight) previously obtained and stored from the calibration curve data, which represents the correlation between the upper limb length and the information on the identification of the human body.

Then, in the microcomputer 151 the lower limb length is determined or identified (step F2) from the information on the identification of the human body (at least any one of sex, age, height and weight) previously obtained and stored from the calibration curve data, which represents the correlation between the middle trunk length and the information on the identification of the human body.

Then, in the microcomputer 151 the middle trunk length is determined or identified (step F3) from the information on the identification of the human body (at least any one of sex, age, height and weight) previously obtained and stored from the calibration curve data, which represents the correlation between the middle trunk length and the information on the identification of the human body.

Finally, in the microcomputer 151 the abdominal circumference is determined or identified (step F4) from the information on the identification of the human body (at least any one of sex, age, height and weight) previously obtained and stored from the calibration curve data, which represents the correlation between the abdominal circumference and the information on the identification of the human body. Thus, this working mode is finished.

Another or second sub-routine is the measurement of limb and trunk bioimpedance at step E5, which is described below.

Figure 18:
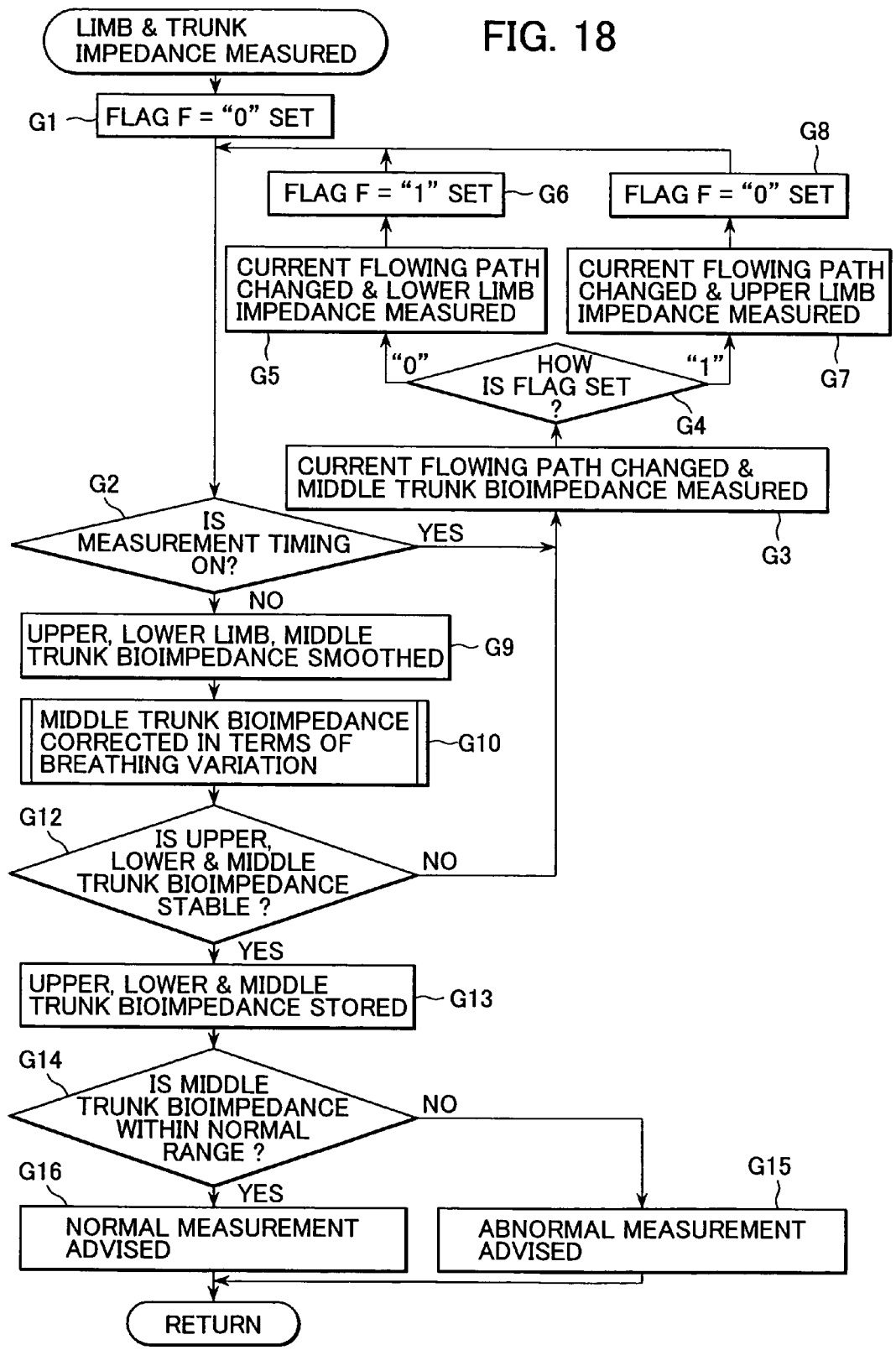
FIG. 18 is a subroutine flow chart depicting how EMBODIMENT 3 works in determining and storing the information on the limb and trunk bioimpedance at a selected step in the main flow chart of FIG. 16.

As shown in FIG. 18, first, in the microcomputer 151 the flag is set to "0", starting the timer (step G1).

Then, in the microcomputer 151 a decision is made as to whether or not the measurement timing (for example, 0.5 second-long sampling period) is met.

In the affirmative case in which the measurement timing is on ("YES" at step G2), in the microcomputer 151, the switching devices 172 and 175 belonging to the electric current conducting electrodes 171 and the measuring electrodes 174 respectively turn to establish the current flowing path from the right arm to the right leg (otherwise, from the left arm to the left leg; from the right arm to the left leg; or from the left arm to the right leg), and the bioimpedance appearing between the right arm and the right leg is determined as the middle trunk bioimpedance (step G3).

Then, in the microcomputer 151 a decision is made as to whether or not the flag is set to "0" (step G4). In the affirmative case ("0" at step G4), in the microcomputer 151, the switching devices 172 and 175 belonging to the electric current conducting electrodes 171 and the measuring electrodes 174 respectively are thrown to establish the current flowing path from the right leg to the left leg, and the bioimpedance appearing between the right leg and the left leg is determined as the lower limb bioimpedance (step G5). Then, the flag is set to "1" (step G6), and the procedure returns to step G2. In case that the flag is set to "1" ("1" at step G4), in the microcomputer 151, the switching devices 172 and 175 belonging to the electric current conducting electrodes 171 and the measuring electrodes 174 respectively turn to establish the current flowing path from the right arm to the left arm, and the bioimpedance appearing between the right arm and the left arm is determined as the upper limb bioimpedance (step G7). Then, the flag is set to "0" (step G8), returning to step G2.

While the measurement timing is off ("NO" at step G2), in the microcomputer 151 the middle trunk bioimpedance, upper limb impedance and lower limb impedance are subjected to smoothing treatment (for example, moving average) at step G9.

Sequentially, in the microcomputer 151 the middle trunk bioimpedance is corrected in terms of the variation caused by breathing (step at G10).

In the microcomputer 151 a decision is made as to whether or not the middle trunk bioimpedance thus corrected in respect of the breathing variation, and the upper and lower limb bioimpedances subjected to the smoothing treatment are stable in value (specifically each variable is determined and treated as predetermined times as required, and a decision is made as to whether it remains within the predetermined range every time.) (step G12).

If any of these variables are not stable ("NO" at step G12), the proceeding returns to step G3, repeating the procedure as mentioned above.

In case that every variable is found stable ("YES" at step G12), the middle trunk bioimpedance last corrected in respect of the breathing variation, and the upper and lower limb bioimpedances last smoothed are stored in the memory 154 (step G13).

Next, in the microcomputer 151 a decision is made as to whether the measurement is conducted in good or bad condition, more specifically, as to whether the last middle trunk bioimpedance remains within the normal range (the allowable standard value: ±3SD, for example, 26.7±3.45) (step G14). The middle trunk bioimpedance will be significantly affected by how much the person has eaten or drunk or by how much liquid waste collects in his bladder. In consideration of the degree of influence on the measurement the normal range is determined.

In case that the middle trunk bioimpedance is not in the normal range ("NO" at step G14), the display 155 shows the abnormal message retrieved from the ROM, which reads "The middle trunk is not in good condition. Another measurement is required after bowel movement or urination." At the same time, the sound generator 156 produces a warning sound (a two-dot-and-one-dash, bee-buzzing-like sound combination), which is retrieved from the ROM (step G15). Then, this working mode is finished.

In case that the middle trunk bioimpedance is in the normal range ("YES" at step G14), the display 155 shows the normal message retrieved from the ROM, which reads "The middle trunk is appropriate for measurement in condition." At the same time the sound generator 156 produces a passing sound (a two-dot, bee-buzzing-like sound combination), which is retrieved from the ROM (step G16). Thus, this working mode is finished.

Figure 19:
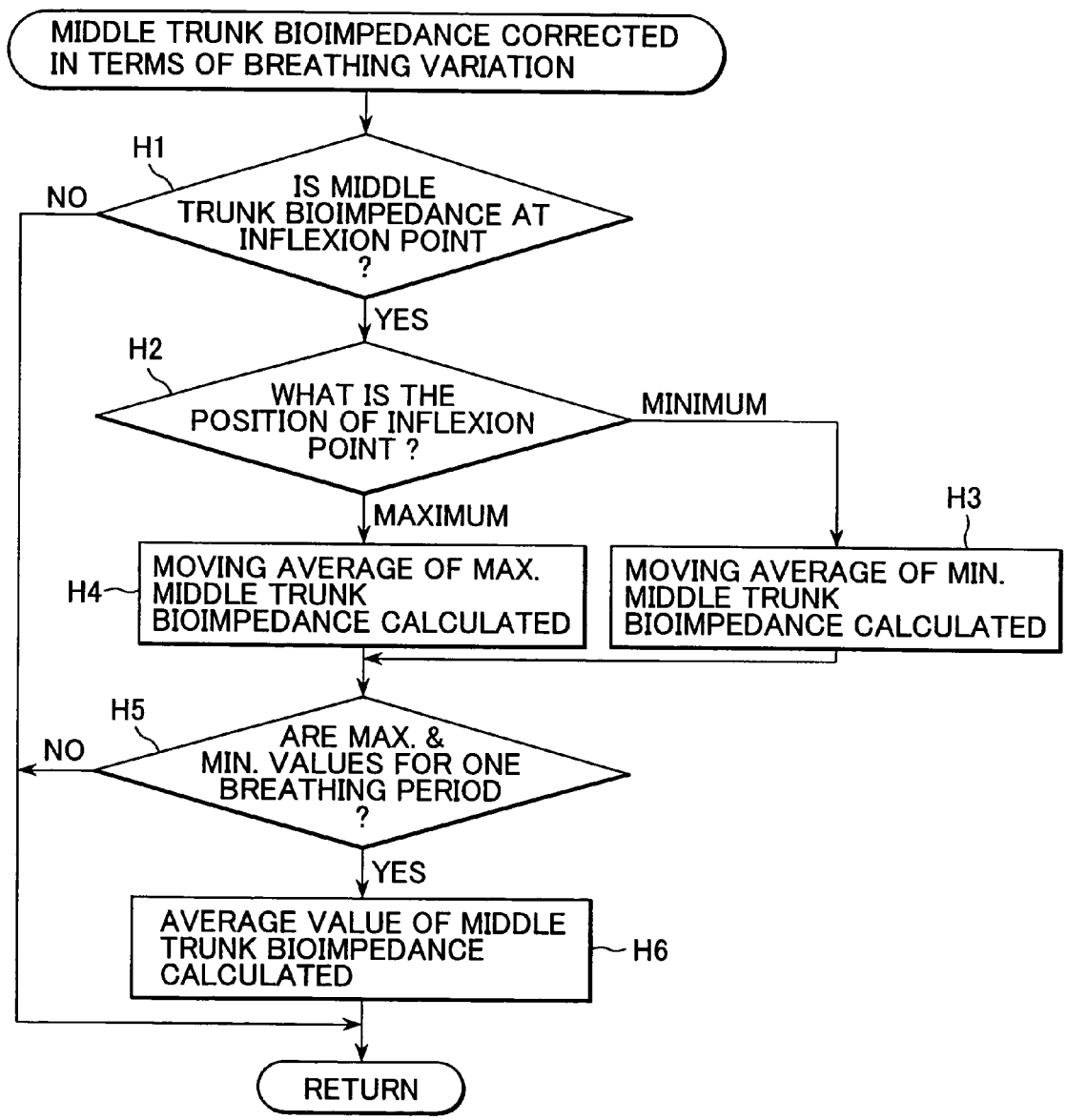
FIG. 19 is a subroutine flow chart depicting how EMBODIMENT 3 works in correcting the middle trunk bioimpedance in terms of breathing variation at a selected step in the subroutine flow chart of FIG. 18.

Here, a subroutine adopted in the procedure at step G10 (correction of the middle trunk bioimpedance in respect of the breathing variation) in the instant subroutine (the limb and trunk bioimpedance measurement) is described below:

Referring to FIG. 19, in the microcomputer 151, first, a decision is made as to whether or not the smoothed middle trunk bioimpedance is at an inflexion point (step H1).

In the negative case in which the smoothed middle trunk bioimpedance is not at an inflexion point ("NO" at step H1), this working mode is finished.

In the affirmative case in which the smoothed middle trunk bioimpedance is at an inflexion point ("YES" at step H1), a decision is made as to whether the infection point of the smoothed middle trunk bioimpedance is at the "maximum" or "minimum" in position (step H2).

If the position of the infection point is found at the "minimum" (minimum at step H2), the minimum infection point value (the minimum value of middle trunk bioimpedance) is subjected to the moving average treatment (step H3). Otherwise, if the position of the infection point is found at the "maximum" (maximum at step H2), the maximum infection point value (the maximum value of middle trunk bioimpedance) is subjected to the moving average treatment (step H4), thus proceeding to step H5.

Then, in the microcomputer 151, a decision is made as to the minimum and maximum values of middle trunk bioimpedance both subjected to the moving average are calculated over one breathing period (step H5).

In the negative case ("NO" at step H5), this working mode is finished.

In the affirmative case ("YES" at step H5), the average of the minimum and maximum values of middle trunk bioimpedance subjected to the moving average (that is, the middle trunk bioimpedance corrected in respect of the breathing variation) is determined at step H6, and then this working mode is finished.

Still another or third sub-routine is the operation and storage of the information on body composition at step E6 of the main stream proceeding, which subroutine is described below in detail.

Figure 20:
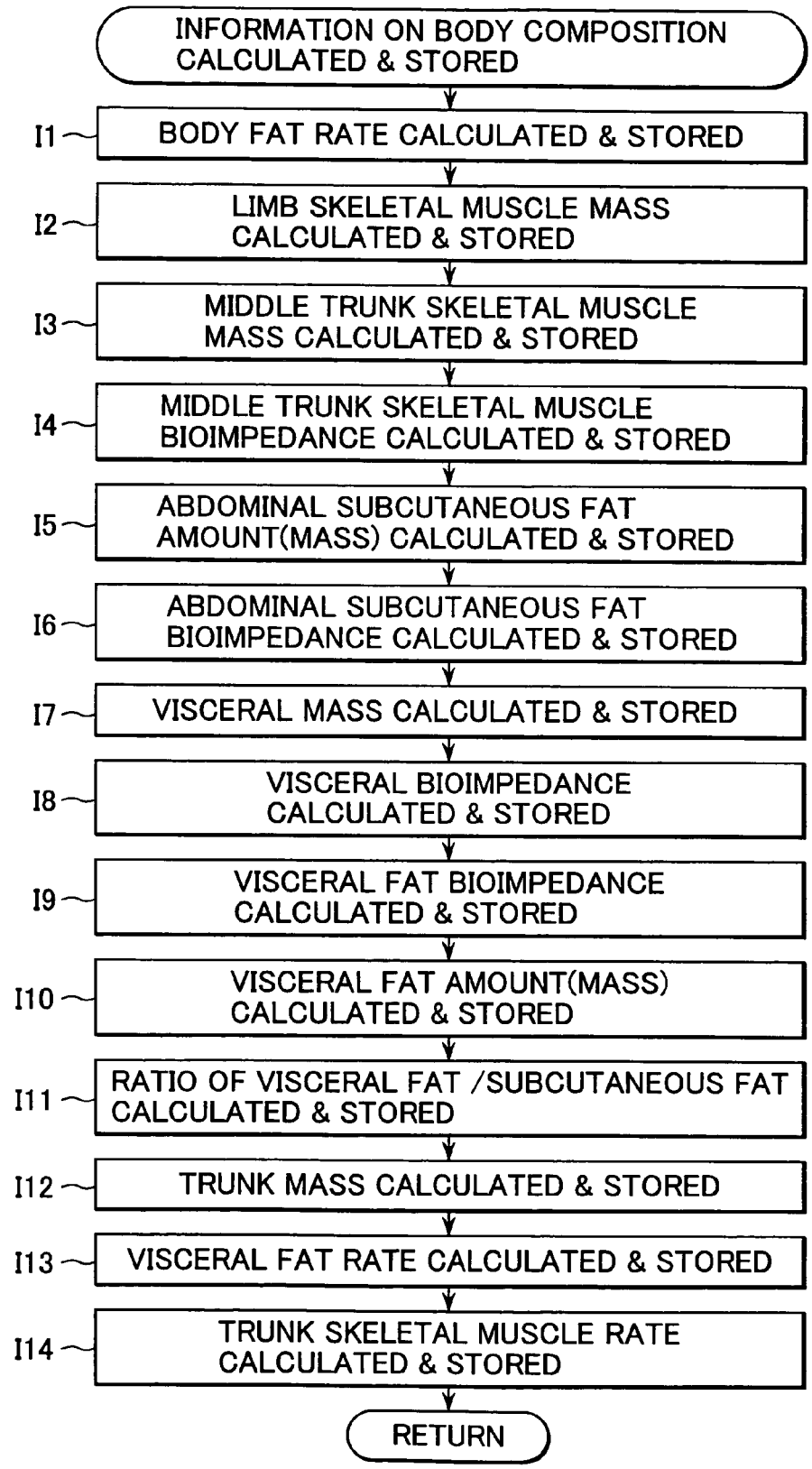
FIG. 20 is a subroutine flow chart depicting how EMBODIMENT 3 works in calculating and storing the information on the body composition at a selected step in the main flow chart of FIG. 16.

Referring to FIG. 20, first, in the microcomputer 151, the body fat rate is calculated according to the equation 12 by substituting the information on the physical size and shape (upper limb length, lower limb length, middle trunk length and abdominal circumference), the limb bioimpedance (upper limb bioimpedance and lower limb bioimpedance) and trunk bioimpedance (middle trunk bioimpedance) all retrieved from the memory 154, and the so calculated body fat rate is stored in the memory 154 (step I1).

Sequentially, in the microcomputer 151, the lower limb skeletal muscle mass is determined according to the equation 13 by substituting the information on the physical size and shape (lower limb length) and the limb bioimpedance (lower limb bioimpedance) both retrieved from the memory 154, and the upper limb skeletal muscle mass is determined according to the equation 14 by substituting the information on the physical size and shape (upper limb length) and the limb bioimpedance (upper limb bioimpedance) both retrieved from the memory 154. The so determined lower and upper limb skeletal muscle masses are stored in the memory 154 (step I2).

Sequentially in the microcomputer 151 the middle trunk skeletal muscle mass is determined according to the equation 15 by substituting the lower and upper limb skeletal muscle masses, which are retrieved from the memory 154 (step I3).

Sequentially in the microcomputer 151 the middle trunk skeletal muscle bioimpedance is determined according to the equation 16 by substituting the so determined middle trunk skeletal muscle mass and the information on the physical size and shape (height), which are retrieved from the memory 154 (step I4).

Sequentially in the microcomputer 151 the abdominal subcutaneous fat amount (mass) is determined according to the equation 17a or 17b by substituting the information on the physical size and shape (abdominal circumference) and the information on the identification of the human body (age, height and weight), which are retrieved from the memory 154, and the so determined abdominal subcutaneous fat amount (mass) based on the abdominal circumference is stored in the memory 154 (step I5). The equation 17a is applied to males whereas the equation 17b is applied to females.

Sequentially in the microcomputer 151 the abdominal subcutaneous fat bioimpedance is determined according to the equation 18 by substituting the abdominal subcutaneous fat amount (mass) based on the abdominal circumference and the information on the identification of the human body (height), both retrieved from the memory 154, and the so determined abdominal subcutaneous fat bioimpedance is stored in the memory 154 (step I6).

Sequentially in the microcomputer 151 the visceral mass is determined according to the equation 19a or 19b by substituting the information on the identification of the human body (age, height and weight) retrieved from the memory 154, and the so determined visceral mass is stored in the memory 154 (step I7). The equation 19a is applied to males whereas the equation 19b is applied to females.

Sequentially in the microcomputer 151 the visceral bioimpedance is determined according to the equation 20a or 20b by substituting the visceral mass and the information on the identification of the human body (age, height and weight) both retrieved from the memory 154, and the so determined visceral bioimpedance is stored in the memory 154 (step I8). The equation 20a is applied to males (sex) whereas the equation 20b is applied to females (sex).

Sequentially in the microcomputer 151 the visceral fat bioimpedance is determined according to the equation 21 by substituting the middle trunk bioimpedance, middle trunk skeletal muscle bioimpedance, abdominal subcutaneous fat bioimpedance and visceral bioimpedance, all retrieved from the memory 154, and the so determined visceral fat bioimpedance is stored in the memory 154 (step I9).

Sequentially in the microcomputer 151 the visceral fat amount (mass) is determined on the basis of the visceral fat bioimpedance according to the equation 22a or 22b by substituting the visceral fat bioimpedance and the information on the identification of the human body (age, height and weight), both retrieved from the memory 154, and the so determined visceral fat amount (mass) based on the visceral fat bioimpedance is stored in the memory 154 (step I10). The equation 22a is applied to males whereas the equation 22b is applied to females.

Sequentially in the microcomputer 151 the ratio of visceral fat/pannicule is determined on the basis of the visceral fat bioimpedance according to the equation 23 by substituting the visceral fat amount (mass) based on the visceral fat bioimpedance and the abdominal subcutaneous fat amount (mass) based on the abdominal circumference, both retrieved from the memory 154, and the so determined ratio of visceral fat/subcutaneous fat is stored in the memory 154 (step I11).

Sequentially in the microcomputer 151 the trunk mass is determined according to the equation 24 by substituting the middle trunk skeletal muscle mass, the visceral mass, the abdominal subcutaneous fat amount (mass) based on the abdominal circumference, and the visceral fat amount (mass) based on the visceral fat bioimpedance, all retrieved from the memory 154, and the so determined trunk mass is stored in the memory 154 (step I12).

Sequentially in the microcomputer 151 the visceral fat rate is determined on the basis of the visceral fat bioimpedance according to the equation 25 by substituting the visceral fat bioimpedance retrieved from the memory 154, and the so determined visceral fat rate is stored in the memory 154 (step I13).

Sequentially in the microcomputer 151 the trunk skeletal muscle rate is determined according to the equation 26 by substituting the trunk mass and the middle trunk skeletal muscle mass both retrieved from the memory 154, and the so determined trunk skeletal muscle rate is stored in the memory 154 (step I14). Thus, this working mode is finished.

Yet still another or fourth sub-routine is the operation and storage of visceral fat accumulation at step EI4 of the main stream proceeding, which subroutine is described below in detail.

Figure 21:
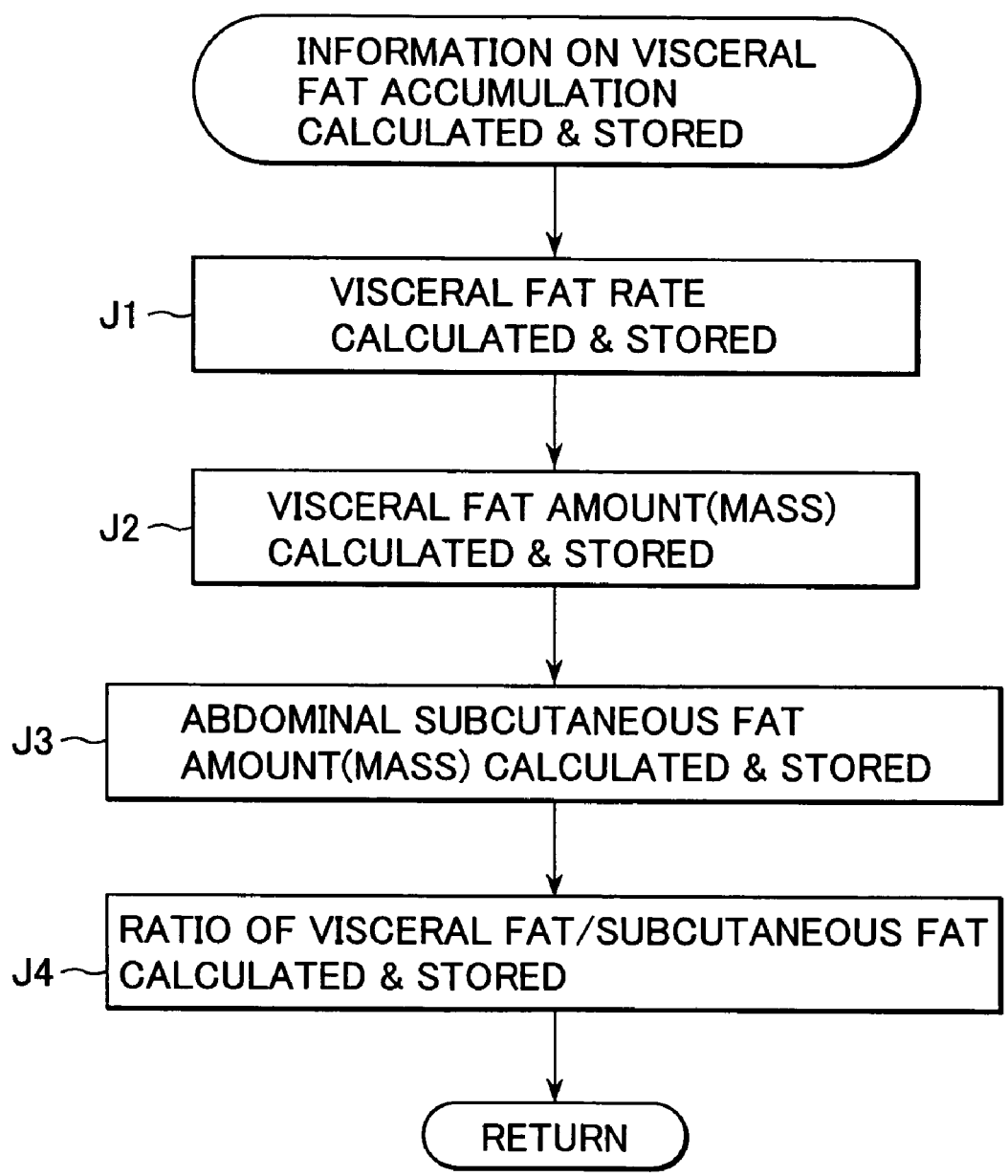
FIG. 21 is a subroutine flow chart depicting how EMBODIMENT 3 works in calculating and storing the information on the visceral fat accumulation at a selected step in the main flow chart of FIG. 16.

Referring to FIG. 21, in the microcomputer 151, first, the information on the visceral fat accumulation is determined on the basis of the vital capacity according to the equation 11a or 11b by substituting the information on the identification of the human body (age, height and weight), the information on the body composition (trunk skeletal muscle rate) and the information on the breathing function (forced vital capacity). The so determined information on the visceral fat accumulation based on the vital capacity (visceral fat rate) is stored in the memory 154 (step J1). If the information on the identification of the human body (sex) indicates male, the equation 11a is adopted, and otherwise, the equation 11b is adopted. The vital capacity comprehends the forced vital capacity, and therefore, the forced vital capacity can be used as a substitute for the vital capacity.

Sequentially in the microcomputer 151 the information on the visceral fat accumulation (visceral fat amount (mass)) is determined on the basis of the vital capacity according to the equation 27 by substituting the information on the visceral fat accumulation based on the vital capacity (visceral fat rate) and the trunk mass both retrieved from the memory 154, and the so determined information on the visceral fat accumulation based on the vital capacity (visceral fat amount (mass)) is stored in the memory 154 (step J2).

Sequentially in the microcomputer 151 the abdominal subcutaneous fat amount (mass) is determined on the basis of the vital capacity according to the equation 28 by substituting the information on the visceral fat accumulation based on the vital capacity (visceral fat amount (mass)), the abdominal subcutaneous fat amount (mass) based on the abdominal circumference and the visceral fat amount (mass) based on the visceral fat bioimpedance, all retrieved from the memory 154, and the so determined abdominal subcutaneous fat amount (mass) based on the vital capacity is stored in the memory 154 (step J3).

Sequentially in the microcomputer 151 the ratio of visceral fat/subcutaneous fat is determined according to the equation 29 by substituting the visceral fat amount (mass) based on the vital capacity and the abdominal subcutaneous fat amount (mass) based on the vital capacity, both retrieved from the memory 154, and the so determined ratio of visceral fat/ subcutaneous fat based on the vital capacity is stored in the memory 154 (step J4). Thus, this working mode is finished.

The apparatus for assuming information on the amount accumulated visceral fat according to EMBODIMENT 3 works as described above.

As may be understood from the above, the apparatus for assuming information on the apparatus for assuming information on the amount accumulated visceral fat of EMBODIMENT 3 is so constructed that it may collect pieces of information concerning: the identification of the human body such as sex, age, height and weight; the breathing function such as the forced vital capacity; and the body composition such as trunk skeletal muscle rate; and may sure assume the information on the visceral fat accumulation (visceral fat rate) according to the equation (11a) or (11b) with ease and with a high degree of accuracy.

In EMBODIMENT 3 the information on the identification of the human body includes sex, age, height and weight to determine the visceral fat rate according to the equation (11a) or (11b). To improve the accuracy still more pieces of information of the physical size and shape (at least any one of the upper limb length, lower limb length, middle trunk length and abdominal circumference) may be collected and used for better identification of the human body. Specifically these terms are multiplied by some coefficients, and added as independent variables to the equation 11a or 11b. Then, a visceral fat rate can be provided at a still higher degree of accuracy.

The subroutine at step E5 (measurement of limb and trunk bioimpedance) of the main stream proceeding is described by referring to FIG. 18. It may be replaced by a series of procedures shown in FIG. 22 and described below:

First, in the microcomputer 151, a decision is made as to whether or not the measurement of trunk bioimpedance (middle trunk length bioimpedance) just meets the starting point of the measurement timing (for example, 0.5 second-long sampling period) (step K1).

In the affirmative case ("YES" at step K1), in the microcomputer 151, the switching devices 172 and 175 belonging to the electric current conducting electrodes 171 and the measuring electrodes 174 respectively turn to establish the electric current flowing path from the right arm to the right leg, and the bioimpedance appearing therebetween is determined as the middle trunk bioimpedance Ztmrr. Likewise, the switching devices 172 and 175 turn to establish the electric current flowing path from the left arm to the left leg, and the bioimpedance appearing therebetween is determined as the middle trunk bioimpedance Ztmll. Similarly the switching devices 172 and 175 turn to establish the electric current flowing path from the right arm to the left leg, and the bioimpedance appearing therebetween is determined as the middle trunk bioimpedance Ztmrl, and finally the switching devices 172 and 175 turn to establish the electric current flowing path from the left arm to the right leg, and the bioimpedance appearing therebetween is determined as the middle trunk bioimpedance Ztmlr (step K2).

While the measurement timing is off ("NO" at step K1), in the microcomputer 151 the middle trunk bioimpedances (Ztmrr; Ztmll; Ztmrl and Ztmlr) thus measured are subjected to smoothing treatment (for example, moving average) at step K3.

Sequentially, in the microcomputer 151 the middle trunk bioimpedances (Ztmrr; Ztmll; Ztmrl and Ztmlr) are corrected in terms of the variation caused by breathing (step K4).

Sequentially in the microcomputer 151 a decision is made as to whether or not each middle trunk bioimpedance (Ztmrr; Ztmll; Ztmrl or Ztmlr) thus corrected in respect of breathing variation is stable in value (specifically each variable is determined and treated as predetermined times as required, and a decision is made as to whether or not it remains within the predetermined range every time.) (step K5).

If any of these variables are not stable ("NO" at step K5), the proceeding returns to step K2 for remeasurement.

In case that every variable is found stable ("YES" at step K5), in the microcomputer 151, a decision is made as to whether or not the balance is kept between the middle trunk bioimpedances (Ztmrr; Ztmll; Ztmrl and Ztmlr) appearing along the different electric current flowing paths, more specifically, whether or not the middle trunk bioimpedance Ztmrr appearing the right arm-to-right leg electric current flowing path is almost equal to the middle trunk bioimpedance Ztmrl appearing along the right arm-to-left leg electric current flowing path; the middle trunk bioimpedance Ztmlr appearing along the left arm-to-right leg electric current flowing path is almost equal to the middle trunk bioimpedance Ztmll appearing along the left arm-to-left leg electric current flowing path; and finally, the middle trunk bioimpedance Ztmrr appearing along the right arm-to-right leg electric current flowing path is larger than the middle trunk bioimpedance Ztmll appearing along the left arm-to-left leg electric current flowing path (step K6).

If the balance is lost ("NO" at step K6), in the microcomputer 151, a decision is made as to whether or not the middle trunk bioimpedance Ztmrr appearing along the right arm-to-right leg electric current flowing path is almost equal to the middle trunk bioimpedance Ztmrl appearing along the right arm-to-left leg electric current flowing path, and as to whether or not the middle trunk bioimpedance Ztmlr appearing along the left arm-to-right leg electric current flowing path is almost equal to the middle trunk bioimpedance Ztmll appearing along the left arm-to-left leg electric current flowing path (step K7). In the affirmative case ("YES" at step K7), the microcomputer 151 allows the display to give some advisory words about the abnormal condition retrieved from the ROM, saying "The trunk measuring condition (right upper part) is not good.", and "Another measurement is required after bowel movement and urination." At the same time, the sound generator 156 produces a warning sound (a two-dot-and-one dash, bee-buzzing-like sound combination) (step K10). In the negative case ("NO" at step K7) a decision is made as to whether or not the middle trunk bioimpedance Ztmrr appearing along the right arm-to-right leg electric current flowing path is larger than the middle trunk bioimpedance Ztmlr appearing along the left arm-to-right leg electric current flowing path (step K8). When the middle trunk bioimpedance Ztmrr is found larger than the middle trunk bioimpedance Ztmlr ("YES" at step K8), the microcomputer 151 allows the display to give some advisory words about the abnormal condition retrieved from the ROM, saying "The trunk measuring condition (left lower part) is not good.", and "Another measurement is required after bowel movement and urination." At the same time, the sound generator 156 produces a warning sound (a two-dot-and-one dash, bee-buzzing-like sound combination) (step K10). When the middle trunk bioimpedance Ztmrr is not found larger than the middle trunk bioimpedance Ztmlr ("NO" at step K8), a decision is made as to whether or not the middle trunk bioimpedance Ztmrl appearing along the right arm-to-left leg electric current flowing path is larger than the middle trunk bioimpedance Ztmrr appearing along the right arm-to-right leg electric current flowing path (step K9). If the middle trunk bioimpedance Ztmrl is found larger than the middle trunk bioimpedance Ztmrr ("YES" at step K9), the microcomputer 151 allows the display to give some advisory words about the abnormal condition retrieved from the ROM, saying "The trunk measuring condition (right lower part) is not good", and "Another measurement is required after bowel movement and urination." At the same time, the sound generator 156 produces a warning sound (a two-dot-and-one dash, bee-buzzing-like sound combination) (step K10). When the middle trunk bioimpedance Ztmrl is not found larger than the middle trunk bioimpedance Ztmrr ("NO" at step K9), the microcomputer 151 allows the display to give some advisory words about the abnormal condition retrieved from the ROM, saying "The trunk measuring condition (left upper part) is not good", and "Another measurement is required after bowel movement and urination." At the same time, the sound generator 156 produces a warning sound (a two-dot-and-one dash, bee-buzzing-like sound combination) (step K10), thus proceeding to step K12.

If the balance is kept ("YES" at step K6), the microcomputer 151 allows the display to give some advisory words about the normal condition retrieved from the ROM, saying, "The trunk measuring condition is good." At the same time, the sound generator 156 produces a passing sound (a two-dot, bee-buzzing-like sound combination) (step K11).

Sequentially any one of the last trunk middle bioimpedances corrected in terms of breathing variation is stored in the memory 154 (step K12).

Sequentially, in the microcomputer 151, a decision is made as to whether or not the measurement of limb bioimpedance (upper limb length bioimpedance, lower limb bioimpedance) just meets the starting point of the measurement timing (for example, 0.5 second-long sampling period) (step K13).

In the affirmative case ("YES" at step K13), in the microcomputer 151, the switching devices 172 and 175 belonging to the electric current conducting electrodes 171 and the measuring electrodes 174 respectively turn to establish the electric current flowing path from the right leg to the left leg, and the bioimpedance appearing along the electric current flowing path is determined by the limb impedance determining unit as the lower limb bioimpedance. Likewise, the switching devices 172 and 175 turn to establish the electric current flowing path from the right arm to the right leg, and the bioimpedance appearing along the electric current flowing path is determined by the limb impedance determining unit as the upper limb bioimpedance (step K14), returning to step K13.

While the measurement timing is off ("NO" at step K13), in the microcomputer 151 the upper and lower limb bioimpedances are subjected to smoothing treatment (for example, moving average) at step K15.

Sequentially, in the microcomputer 151 a decision is made as to whether or not the so smoothed upper and lower limb bioimpedances are stable (for example, each of the bioimpedances measured a predetermined number of times remains within a predetermined allowance of variation) (step K16).

In the negative case in which each limb bioimpedance is not found stable ("NO" at step K16), the proceeding returns to step K14 for remeasurement.

In the affirmative case in which each limb bioimpedance is found stable ("YES" at step K16), the last smoothed upper and lower limb bioimpedances are stored in the memory 154 (step K17), and this working mode is finished.

Figure 22:
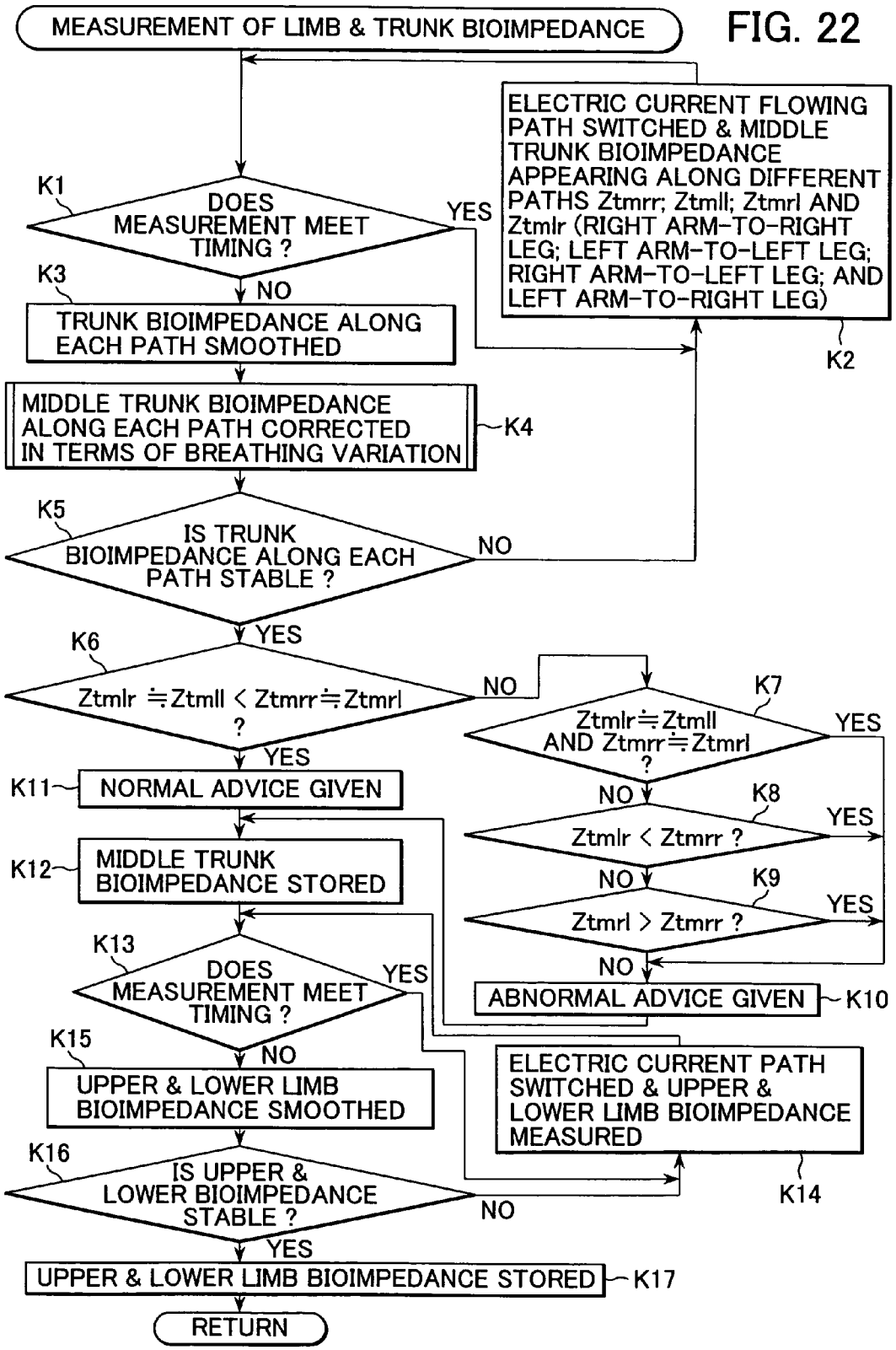
FIG. 22 is another subroutine flow chart depicting how EMBODIMENT 3 works in determining and storing the information on the limb and trunk bioimpedance at a selected step in the main flow chart of FIG. 16.
Figure 23:
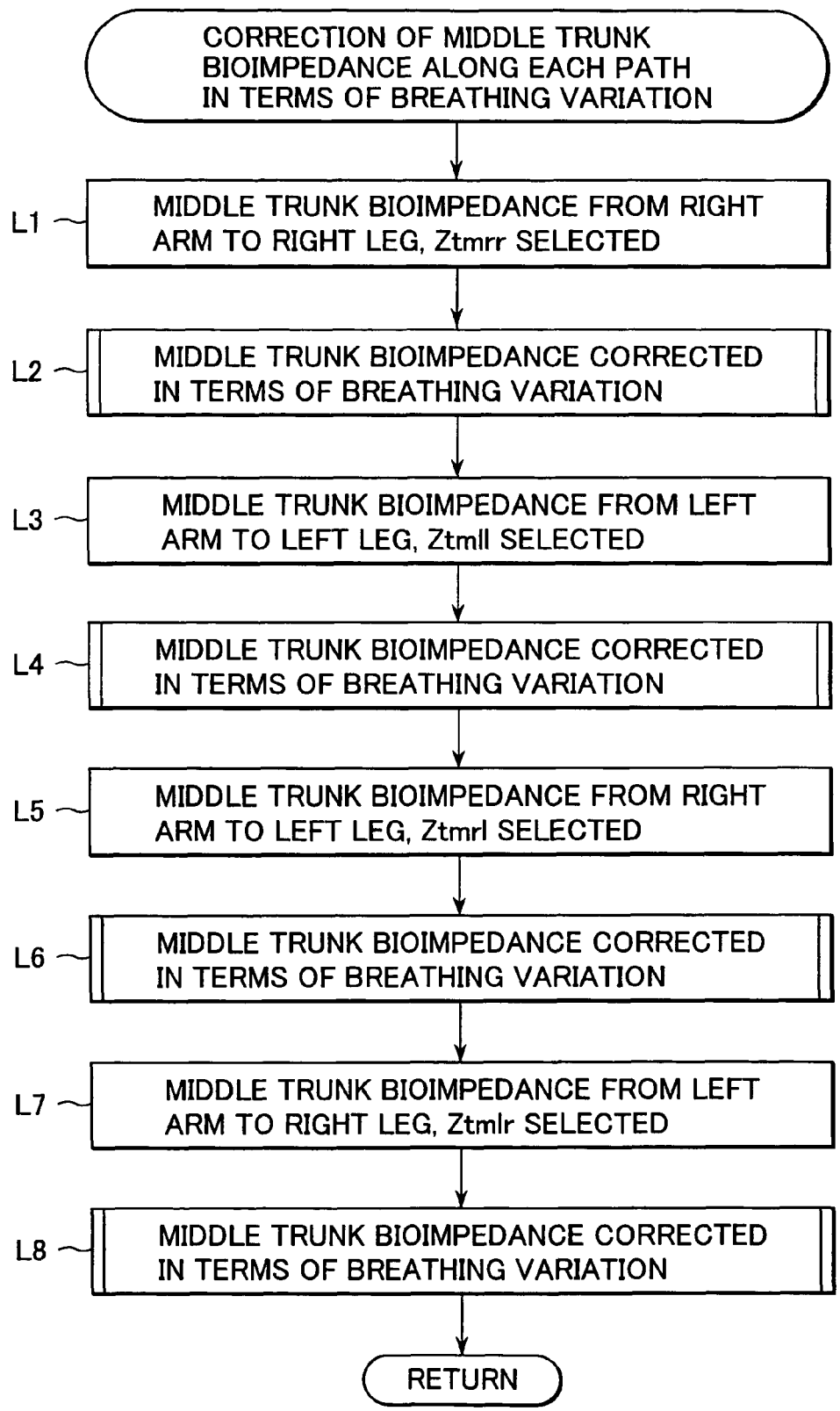
FIG. 23 is a subroutine flow chart depicting how EMBODIMENT 3 works in correcting the middle trunk bioimpedances appearing along different current flowing paths in terms of breathing variation at a selected step in the subroutine flow chart of FIG. 22.

Here, a subroutine (correction of each and every middle trunk bioimpedance (appearing along a different electric current flowing path) in terms of breathing variation) at step K3 in the above mentioned subroutine (measurement of limb and trunk bioimpedance; FIG. 22) is described below:

As shown in FIG. 23, in the microcomputer 151, the previously determined trunk bioimpedance Ztmrr appearing along the right arm-to-right leg electric current flowing path is selected at step L1, and then, the trunk bioimpedance Ztmrr is subjected to the same treatment at step L2 as in the subroutine (correction of the middle trunk bioimpedance in respect of the breathing variation), step G10, EMBODIMENT 2.

Sequentially in the microcomputer 151, the previously determined trunk bioimpedance Ztmll appearing along the left arm-to-left leg electric current flowing path is selected at step L3, and then, the trunk bioimpedance Ztmll is subjected to the same treatment (step L4) as in the subroutine (correction of the middle trunk bioimpedance in respect of the breathing variation), step G10, EMBODIMENT 2.

Sequentially in the microcomputer 151, the previously determined trunk bioimpedance Ztmrl appearing along the right arm-to-left leg electric current flowing path is selected at step L5, and then, the trunk bioimpedance Ztmrl is subjected to the same treatment (step L6) as in the subroutine (correction of the middle trunk bioimpedance in respect of the breathing variation), step G10, EMBODIMENT 2.

Sequentially in the microcomputer 151, the previously determined trunk bioimpedance Ztmlr appearing along the left arm-to-right leg electric current flowing path is selected at step L7, and then, the trunk bioimpedance Ztmlr is subjected to the same treatment (step L8) as in the subroutine (correction of the middle trunk bioimpedance in respect of the breathing variation), step G10, EMBODIMENT 2. Thus, this working mode is finished.

EMBODIMENT 4

Figure 24:
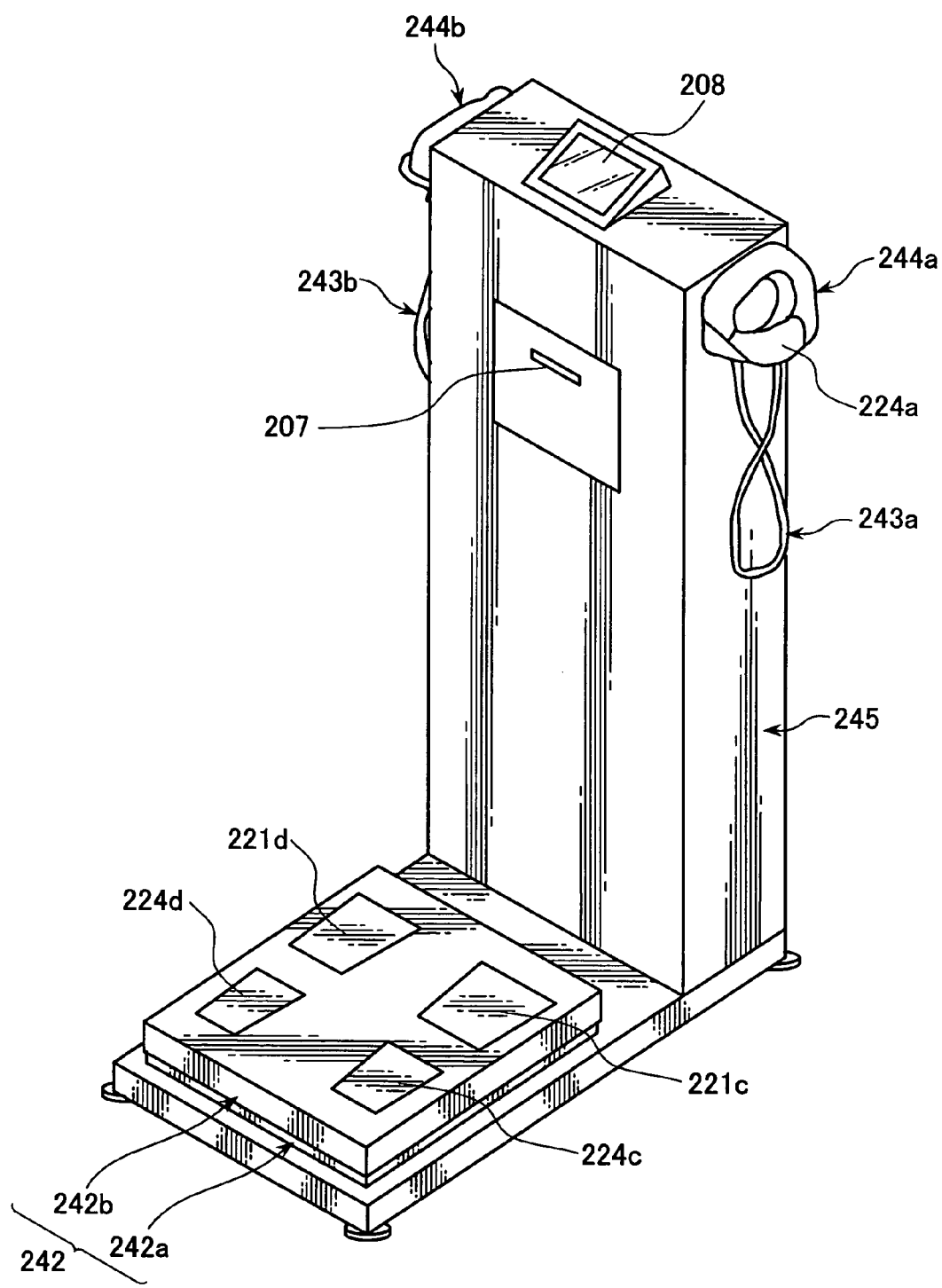
FIG. 24 is a perspective view of an apparatus for assuming information on the amount accumulated visceral fat according to EMBODIMENT 4 of the present invention.
Figure 25:
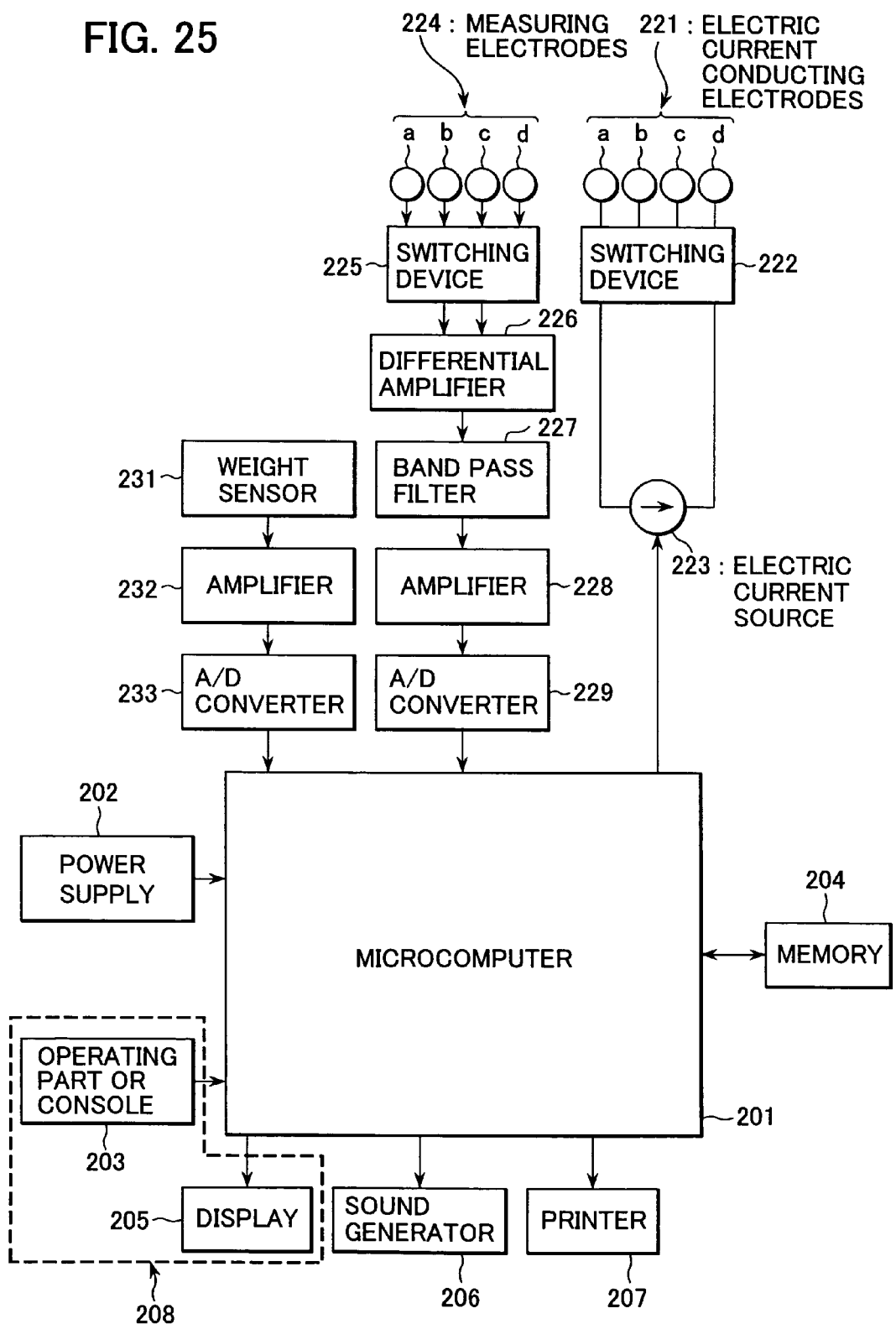
FIG. 25 is a structural block diagram of the apparatus for assuming information on the amount accumulated visceral fat of EMBODIMENT 4.

FIG. 24 is a perspective view of an apparatus for assuming information on the amount accumulated visceral fat according to EMBODIMENT 4 of the present invention, and FIG. 25 is a structural block diagram of the apparatus of FIG. 24, which comprises:
a body identifying unit for obtaining information on the identification of a human body; a breathing function determining unit for obtaining information on the breathing function, which comprises a maximum-breathing-caused, trunk bioimpedance variation measuring unit for determining the variation of the trunk bioimpedance at the time of maximum breathing and a vital capacity calculating unit;
a body composition determining unit for obtaining information on the body composition of the human body, which comprises a limb bioimpedance determining unit, a trunk bioimpedance determining unit and a body composition calculating unit; and
a computing unit for calculating information on the amount accumulated visceral fat on the basis of the so obtained pieces of information concerning the identification of the human body, the breathing function and the body composition.

Specifically the apparatus for assuming information on the amount accumulated visceral fat according to EMBODIMENT 4 comprises a power supply 202, an operating part or console 203, switching devices 222, 225, a differential amplifier 226, a band pass filter or BPF 227, an electric current source 223, amplifiers 228 and 232, A/D converters 229 and 233, a memory 204, a display 205, a sound generator 206, a printer 207 and a microcomputer 201, all of which are packaged in the housing 245. The base 242 comprises a base plate 242a and an overlying flat 242b. The housing 245 is integrally connected to the base 242, and electric cords 243a and 243b extends from the housing 245 to the opposite grips 244a and 244b. The base 242 has electric current conducting electrodes 221c, 221d, measuring electrodes 224c, 224d arranged on the flat 242b, and a weight sensor 231 built in the base plate 242a. One of the opposite grips 244a has an electric current conducting electrode 221a and a measuring electrode 224a attached thereon, whereas the other grip 244b has an electric current conducting electrode 221b and a measuring electrode 224b attached thereon. The printer 207 is arranged on the front of the housing 245.

The power supply 202 is similar to the power supply 52 in Embodiment 1, and the differential amplifier 226, the band pass filter 227, the electric current source 223, the amplifier 228 and the A/D converter 229 are similar to the differential amplifier 126, the band pass filter 127, the electric current source 123, the amplifier 128 and the A/D converter 129 in EMBODIMENT 2. The electric current conducting electrodes 221, the measuring electrodes 224, the switching devices 222, 225, the weight sensor 231, the amplifier 232, and the A/D converter 233 are similar to the electric current conducting electrodes 171, the measuring electrodes 174, the switching devices 172, 175, the weight sensor 181, the amplifier 182, and the A/D converter 183 in EMBODIMENT 3.

The memory 204 stores at least the following pieces of information:
i) pieces of information concerning identification of the human body (sex, age, height and weight) entered by the operating part or console 203;
ii) a limb bioimpedance (upper-limb bioimpedance, lower-limb bioimpedance), a trunk bioimpedance (middle trunk bioimpedance) and the variation of trunk bioimpedance at the time of maximum breathing, all determined by using the measuring electrodes 224, the switching devices 222, 225, the differential amplifier 226, the amplifier 228, the A/D converter 229 and microcomputer 201 all together;
iii) pieces of information calculated by the microcomputer 201 (later described) and concerning: the physical size and shape of the human body (upper limb length, lower limb length, middle trunk length, abdominal circumference); the body composition (body fat rate, limb skeletal muscle mass, middle trunk skeletal muscle mass, middle trunk skeletal muscle bioimpedance, abdominal subcutaneous fat amount (mass), abdominal subcutaneous fat bioimpedance, visceral mass, visceral bioimpedance, visceral fat bioimpedance, ratio of visceral fat/subcutaneous fat, trunk mass, trunk skeletal muscle rate); the body mass index; the breathing function (forced vital capacity, standard vital capacity, vital capacity/standard vital capacity percent); and the visceral fat accumulation (visceral fat rate, visceral fat amount (mass), ratio of visceral fat/subcutaneous fat).

The operating part or console 203 is a touch panel comprising a power key and setting keys, and the touch panel is combined with the display unit 205, and is used in entering pieces of information on the identification of the human body (sex, age, height, weight and other attributes).

The display 205 shows at least following pieces of information concerning:
i) the normal breathing guidance which the microcomputer 201 has under control, as later described;
ii) the maximum breathing guidance which the microcomputer 201 has under control, as later described;
iii) results of calculation by the microcomputer 201 (later described), including the body composition (body fat rate, limb skeletal muscle mass, middle trunk skeletal muscle mass, middle trunk skeletal muscle bioimpedance, abdominal subcutaneous fat amount (mass) based on the abdominal circumference, abdominal subcutaneous fat bioimpedance, visceral mass, visceral bioimpedance, visceral fat bioimpedance, trunk mass, trunk skeletal muscle rate), the body mass index, the breathing function (forced vital capacity, standard vital capacity, vital capacity/standard vital capacity percent), and the visceral fat accumulation estimated on the basis of the visceral fat bioimpedance (visceral fat rate, visceral fat amount (mass), ratio of visceral fat/subcutaneous fat);

vi) advisory message about the estimated information on the visceral fat accumulation provided by the microcomputer 201, as later described.

The sound generator comprises a buzzer responsive to at least following pieces of information for producing different sounds:

i) information on the normal breathing guidance controlled by the microcomputer 201, as later described;

ii) information on the maximum breathing guidance controlled by the microcomputer 201, as later described; and iii) advisory message about the estimated result of the visceral fat accumulation controlled by the microcomputer 201, as later described.

The printer 207 types out at least following pieces of information:

i) information on the normal breathing guidance controlled by the microcomputer 201, as later described;

ii) information on the maximum breathing guidance controlled by the microcomputer 201, as later described;

iii) results of calculation by the microcomputer 201 (later described), including the body composition (body fat rate, limb skeletal muscle mass, middle trunk skeletal muscle mass, middle trunk skeletal muscle bioimpedance, abdominal subcutaneous fat amount (mass) based on the abdominal circumference, abdominal subcutaneous fat bioimpedance, visceral mass, visceral bioimpedance, visceral fat bioimpedance, trunk mass, trunk skeletal muscle rate), the body mass index, the breathing function (forced vital capacity, standard vital capacity, vital capacity/standard vital capacity percent), and the visceral fat accumulation estimated on the basis of the visceral fat bioimpedance (visceral fat rate, visceral fat amount (mass), ratio of visceral fat/subcutaneous fat); and iv) advisory message about the estimated result of the visceral fat accumulation, controlled by the microcomputer 201, as later described.

The microcomputer 201 comprises a CPU, a ROM for storing control and operation programs, a RAM for temporarily storing the results of arithmetic operations along with the determinations and decisions, a timer, I/O ports and other units and parts. The so constructed microcomputer 201 functions to:

perform required arithmetic operations for obtaining pieces of information concerning; the physical size and shape (upper limb length, lower limb length, middle trunk length, abdominal circumference); the body composition (body fat rate, limb skeletal muscle mass, middle trunk skeletal muscle mass, middle trunk skeletal muscle bioimpedance, abdominal subcutaneous fat amount (mass) based on the abdominal circumference, abdominal subcutaneous fat bioimpedance, visceral mass, visceral bioimpedance, visceral fat bioimpedance, trunk mass, trunk skeletal muscle rate); the body mass index; the breathing function (forced vital capacity, standard vital capacity, vital capacity/standard vital capacity percent); the visceral fat accumulation estimated on the basis of the visceral fat bioimpedance (visceral fat rate, visceral fat amount (mass), ratio of visceral fat/subcutaneous fat); the visceral fat accumulation estimated on the basis of the vital capacity (visceral fat rate, visceral fat amount (mass), ratio of visceral fat/subcutaneous fat);

make a decision as to whether the condition is normal or abnormal in measurement, and as to whether the information on the breathing function indicates normal or abnormal condition;

determine limb bioimpedance and trunk bioimpedance, and the variation of trunk bioimpedance; and give visual and/or vocal messages informing the user of all required pieces of information.

The software programs for determining the body composition (middle trunk skeletal muscle mass, trunk mass based on the vital capacity) and the visceral fat accumulation on the basis of the vital capacity (visceral fat amount (mass), visceral fat rate) contain the following arithmetic operation:

$$MMtm = a13 \times MMl + b13 \times MMu + c13 \times Ztmpp + d13 \tag{30}$$

$$VC(\text{or } FVC) = \alpha m \times (Ztmpp \times MMtm)^\beta + \gamma m \tag{31a}$$

$$VC(\text{or } FVC) = \alpha f \times (Ztmpp \times MMtm)^\beta + \gamma f \tag{31b}$$

$$FV = a14m \times VC/Hm + b14m \times W + c14m \times Age + d14m \tag{32a}$$

$$FV = a14f \times VC/Hf + b14f \times W + c14f \times Age + d14f \tag{32b}$$

$$TM = MMtm + VM + FSa + FVz(\text{or } FV) \tag{33}$$

$$\%VFat = FVz(\text{or } FV)/TM \times 100 \tag{34}$$

MMtm: middle trunk skeletal muscle mass;
VC: vital capacity;
FVC: forced vital capacity;
FV: visceral fat amount (mass);
% VFat: visceral fat rate;
TM: trunk mass;
MMl: lower limb skeletal muscle mass;
MMu: upper limb skeletal muscle mass;
Ztmpp: maximum-breathing-caused, middle trunk bioimpedance variation;
H: height;
W: weight
Age: age;
FSa: abdominal subcutaneous fat amount (mass) based on abdominal circumference
FVz: visceral fat amount (mass) based on visceral fat bioimpedance
$\alpha m$, $\gamma m$, a14m, b14m, c14m, d14m: constants for males
$\alpha f$, $\gamma f$, a14f, b14f, c14f, d14f: constants for females
a13, b13, c13, d13, $\beta$ ($\beta=\frac{1}{2}$ in this example): constants The pieces of information concerning: body composition (body fat rate, limb skeletal muscle mass, middle trunk skeletal muscle bioimpedance, abdominal subcutaneous fat amount (mass) based on the abdominal circumference, abdominal subcutaneous fat bioimpedance, visceral mass, visceral bioimpedance, visceral fat bioimpedance, trunk mass, trunk skeletal muscle rate); the visceral fat accumulation estimated on the basis of the visceral fat bioimpedance (visceral fat rate, visceral fat amount (mass), ratio of visceral fat/subcutaneous fat); the visceral fat accumulation based on the vital capacity (ratio of visceral fat/pannicule) can be calculated according to the equations (12), (13), (14), (16), (17a), (17b), (18), (19a), (19b), (20a), (20b), (21), (22a), (22b), (23), (26) and (29) as in EMBODIMENT 3.

The body mass index and the information on breathing function (standard vital capacity, vital capacity/standard vital capacity percent) can be calculated according to the equations (2a), (2b), (3) and (7) as in EMBODIMENT 1.

The operation concerning information on the physical size and shape (upper limb length, lower limb length, middle trunk length, abdominal circumference) can be carried out by using operation programs concerning:
calibration curve data representing the relation between the upper limb length and the information on the identification of the human body (at least any one of sex, age, height and weight);
calibration curve data representing the relation between the lower limb length and the information on the identification of the human body (at least any one of sex, age, height and weight);
calibration curve data representing the relation between the middle trunk length and the information on the identification of the human body (at least any one of sex, age, height and weight); and
calibration curve data representing the relation between the abdominal circumference and the information on the identification of the human body (at least any one of sex, age, height and weight). The calibration curve data is given in the correlation type or correlation table.

The operating part or console 203, the weight sensor 231, the amplifier 232, the A/D converter 233, the memory 204, the microcomputer 201 and the power supply 202 all together make up the body identifying unit for obtaining information on the identification of the human body. The electric current conducting electrodes 221, the measuring electrodes 224, the differential amplifier 226, the band pass filter 227, the current source 223, the amplifier 228, the A/D converter 229, the memory 204, the microcomputer 201 and the power supply 202 all together make up the limb bioimpedance determining unit, the trunk bioimpedance determining unit and the maximum-breathing-caused, trunk bioimpedance variation determining unit. Finally, the microcomputer 201 and the power supply 202 make up the body composition calculating unit, the vital capacity calculating unit and the visceral fat accumulation calculating unit.

FIG. 26 shows a main flowchart and FIGS. 27, 28, 29, 30, 31 and 32 show sub-routine flowcharts. Referring to these figures, the manner in which the apparatus for assuming information on the amount accumulated visceral fat according to EMBODIMENT 4 works is described below.

First, referring to FIG. 26, at the outset the power supply key turns on, allowing the power supply 202 to supply the parts of the electrical system with electricity, thereby permitting the entering of the information on the identification of the human body (sex, age, height and weight). The setting keys are selectively depressed to enter these pieces of information into the memory 204 (step M1).

Then, selection of the way of obtaining the information on the physical size and shape of the human body is permitted ("entering" or "assuming").

The setting key for "entering" is selected and depressed (step M2), thereby entering the pieces of information concerning the physical size and shape (upper limb length, lower limb length, middle trunk length and abdominal circumference). Thus, the desired pieces of information are stored in the memory 204 (step M3).

Contrarily the setting key for "assuming" is selected and depressed (step M2), thereby allowing the microcomputer 201 to calculate the pieces of information concerning the physical size and shape (upper limb length, lower limb length, middle trunk length and abdominal circumference), as later described. The so calculated pieces of information are stored (step M4)

Sequentially, the limb bioimpedance (upper limb bioimpedance, lower limb bioimpedance) is measured by the limb bioimpedance determining unit (step M5).

Sequentially, the trunk bioimpedance (middle trunk bioimpedance) is measured by the trunk bioimpedance determining unit, and the variations of the trunk bioimpedance at the time of the maximum inspiration and at the time of maximum expiration are determined by the maximum-breathing-caused, trunk bioimpedance variation determining unit (step M6), as later described (step M6).

Then, the microcomputer 201 calculates the pieces of information on the body composition (body fat rate, limb skeletal muscle mass, middle trunk skeletal muscle mass, middle trunk skeletal muscle bioimpedance, abdominal subcutaneous fat amount (mass), abdominal subcutaneous fat bioimpedance, visceral mass, visceral bioimpedance), and the so calculated pieces of information are stored in the memory 204 (step M7).

The microcomputer 201 calculates the body mass index according to the equation (7) by substituting the information on the identification of the human body (height and weight) retrieved from the memory 204, and the so determined body mass index is stored in the memory 204 (step M8).

Sequentially, in the microcomputer 201, the information on breathing function (forced vital capacity, standard vital capacity, vital capacity/standard vital capacity percent) is calculated, and the so calculated pieces of information are stored in the memory (204) (step M9).

Sequentially, in the microcomputer 201, the information on visceral fat accumulation (visceral fat rate, visceral fat amount (mass), ratio of visceral fat/subcutaneous fat) and the information on body composition (visceral fat bioimpedance, trunk mass, trunk skeletal muscle) are calculated, and the so calculated pieces of information are stored in the memory (204) (step M10).

Sequentially, the display 205 shows following items all retrieved from the memory 204:
the information on body composition (body fat rate, limb skeletal muscle mass, middle trunk skeletal muscle mass, middle trunk skeletal muscle bioimpedance, abdominal subcutaneous fat amount (mass) based on the vital capacity, abdominal subcutaneous fat bioimpedance, visceral mass, visceral bioimpedance, visceral fat bioimpedance, trunk mass, trunk skeletal muscle rate);
body mass index;
the information on breathing function (forced vital capacity, standard vital capacity, vital capacity/standard vital capacity percent);
the information on the visceral fat accumulation (visceral fat rate, visceral fat amount (mass), ratio of visceral fat/subcutaneous fat); and advisory messages about the results of assuming the information on visceral fat accumulation, which advisory messages are stored in the ROM, reading "Breathing (lung) function is normal", or "Breathing (lung) function is abnormal", accompanying two-dot, bee-like buzzing sound combination and two-dot-and-one dash, bee-like sound combination respectively (step M11). Thus, the series of procedures are finished.

Now, the sub-routines at some selected steps in the main flow (measurement of limb bioimpedance; measurement of trunk bioimpedance and maximum-breathing-caused, trunk bioimpedance variation; operation and storage of the information on body composition; operation and storage of the information on visceral fat accumulation and a decision about the information on breathing function) are described below.

One of such sub-routines is carried out at step M5 (measurement of limb bioimpedance).

Figure 27:
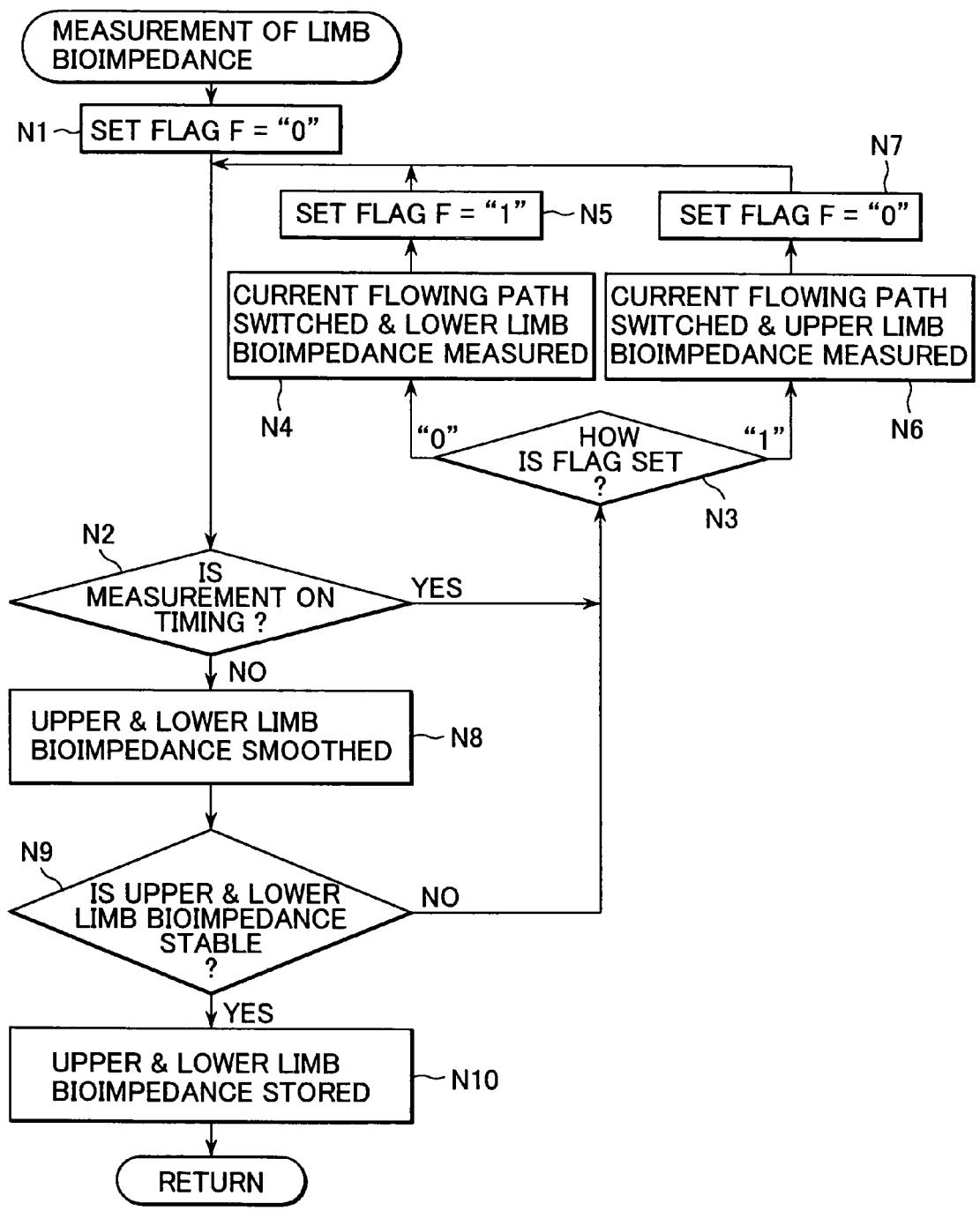
FIG. 27 is a subroutine flow chart depicting how the apparatus for assuming information on the amount accumulated visceral fat of EMBODIMENT 4 works in determining the limb bioimpedance at a selected step in the main flow chart of FIG. 26.

As shown in FIG. 27, first, the microcomputer 201 sets the flag to "0" (step N1).

Sequentially, the microcomputer 201 makes a decision as to whether or not the measurement just meets the starting point of the measurement timing (for example, 0.5 second-long sampling period) (step N2).

In the affirmative case ("YES" at step N2) a decision is made as to whether the flag is set to "0" or "1" (step N3). If the flag is set to "0", ("0" at step N3), the microcomputer 201 makes the switching devices 222 and 225, which are associated with the electric current conducting electrodes 221 and the measuring electrodes 224 respectively, turn to establish an electric current flowing path from the right leg to the left leg, allowing the limb determining unit to determine the lower limb bioimpedance (step N4). Then, the flag is set to "1" (step N5), allowing the proceeding to return to step N2. Otherwise, if the flag is set to "1", ("1" at step N3), the microcomputer 201 makes the switching devices 222 and 225, which are associated with the electric current conducting electrodes 221 and the measuring electrodes 224 respectively, turn to establish an electric current flowing path from the right arm to the left arm, allowing the limb determining unit to determine the upper limb bioimpedance (step N6). Then, the flag is set to "0" (step N7), allowing the proceeding to return to step N2.

If the measurement timing is off ("NO" at step N2), the microcomputer 201 has the so sampled upper and lower limb bioimpedances subjected to an effective treatment for smoothing (for instance, moving average) (step N8).

Sequentially, the microcomputer 20 makes a decision as to whether or not the smoothed upper and lower bioimpedances are stable (for example, whether or not each of all bioimpedances measured predetermined times is found within the predetermined allowable range) (step N9).

If each of the smoothed upper and lower bioimpedances is not stable ("NO" at step N9), the proceeding returns to step N3.

If each of the smoothed upper and lower bioimpedances is stable ("YES" at step N9), the last smoothed upper and lower bioimpedances are stored in the memory (step N10), and this working mode is finished.

Another or second sub-routine is the measurement of trunk bioimpedance and maximum-breathing-caused trunk bioimpedance variation, which is carried out at step M6 as follows.

Figure 28:
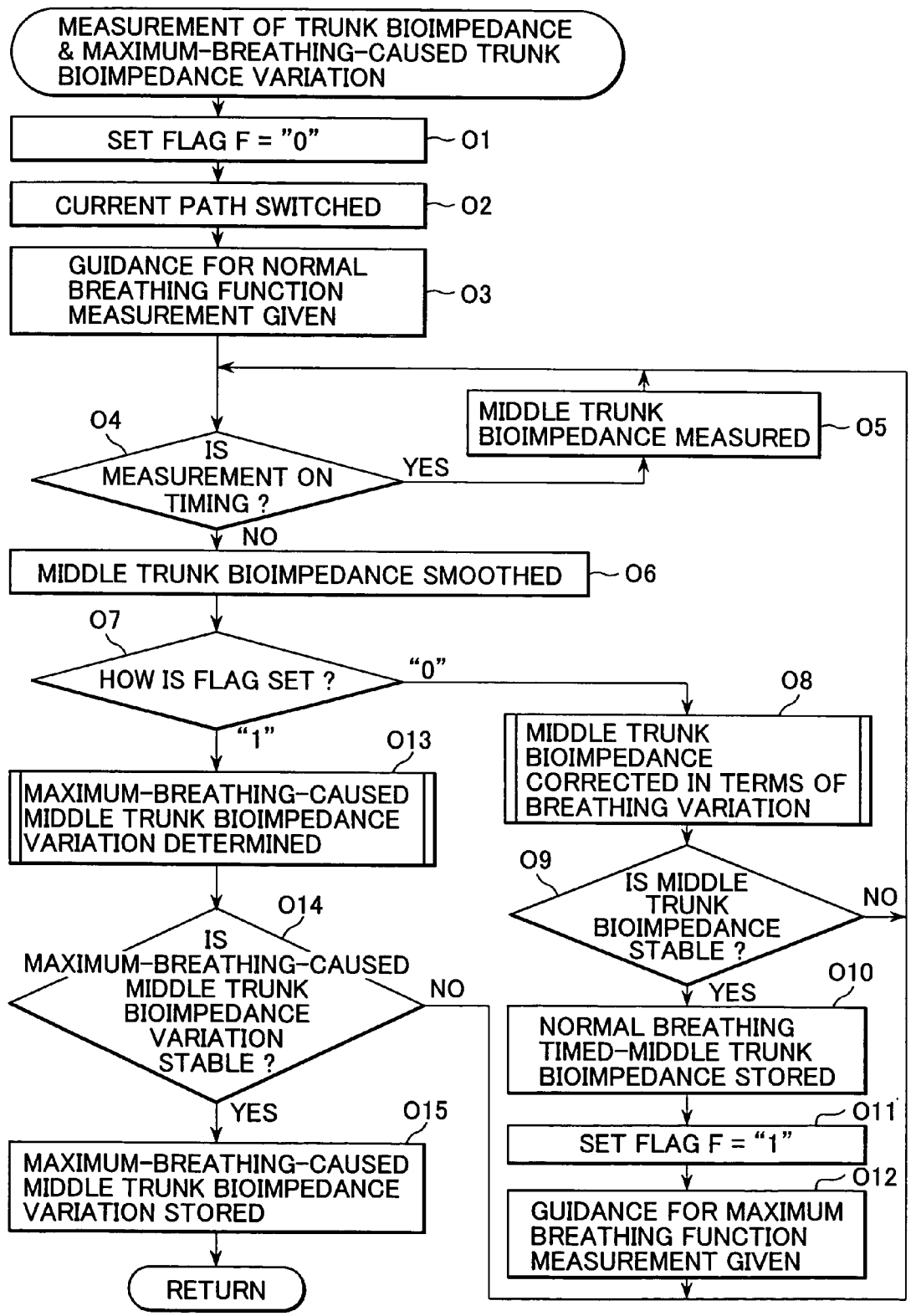
FIG. 28 is a subroutine flow chart depicting how EMBODIMENT 4 works in measuring the trunk bioimpedance and the trunk bioimpedance variation at the maximum breathing at a selected step in the main flow chart of FIG. 26.

As shown in FIG. 28, first, the microcomputer 151 sets the flag to "0" (step O1).

Then, the microcomputer 201 makes the switching devices 222 and 225, which are associated with the electric current conducting electrodes 221 and the measuring electrodes 224 respectively, turn to establish an electric current flowing path from the right arm to the right leg (otherwise, the left arm to the left leg; the right arm to the left leg or the left arm to the right leg) (step O2).

Sequentially, the visual and audible guidance for the normal breathing function measurement, which is stored in the ROM, is given by the display 205 and the sound generator 206 (step O3).

Sequentially, the microcomputer 201 makes a decision as to whether the measurement just meets the starting point of the measurement timing (for example, 0.1 second-long sampling period) (step O4).

In the affirmative case ("YES" at step O4), the trunk bioimpedance determining unit determines a middle trunk bioimpedance (step O5).

In the negative case ("NO" at step O4) the microcomputer 201 has the sampled middle trunk bioimpedance subjected to an effective treatment for smoothing (for example, moving average) (step O6).

Sequentially, the microcomputer 201 makes a decision as to whether the flag is set to "0" or "1" (step O7).

If the flag is set to "0", ("0" at step O7), in the microcomputer 201, the middle trunk bioimpedance is corrected in terms of the breathing variation (step O8), as is the case with the subroutine at G10 (correction of the middle truncus bioimpedance in terms of breathing variation) in EMBODIMENT 3. Then, the microcomputer 201 makes a decision as to whether or not the middle trunk bioimpedance corrected in terms of the breathing variation is stable (as to whether each of all middle trunk bioimpedances corrected predetermined times remains within a predetermined allowance every time) (step O9). In the negative case ("NO" at step O9), the proceeding returns to step O4. In the affirmative case ("YES" at step O9) the middle trunk bioimpedance last corrected in terms of breathing variation is stored (step O10). Sequentially the microcomputer 201 sets the flag to "1" (step O11), allowing the display 205 to show the visual guidance for the maximum breathing, which is retrieved from the ROM, reading "Repeatedly take into your lungs as much air as you can and send it out completely at the exact rate or timing directed from the sound generator." At the same time, the sound generator 206 produces a bee-like buzzing sound in regular inspiration-and-expiration interval (step O12). Then, the proceeding returns to step O4.

In case that the flag is set to "1" ("1" at step O7), the microcomputer 201 determines the variation of the middle trunk bioimpedance at the time of maximum breathing (step O13).

Sequentially, the microcomputer 201 makes a decision as to whether or not the maximum-breathing-caused middle trunk bioimpedance variation is stable (for example, whether or not each of all maximum-breathing-caused middle trunk bioimpedance variation measured predetermined times is found within the predetermined allowable range every time) (step O14).

In the negative case in which the maximum-breathing-caused middle trunk bioimpedance variation is not stable ("NO" at step O14), the proceeding returns to step O4.

In the affirmative case in which the maximum-breathing-caused middle trunk bioimpedance variation is stable ("YES" at step O14), the maximum-breathing-caused middle trunk bioimpedance variation determined last is stored in the memory 204 (step O15). Then, the proceeding is finished.

Here, described is a subroutine of determining the maximum-breathing-caused middle trunk bioimpedance variation, which subroutine is to be carried out at step O13 in the above mentioned subroutine of determining the trunk bioimpedance and the maximum-breathing-caused middle trunk bioimpedance variation.

Figure 29:
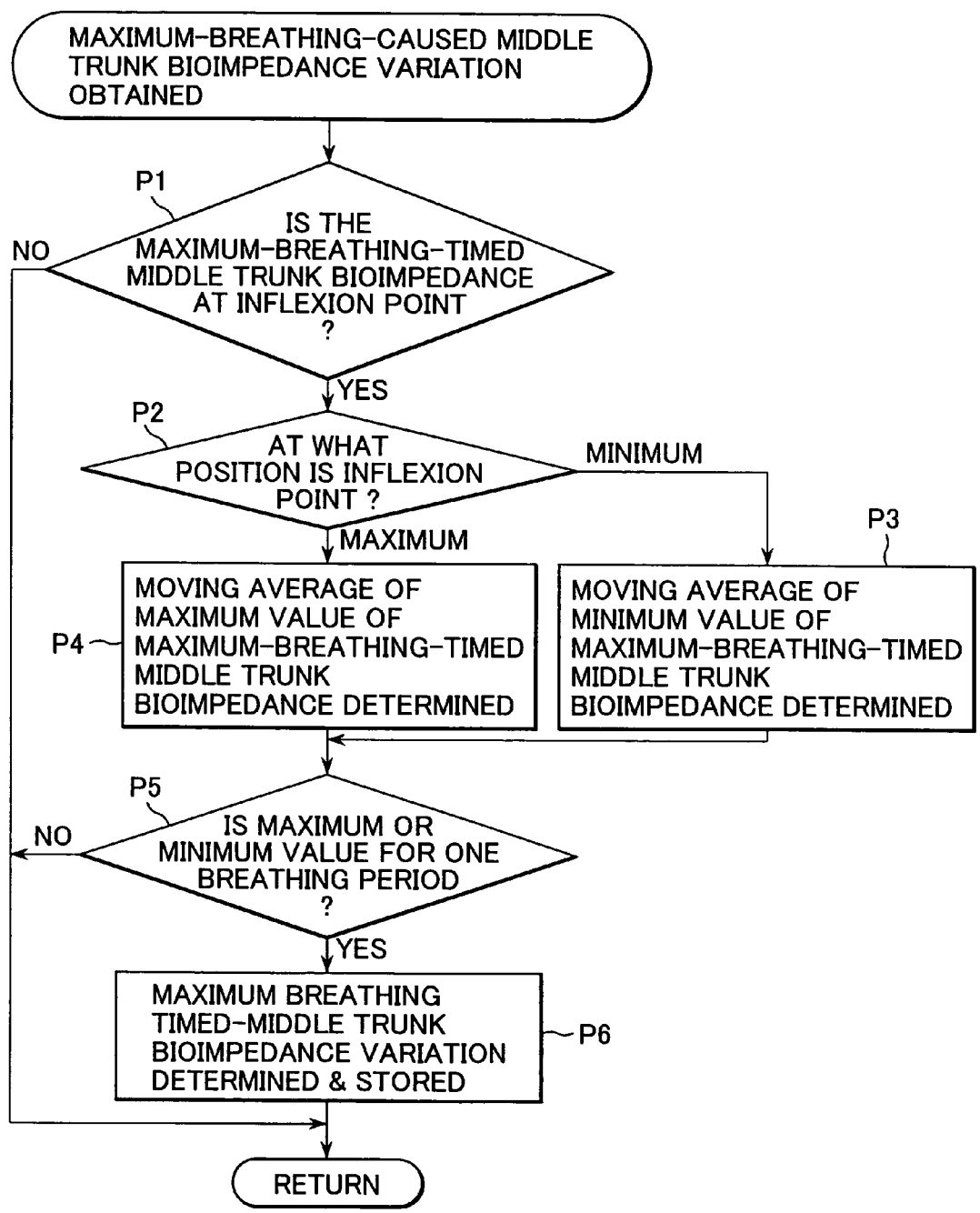
FIG. 29 is a subroutine flow chart depicting how EMBODIMENT 4 works in determining the middle trunk bioimpedance variation at the maximum breathing at a selected step in the subroutine flow chart of FIG. 28.

Referring to FIG. 29, the microcomputer 201 makes a decision as to whether the maximum-breathing-timed middle trunk bioimpedance is at the point of inflexion (step P1).

In the negative case ("NO" at step P1), this working mode is finished.

In the affirmative case ("YES" at step P1), a decision is made as to whether the smoothed maximum-breathing-timed middle trunk bioimpedance is at the "maximum" or "minimum" position (step P2).

In case that the point of inflexion is found at the "minimum" position ("minimum" at step P2), the value at the minimum point of inflexion (the minimum value of the maximum-breathing-timed middle trunk bioimpedance) is subjected to an effective treatment for moving average (step P3). Otherwise, in case that the point of inflexion is found at the "maximum" position ("maximum" at step P2), the value at the maximum point of inflexion (the maximum value of the middle trunk bioimpedance) is subjected to an effective treatment for moving average (step P4). Then, the proceeding advances to step P5.

Then, the microcomputer 151 makes a decision as to whether the minimum and maximum values of the maximum-breathing-timed middle trunk bioimpedance both subjected to the moving average treatment are the ones calculated over one breathing period (step P5).

In the negative case ("NO" at step P5), this working mode is finished.

In the affirmative case ("YES" at step P5), the microcomputer 201 determines the difference between the minimum and maximum values of middle trunk bioimpedance both subjected to the moving average (the maximum-breathing-caused middle trunk bioimpedance variation) at step P6, and then this working mode is finished.

Still another or third sub-routine is the operation and storage of the information on body composition, which is to be carried out at step M7 in the main flow chart as follows.

Figure 30:
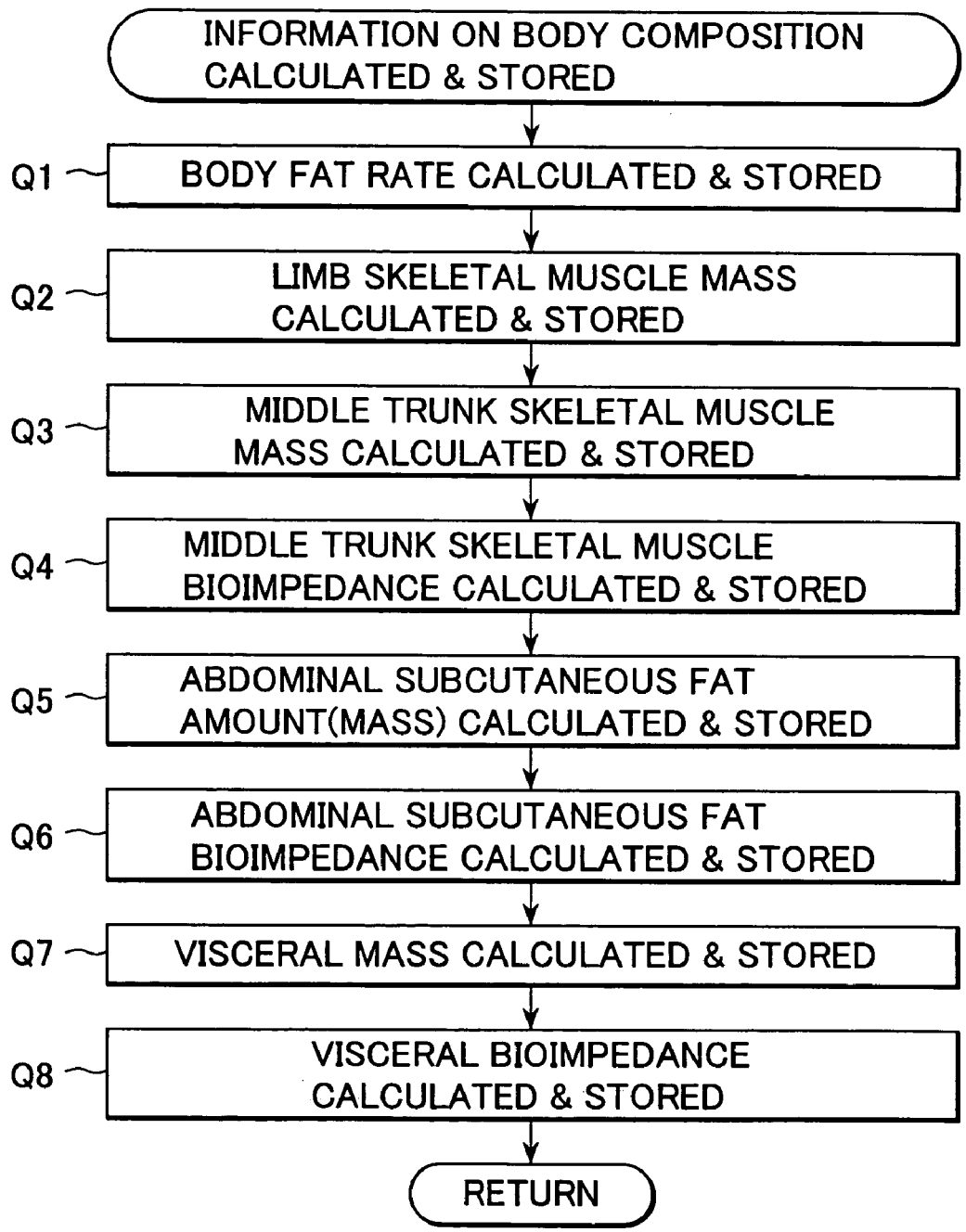
FIG. 30 is a subroutine flow chart depicting how EMBODIMENT 4 works in calculating and storing the information on the body composition at a selected step in the main flow chart of FIG. 26.

Referring to FIG. 30, first, the microcomputer 201 calculates the body fat rate according to the equation 12 by substituting in the equation, the information on the physical size and shape (upper trunk length, lower trunk length, middle trunk length and abdominal circumference), the limb bioimpedance (upper limb bioimpedance and lower limb bioimpedance) and trunk bioimpedance (middle trunk bioimpedance) all retrieved from the memory 204, and the so calculated body fat rate is stored in the memory 204 (step Q1).

Sequentially the microcomputer 201 determines the lower limb skeletal muscle mass according to the equation 13 by substituting in the equation, the information on the physical size and shape (lower limb length) and the limb bioimpedance (lower limb bioimpedance) both retrieved from the memory 204. Also, the microcomputer 201 determines the upper limb skeletal muscle mass according to the equation 14 by substituting in the equation, the information on the physical size and shape (upper limb length) and the limb bioimpedance (upper limb bioimpedance) both retrieved from the memory 204. The so determined lower and upper limb skeletal muscle masses are stored in the memory 204 (step Q2).

Sequentially, the microcomputer 201 determines the middle trunk skeletal muscle mass according to the equation 30 by substituting in the equation, the lower and upper limb skeletal muscle masses and the maximum-breathing-timed middle trunk bioimpedance, all of which are retrieved from the memory 154. The so determined middle trunk skeletal muscle mass is stored in the memory 204 (step Q3).

Sequentially, the microcomputer 201 determines the middle trunk skeletal muscle bioimpedance according to the equation 16 by substituting in the equation the so determined middle trunk skeletal muscle mass and the information on the physical size and shape (height), which are retrieved from the memory 204. Then, the so determined middle trunk skeletal muscle bioimpedance is stored in the memory 204 (step Q4).

Sequentially, the microcomputer 201 determines the abdominal subcutaneous fat amount (mass) according to the equation 17a or 17b by substituting in the equation, the information on the physical size and shape (abdominal circumference) and the information on the identification of the human body (age, height and weight), which are retrieved from the memory 204, and the so determined abdominal subcutaneous fat amount (mass) is stored in the memory 204 (step Q5). The equation 17a is applied to males (sex in the identification of the human body) whereas the equation 17b is applied to females (sex in the identification of the human body).

Sequentially, the microcomputer 201 determines the abdominal subcutaneous fat bioimpedance according to the equation 18 by substituting in the equation, the abdominal subcutaneous fat amount (mass) and the information on the identification of the human body (height), both retrieved from the memory 204, and the so determined abdominal subcutaneous fat bioimpedance is stored in the memory 204 (step Q6).

Sequentially the microcomputer 201 determines the visceral mass according to the equation 19a or 19b by substituting in the equation, the information on the identification of the human body (age, height and weight) retrieved from the memory 204, and the so determined visceral mass is stored in the memory 204 (step Q7). The equation 19a is applied to males (sex) whereas the equation 19b is applied to females (sex).

Sequentially, the microcomputer 201 determines the visceral bioimpedance according to the equation 20a or 20b by substituting in the equation, the visceral mass and the information on the identification of the human body (age, height and weight) both retrieved from the memory 204, and the so determined visceral bioimpedance is stored in the memory 204 (step Q8). The equation 20a is applied to males (sex) whereas the equation 20b is applied to females (sex).

Yet still another or fourth sub-routine is the operation and storage of information on the breathing function to be carried out at step M9 in the main flow chart, which fourth subroutine is described below in detail.

Referring to FIG. 31, first, the microcomputer 201 calculates the vital capacity according to the equation 31a or 31b by substituting in the equation, the maximum-breathing-caused middle trunk bioimpedance variation and the middle trunk skeletal muscle mass both retrieved from the memory 204, and the so calculated vital capacity is stored in the memory 204 (step R1).

Subsequently, the microcomputer 201 calculates the standard vital capacity according to the equation 2a or 2b by substituting in the equation, the information on identification of the human body (age, height) retrieved from the memory 204, and the so calculated standard vital capacity is stored in the memory 204 (step R2). The equation 2a is applied to males (sex) whereas the equation 2b is applied to females (sex).

Sequentially the microcomputer 201 calculates the vital capacity/standard vital capacity percent according to the equation 3 by substituting in the equation, the vital capacity and the standard vital capacity retrieved from the memory 204, and the so calculated vital capacity/standard vital capacity percent is stored in the memory 204 (step R3). Then, this working mode is finished.

Yet still another or fifth sub-routine is the operation and storage of visceral fat accumulation, which is to be carried out at step M10 in the main flow chart as follows.

Referring to FIG. 32, first, the microcomputer 201 determines the visceral fat bioimpedance according to the equation 21 by substituting in the equation, the middle trunk bioimpedance, the middle trunk skeletal muscle bioimpedance, the abdominal subcutaneous fat bioimpedance, and the visceral bioimpedance all retrieved from the memory 204, and the so determined visceral fat bioimpedance is stored in the memory 204 (step S1).

Sequentially, the microcomputer 201 determines the visceral fat amount (mass) on the basis of the visceral fat bioimpedance according to the equation 22a or 22b by substituting in the equation, the visceral fat bioimpedance and the information on identification of the human body (age, height, weight) both retrieved from the memory 204, and the so determined visceral fat amount (mass) based on the visceral fat bioimpedance is stored in the memory 204. Also, the visceral fat amount (mass) is determined on the basis of the vital capacity according to the equation 32a or 32b by substituting the vital capacity and the information on identification of the human body (age, height, weight) both retrieved from the memory 204, and the so determined visceral fat amount (mass) based on the vital capacity is stored in the memory 204 (step S2). The equation 32a is applied to males whereas the equation 32b is applied to females.

Sequentially, the microcomputer 201 makes a decision as to whether the breathing function is normal or abnormal. Specifically the breathing function is normal as long as "the visceral fat amount (mass) based on the visceral fat bioimpedance is equal to or larger than the visceral fat amount (mass) based on the vital capacity, and otherwise, the breathing function is abnormal (step S3).

In case that the breathing function is found normal at step S3, the microcomputer 201 determines the ratio of visceral fat/subcutaneous fat according to the equation 29 by substituting in the equation, the visceral fat amount (mass) based on the vital capacity and the abdominal subcutaneous fat amount (mass) both retrieved from the memory 204, and the so determined ratio of visceral fat/subcutaneous fat is stored in the memory 204. Otherwise, in case that the breathing function is found abnormal at step S3, the microcomputer 201 determines the ratio of visceral fat/subcutaneous fat on the basis of the visceral fat bioimpedance according to the equation 23 by substituting in the equation, the visceral fat amount (mass) based on the visceral fat bioimpedance and the abdominal subcutaneous fat amount (mass) both retrieved from the memory 204, and the so determined ratio of visceral fat/subcutaneous fat based on the visceral fat bioimpedance is stored in the memory 204 (step S4).

Sequentially, the microcomputer 201 determines the trunk mass according to the equation 33 by substituting in the equation, the middle trunk skeletal muscle, the visceral mass, the abdominal subcutaneous fat amount (mass) and the visceral fat amount (mass) based on the visceral fat bioimpedance or the vital capacity all retrieved from the memory 204, and the so determined trunk mass is stored in the memory 204 (step S5).

Sequentially, the microcomputer 201 determines the visceral fat rate according to the equation 34 by substituting in the equation, the trunk mass and the visceral fat amount (mass) based on the visceral fat bioimpedance or the vital capacity, all retrieved from the memory 204, and the so determined visceral fat rate is stored in the memory 204 (step S6).

Sequentially, the microcomputer 201 determines the trunk skeletal muscle rate according to the equation 26 by substituting in the equation, the trunk mass and the middle trunk skeletal muscle mass, both retrieved from the memory 204, and the so determined trunk skeletal muscle rate is stored in the memory 204 (step S7). Thus, this working mode is finished.

The apparatus for assuming information on the amount accumulated visceral fat according to EMBODIMENT 4 works as described above.

As may be understood from the above, the apparatus for assuming information on the amount accumulated visceral fat of EMBODIMENT 4 is so constructed that it may collect pieces of information concerning: the identification of the human body such as sex, age, height and weight; and the breathing function such as the vital capacity determined by the maximum-breathing-caused truncus bioimpedance variation determining unit; and may sure assume the information on the visceral fat accumulation (visceral fat rate) according to the equation (32a) or (32b) with ease and with a high degree of accuracy.

In EMBODIMENT 4 the information on the identification of the human body includes sex, age, height and weight to determine the visceral fat amount (mass) according to the equation (32a) or (32b). To improve the accuracy still more pieces of information on the physical size and shape (at least any one of the upper limb length, lower limb length, middle trunk length and abdominal circumference) may be additionally collected and used for better identification of the human body. Specifically these terms are multiplied by some coefficients, and added as independent variables to the equation 32a or 32b. Then, a visceral fat rate can be provided at a still higher degree of accuracy.

What is claimed is:

1. An apparatus for assuming information on the amount accumulated visceral fat of a human body comprising:
    a body identifying unit;
    a breathing function determining unit; a computing unit, wherein said body identifying unit obtains information on the identification of the human body;
    said breathing function determining unit obtains information on the breathing function; and
    said computing unit calculates information on the amount accumulated visceral fat on the basis of the so obtained pieces of information on the identification of the human body and the breathing function;
    wherein the breathing function determining unit comprises a trunk bioimpedance variation determining unit which determines the variation between the trunk bioimpedance at the time of maximum inspiration and that at the time of maximum expiration, and a vital capacity computing unit which calculates the information on the breathing function on the basis of the so determined trunk bioimpedance variation between the maximum inspiration and maximum expiration.

2. An apparatus for assuming information on the amount accumulated visceral fat of a human body according to claim 1 wherein it further comprises a body composition determining unit which obtains information on the body composition of the human body, thus permitting said computing unit to calculate information on the amount accumulated visceral fat on the basis of, among others, the so obtained pieces of information on the body composition of the human body.

3. An apparatus for assuming information on the amount accumulated visceral fat of a human body according to claim 2 wherein said body composition determining unit comprises a hand-to-hand bioimpedance determining unit which determines the bioimpedance appearing between both hands, and a body composition calculating unit which calculates information on the body composition of the human body on the basis of the so determined hand-to-hand impedance.

4. An apparatus for assuming information on the amount accumulated visceral fat of a human body according to claim 2 wherein said body composition determining unit comprises a limb bioimpedance determining unit which determines the bioimpedance appearing between two selected limbs, a trunk bioimpedance determining unit which determines the bioimpedance appearing between two selected points of the trunk, and a body composition calculating unit which calculates the body composition on the basis of the so determined limb bioimpedance and trunk bioimpedance.

5. An apparatus for assuming information on the amount accumulated visceral fat of a human body according to any of claims 2 or 3 wherein the information on the identification of the human body include sex, age, height and weight; the information on the breathing function include vital capacity; and the information on the body composition include the trunk skeletal muscle rate.

6. An apparatus for assuming information on the amount accumulated visceral fat of a human body according to claim 5 wherein the information on the amount accumulated visceral fat include at least one of the visceral fat rate, visceral fat amount and the ratio of visceral fat/subcutaneous fat.

7. An apparatus for assuming information on the amount accumulated visceral fat of a human body according to any of claims 2 or 3 wherein the information on the identification of the human body include sex, age, height and weight, and at least one of the upper limb length, lower limb length, trunk length and abdominal circumference; the information on the breathing function include vital capacity; and the information on the body composition include the trunk skeletal muscle rate.

8. An apparatus for assuming information on the amount accumulated visceral fat of a human body according to claim 7 wherein the information on the amount accumulated visceral fat include at least one of the visceral fat rate, visceral fat amount and the ratio of visceral fat/subcutaneous fat.

9. An apparatus for assuming information on the amount accumulated visceral fat of a human body according to claim 1, wherein the information on the identification of the human body include sex, age, height and weight, and the information on the breathing function includes vital capacity.

10. An apparatus for assuming information on the amount accumulated visceral fat of a human body according to claim 1, wherein the information on the identification of the human body include sex, age, height and weight, and at least one of the upper limb length, lower limb length, trunk length and abdominal circumference, and the information on the breathing function includes vital capacity.

11. An apparatus for assuming information on the amount accumulated visceral fat of a human body comprising:
a body identifying unit;
a breathing function determining unit; a computing unit, wherein said body identifying unit obtains information on the identification of the human body;
said breathing function determining unit obtains information on the breathing function; and
said computing unit calculates information on the amount accumulated visceral fat on the basis of the so obtained pieces of information on the identification of the human body and the breathing function;
wherein the information on the identification of the human body include sex, age, height and weight, and the information on the breathing function includes vital capacity.

12. An apparatus for assuming information on the amount accumulated visceral fat of a human body according to claim 11 wherein the information on the amount accumulated visceral fat include at least one of the visceral fat rate, visceral fat amount and the ratio of visceral fat/subcutaneous fat.

13. An apparatus for assuming information on the amount accumulated visceral fat of a human body comprising:
a body identifying unit;
a breathing function determining unit; a computing unit, wherein said body identifying unit obtains information on the identification of the human body;
said breathing function determining unit obtains information on the breathing function; and
said computing unit calculates information on the amount accumulated visceral fat on the basis of the so obtained pieces of information on the identification of the human body and the breathing function;
wherein the information on the identification of the human body include sex, age, height and weight, and at least one of the upper limb length, lower limb length, trunk length and abdominal circumference, and the information on the breathing function includes vital capacity.

14. An apparatus for assuming information on the amount accumulated visceral fat of a human body according to claim 13 wherein the information on the amount accumulated visceral fat include at least one of the visceral fat rate, visceral fat amount and the ratio of visceral fat/subcutaneous fat.

* * * * *